US007029893B2

(12) United States Patent
Usuda et al.

(10) Patent No.: US 7,029,893 B2
(45) Date of Patent: Apr. 18, 2006

(54) POLYNUCLEOTIDES ENCODING POLYPEPTIDES INVOLVED IN AMINO ACID BIOSYNTHESIS IN METHYLOPHILUS METHYLOTROPHUS

(75) Inventors: Yoshihiro Usuda, Kawasaki (JP); Yousuke Nishio, Kawasaki (JP); Hisashi Yasueda, Kawasaki (JP); Shinichi Sugimoto, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 59 days.

(21) Appl. No.: 10/375,039

(22) Filed: Feb. 28, 2003

(65) Prior Publication Data

US 2004/0170986 A1 Sep. 2, 2004

(51) Int. Cl.
*C12N 9/12* (2006.01)
*C07K 1/00* (2006.01)

(52) U.S. Cl. .................. 435/194; 435/183; 435/252.3; 435/320.1; 530/350; 536/23.1; 536/23.2

(58) Field of Classification Search ................ 435/183, 435/252.3, 193, 320.1, 6; 536/23.1, 23.2
See application file for complete search history.

(56) References Cited

U.S. PATENT DOCUMENTS

2004/0091891 A1 5/2004 Iomantas et al. ............. 435/6

2004/0170985 A1 9/2004 Usuda et al. ................. 435/6
2004/0170987 A1 9/2004 Usuda et al. ................. 435/6

FOREIGN PATENT DOCUMENTS

| EP | 0035831 | 9/1981 |
| EP | 0037273 | 10/1981 |
| EP | 0066994 | 12/1982 |
| EP | 1188822 | 3/2002 |
| WO | WO 02/38777 | 5/2002 |

OTHER PUBLICATIONS

Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492-495.*
U.S. Appl. No. 10/166,653, filed Jun. 12, 2002, Pending.
U.S. App. No. 09/926,299, filed Oct. 9, 2001, Gunji et al.

* cited by examiner

*Primary Examiner*—Richard Hutson
(74) *Attorney, Agent, or Firm*—Cermak & Kenealy,LLP; Shelly Guest Cermak

(57) ABSTRACT

The present invention provides polypeptides and polynucleotides involved in amino acid biosynthesis in *Methylophilus methylotrophus* and methods of producing amino acids in microorganisms having enhanced or attenuated expression of these polypeptides and/or polynucleotides.

20 Claims, No Drawings

POLYNUCLEOTIDES ENCODING POLYPEPTIDES INVOLVED IN AMINO ACID BIOSYNTHESIS IN METHYLOPHILUS METHYLOTROPHUS

BACKGROUND OF THE INVENTION

1. Field of the Invention

The present invention relates to novel polynucleotides encoding proteins involved in biosynthesis of amino acids including phenylalanine, tryptophan, tyrosine, aspartate, lysine, methionine, or threonine, derived from microorganisms belonging to methylotrophic bacteria and fragments thereof, polypeptides encoded by the polynucleotides and fragments thereof, polynucleotide arrays comprising the polynucleotides and fragments thereof.

2. Discussion of the Background

Amino acids such as L-lysine, L-glutamic acid, L-threonine, L-leucine, L-isoleucine, L-valine and L-phenylalanine are industrially produced by fermentation by using microorganisms that belong to the genus *Brevibacterium*, *Corynebacterium*, *Bacillus*, *Escherichia*, *Streptomyces*, *Pseudomonas*, *Arthrobacter*, *Serratia*, *Penicillium*, *Candida* or the like. In order to improve the productivity of amino acids, strains of the aforementioned microorganisms that have been isolated from nature or artificial mutants thereof have been used. Various techniques have also been disclosed for enhancing activities of L-amino acid biosynthetic enzymes by using recombinant DNA techniques to increase the L-amino acid-producing ability.

L-amino acid production has been increased considerably by breeding of microorganisms such as those mentioned above and by improvements in production methods. However, in order to meet a future increase in the demand for L-amino acids, development of methods for more efficiently producing L-amino acids at lower cost are still desired.

Conventional methods for producing amino acids by fermentation using methanol, which is a raw fermentation material available in large quantities at a low cost, employ *Achromobacter* or *Pseudomonas* microorganisms (Japanese Patent Publication (Kokoku) No. 45-25273/1970), *Protaminobacter* microorganisms (Japanese Patent Application Laid-open (Kokai) No. 49-125590/1974), *Protaminobacter* or *Methanomonas* microorganisms (Japanese Patent Application Laid-open (Kokai) No. 50-25790/1975), *Microcyclus* microorganisms (Japanese Patent Application Laid-open (Kokai) No. 52-18886/1977), *Methylobacillus* microorganisms (Japanese Patent Application Laid-open (Kokai) No. 491793/1992), *Bacillus* microorganisms (Japanese Patent Application Laid-open (Kokai) No. 3-505284/1991) and others.

However, only a few methods have been described for producing L-amino acids using *Methylophilus* bacteria in conjunction with recombinant DNA technology. Although methods described in EP 0 035 831 A, EP 0 037 273 A and EP 0 066 994 A have been described as methods for transforming *Methylophilus* bacteria using recombinant DNA, applying recombinant DNA techniques to improvement of amino acid productivity of *Methylophilus* bacteria has not been described. Only WO-00/61723 and WO-02/38777 disclose the improved production of lysine and phenylalanine, respectively, using genes involved in biosynthesis of each respective amino acid. In particular, WO-00/61723 discloses the ask gene, the dapA gene, the dapB gene, and the lysA gene, which encode aspartkinase, dihydrodipicolinate synthase, dihydrodipicolinate reductase, and diaminopimelinate decarboxylase, respectively. WO-02/38777 discloses the aroG gene and the pheA gene, which encode 3-deoxy-D-arabino-heptulosonate 7-phosphate synthase and bi-functional enzyme of chorismate mutase and prephenate dehydratase, respectively.

Therefore, prior to the present invention, only the ask gene, the dapA gene, the dapB gene, the lysA gene, the aroG gene and the pheA gene have been disclosed. Other genes isolated from *Methylophilus* bacteria that are involved in amino acid biosynthesis and which can be used to improve the yield of amino acids in cultured microorganisms remain elusive and undisclosed.

SUMMARY OF THE INVENTION

An object of the present invention is to provide novel measures for the improved production of amino acids or an amino acid, where these amino acids include asparagine, threonine, serine, glutamate, glycine, alanine, cysteine, valine, methionine, isoleucine, leucine, tyrosine, phenylalanine, histidine, lysine, tryptophan, arginine and the salts thereof. In a preferred embodiment the amino acids are L-amino acids.

Such a process includes bacteria, which express a protein comprising an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, and SEQ ID NO:54.

In one embodiment the polypeptides are encoded by a polynucleotide selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, and SEQ ID NO:53. In another embodiment the polypeptides are encoded by other polynucleotides which have substantial identity to the herein described polynucleotides or those which hybridize under stringent conditions.

Another object of the invention is to provide polynucleotide sequences selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, and SEQ ID NO:53; as well as those polynucleotides that have substantial identity to these nucleotide sequences, preferably at least 95% identity.

Another object of the invention is to provide isolated polypeptides having a sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, and SEQ ID NO:54; as well as those polypeptides that have substantial identity to these amino acid sequences, preferably at least 95% identity.

A further object of the invention is a method for producing a protein or proteins by culturing host cells containing the herein described polynucleotides under conditions and for a time suitable for expression of the protein and collecting the protein produced thereby.

Another object is the use of host cells having the polynucleotides described herein to produce amino acids, as well as the use of such isolated polypeptides in the production of amino acids.

Other objects of the invention include methods of detecting nucleic acid sequences homologous to at least one of: SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, and SEQ ID NO:53, particularly nucleic acid sequences encoding polypeptides that herein described proteins or polypeptides and methods of making nucleic acids encoding such polypeptides.

The above objects highlight certain aspects of the invention. Additional objects, aspects and embodiments of the invention are found in the following detailed description of the invention.

DETAILED DESCRIPTION OF THE INVENTION

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In addition, the materials, methods, and examples are illustrative only and are not intended to be limiting.

Reference is made to standard textbooks of molecular biology that contain definitions and methods and means for carrying out basic techniques, encompassed by the present invention. See, for example, Sambrook et al., Molecular Cloning: A Laboratory Manual, Third Edition, Cold Spring Harbor Laboratory Press, New York (2001), Current Protocols in Molecular Biology, Ausebel et al (eds.), John Wiley & Sons, New York (2001) and the various references cited therein.

*Methylophilus methylotrophus* (*M. methylotrophus*) is a gram negative rubles monophosphate cycle methanol-utilizer, which can be used for the large-scale production of a variety of fine chemicals including amino acids, nucleic acids, vitamins, saccharides, and so on. The polynucleotides of this invention, therefore, can be used to identify microorganisms, which can be used to produce fine chemicals, for example, by fermentative processes. Modulation of the expression of the polynucleotides encoding enzymes in the amino acid biosynthesis of the present invention, can be used to modulate the production of one or more fine chemicals from a microorganism (e.g., to improve the yield of production of one or more fine chemicals from *Methylophilus* or *Methylbacillus* species).

The proteins encoded by the polynucleotides of the present invention are capable of, for example, performing a function involved in the metabolism of intermediates in *M. methylotrophus*, such as , oxaloacetate, pyruvate, phosphoenolpyruvate, L-aspartate, L-homoserine, O-succinyl homoserine, homoserine phosphate, O-acetyl homoserine, homocysteine, tetrahydrodipicolinate, N-succinyl-alpha-amino-epsilon-keto-pimelate, N-succinyl diaminopimelate, LL-diaminopimelate, Meso-diaminopimelate, 3-deoxy-D-arabino-heptulosonate 7-phosphate, 3-dehydroquinate, 3-dehydroshikimate, shikimate, shikimate 3-phosphate, 5-enolpyruvoylshikimate-3-phosphate, chorismate, prephenate, 4-hydroxyphenylpyruvate, anthranilate, phosphoribosyl anthranilate, 1-(o-carboxyphenylamino)-1-deoxyribulose-5-phosphate, indoleglycerol phosphate, L-lysine, L-phenylalnine, L-tryptophan, L-tyrosine, L-methionine, and L-threonine.

Given the availability of cloning vectors used in *M. methylotrophus*, such as those disclosed in Methane and Methanol Utilizers, Plenum Press, New York (1992) edited by J. Colin Murrell and Howard Dalton, the nucleic acid molecules of the present invention may be used in the genetic engineering of this organism to make it better or more efficient producer of one or more fine chemicals.

There are a number of mechanisms by which the alteration of a protein of the present invention may affect the yield, production, and/or efficiency of production of a fine chemical from *M. methylotrophus* bacteria, which have the altered protein incorporated. Improving the ability of the cell to utilize pyruvate or phosphoenolpyruvate (e.g., by manipulating the genes encoding enzymes involved in the conversion of each compound into oxaloacetate), one may increase the yield or productivity of desired fine chemicals derived from oxaloacetate. Furthermore, by suppressing the activity of enzymes involved in the wasteful pathway such as the conversion of chorismate to 4-hydroxyphenylpyruvate, one may also increase the yield or productivity of desired phenylalanine.

"L-amino acids" or "amino acids" as used herein means one or more amino acids, including their salts, preferably chosen from the following: L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine.

"Isolated" as used herein means separated out of its natural environment.

"Substantial identity" as used herein refers to polynucleotides and polypeptides which are at least 70%, preferably at least 80% and more preferably at least 90% to 95% identical to the polynucleotides and polypeptides, respectively, according to the present invention.

"Polynucleotide" as used herein relates to polyribonucleotides and polydeoxyribonucleotides, it being possible for these to be non-modified RNA or DNA or modified RNA or DNA.

"Polypeptides" as used herein are understood to mean peptides or proteins which comprise two or more amino acids bonded via peptide bonds. In particular, the term refers to polypeptides which are at least 70%, preferably at least 80% and more preferably at least 90% to 95% identical to the polypeptides according to the present invention. Included within the scope of the present invention are polypeptide fragments of the polypeptides having a sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, and SEQ ID NO:54 or those which are identical to those described herein.

"Polynucleotides which encode the polypeptide" of the invention as used herein is understood to mean the sequences exemplified in this application as well as those sequences which have substantial identity to the nucleic acid sequences at least one of: SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, and SEQ ID NO:53 and which encode a molecule having one or more of the bioactivities of the associated gene products. Preferably, such polynucleotides are those which are at least 70%, preferably at least 80% and more preferably at least 90% to 95% identical to the nucleic acid sequences at least one of: SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, and SEQ ID NO:53.

Polynucleotides according to the invention may be employed as probes to isolate and/or identify RNA, cDNA and DNA molecules, e.g., full-length genes or polynucleotides which code for the polypeptides described herein. Likewise, the probes can be employed to isolate nucleic acids, polynucleotides or genes which have a high sequence similarity or identity with the polynucleotides of the invention.

Polynucleotides of the invention may also be used to design primers useful for the polymerase chain reaction to amplify, identify and/or isolate full-length DNA, RNA or other polynucleotides with high sequence homology or identity to the polynucleotides of the invention, as well as, polynucleotides that encode the polypeptides of the invention. Preferably, probes or primers are at least 15, 16, 17, 18, 19, 20, 21, 22, 23, 24, 25, 26, 27, 28, 29 or 30 nucleotides in length. Oligonucleotides with a length of at least 35, 40, 45, 50, 100, 150, 200, 250 or 300 nucleotides may also be used.

Methods of DNA sequencing are described inter alia by Sanger et al. (Proceedings of the National Academy of Sciences of the United States of America USA, 74:5463–5467, (1977)).

A person skilled in the art will find instructions for amplification of DNA sequences with the aid of the polymerase chain reaction (PCR) inter alia in the handbook by Gait: Oligonucleotide Synthesis: A Practical Approach (IRL Press, Oxford, UK, 1984) and in Newton and Graham: PCR $2^{nd}$ Edition (Springer Verlag, New York, 1997).

Additionally, methods employing DNA chips, microarrays or similar recombinant DNA technology that enables high throughput screening of DNA and polynucleotides that encode the herein described proteins or polynucleotides with high sequence homology or identity to the polynucleotides described herein. Such methods are known in the art and are described, for example, in Current Protocols in Molecular Biology, Ausebel et al (eds), John Wiley and Sons, Inc. New York (2000).

The polynucleotides and polypeptides of the present invention are involved in amino acids biosynthesis in *M. methylotrophus*. By way of example, the present inventors provide the following cited references (each of which are incorporated herein by reference) demonstrating that assays to assess the enzymatic activity of the polypeptides of the present invention are known and, as such, determination of whether a sequence falls within the scope of the present claims may be readily ascertained. These polynucleotides and polypeptides include:

1. Shikimate kinase enzyme comprises the amino acid sequence of SEQ ID NO:2 and is encoded by the aroK gene which comprises the polynucleotide SEQ ID NO:1 (Huang, L., Montoya, A. L. and Nester, E. W., J. Biol. Chem. (1975) 250:7675–7681);
2. 3-dehydroquinate synthase enzyme comprises the amino acid sequence of SEQ ID NO:4 and is encoded by a aroB gene which comprises the polynucleotide SEQ ID NO:3 (Frost, J. W., Bender, J. L. Kadonaga, J. T. and Knowles, J. R., Biochemistry (1984) 23:4470–4475);
3. 3-dehydroquinate dehydratase enzyme comprises the amino acid sequence of SEQ ID NO:6 and is encoded by a aroQ gene which comprises the polynucleotide SEQ ID NO:5 (Chaudhuri, S., Duncan, K. and Coggins, J. R., Methods Enzymol. (1987) 142:320–324);
4. Shikimate dehydrogenase enzyme comprises the amino acid sequence of SEQ ID NO:8 and is encoded by a aroE gene which comprises the polynucleotide SEQ ID NO:7 (Chaudhuri, S., Anton, I. A. and Coggins, J. R., Methods Enzymol. (1987) 142:315–320);
5. 5-enolpyruvyl shikimate 3-phosphate synthase enzyme comprises the amino acid sequence of SEQ ID NO:10 and is encoded by a aroA gene comprising SEQ ID NO:9 (Lewendon, A. and Coggins, J. R., Biochem. J. (1983) 213:187–191);
6. Chorismate synthase enzyme comprises the amino acid sequence of SEQ ID NO:12 and is encoded by a aroC gene comprising SEQ ID NO:11 (White, P. J., Millar, G. and Coggins, J. R., Biochem. J. (1988) 251:313–322);
7. Chorismate mutase—prephenate dehydrogenase enzyme comprises the amino acid sequence of SEQ ID NO:14 and is encoded by a tyrA gene comprising SEQ ID NO:13 (Davidson, B. E. and Hudson, G. S., Methods Enzymol. (1987) 142:440–450);
8. Anthranilate synthase, component I enzyme comprises the amino acid sequence of SEQ ID NO:16 and is encoded by a trpE gene comprising SEQ ID NO:15 (Bauerle, R., Hess, J. and French, S., Methods Enzymol. (1987) 142: 366–386);
9. Anthranilate synthase, component II enzyme comprises the amino acid sequence of SEQ ID NO:18 and is encoded by a trpG gene comprising SEQ ID NO:17 (Bauerle, R., Hess, J. and French, S., Methods Enzymol. (1987) 142: 366–386);
10. anthranilate phosphoribosyl transferase enzyme comprises the amino acid sequence of SEQ ID NO:20 and is encoded by a trpD gene comprising SEQ ID NO:19 (Hommel, U., Lustig, A. and Kirschner, K., Eur. J. Biochem. (1989) 180:33–40);
11. Phosphoribosyl anthranilate isomerase enzyme comprises the amino acid sequence of SEQ ID NO:22 and is encoded by a trpF gene comprising SEQ ID NO:21 (Hoch, S. O., J. Bacteriol (1979) 139:362–368);

12. Indole-3-glycerol phosphate synthase enzyme comprises the amino acid sequence of SEQ ID NO:24 and is encoded by a trpc gene comprising SEQ ID NO:23 (Hoch, S. O., J. Bacteriol (1979) 139:362–368);

13. Tryptophan synthase, B protein comprises the amino acid sequence of SEQ ID NO:26 and is encoded by a trpB gene comprising SEQ ID NO:25 (Miles, E. W., Bauerle, R. and Ahmed, S. A., Methods Enzymol 1987 (142) 398–414);

14. Tryptophan synthase, A protein comprises the amino acid sequence of SEQ ID NO:28 and is encoded by a trpA gene comprising SEQ ID NO:27 (Miles, E. W., Bauerle, R. and Ahmed, S. A., Methods Enzymol 1987 (142) 398–414);

15. Pyruvate carboxylase A-subunit comprises the amino acid sequence of SEQ ID NO:30 and is encoded by a pycA gene comprising SEQ ID NO:29 (Mukhopadhyay, B. et. al., Arch. Microbiol. (2000) 174:406–414);

16. Pyruvate carboxylase B-subunit enzyme comprises the amino acid sequence of SEQ ID NO:32 and is encoded by a pycB gene comprising SEQ ID NO:31 (Mukhopadhyay, B. et. al., Arch. Microbiol. (2000) 174:406–414);

17. Phosphoenolpyruvate carboxylase enzyme comprises the amino acid sequence of SEQ ID NO:34 and is encoded by a ppc gene comprising SEQ ID NO:33 (O'Regan, M. et. al. Gene (1989) 77:237–251);

18. Aspartate aminotransferase 1 enzyme comprises the amino acid sequence of SEQ ID NO:36 and is encoded by a aat1 gene comprising SEQ ID NO:35 (Sung, M. H. et. al. J. Bacteriol. (1990) 172:1345–1351);

19. Aspartate aminotransferase 2 enzyme comprises the amino acid sequence of SEQ ID NO:38 and is encoded by a aat2 gene comprising SEQ ID NO:37 (Sung, M. H. et. al. J. Bacteriol. (1990) 172:1345–1351);

20. Tetrahydrodipicolinate succinylase enzyme comprises the amino acid sequence of SEQ ID NO:40 and is encoded by a dapD gene comprising SEQ ID NO:39 (Richaud, C. et. al., J. Biol. Chem. (1984) 259:14824–14828);

21. Succinyl diaminopimelate aminotransferase enzyme comprises the amino acid sequence of SEQ ID NO:42 and is encoded by a dapC gene comprising SEQ ID NO:41 (Fuchs, T. M. et. al., J. Bacteriol. (2000) 182:3626–3631);

22. Succinyldiaminopimelate desuccinylase enzyme comprises the amino acid sequence of SEQ ID NO:44 and is encoded by a dapE gene comprising SEQ ID NO:43 (Bouvier, J. et. al., J. Bacteriol. (1992) 174:5265–71);

23. Diaminopimelate epimerase enzyme comprises the amino acid sequence of SEQ ID NO:46 and is encoded by a dapF gene comprising SEQ ID NO:45 (Richaud, C., Higgins, W., Mengin-Lecreulx, D. and Stragier, P., J. Bacteriol. (1987) 169:1454–1459);

24. Homoserine O-acetyltransferase enzyme comprises the amino acid sequence of SEQ ID NO:48 and is encoded by a metX gene comprising SEQ ID NO:47 (Yamagata, S., J. Bacteriol (1987) 169:3458–3463);

25. O-acetylhomoserine sulfhydrylase enzyme comprises the amino acid sequence of SEQ ID NO:50 and is encoded by a metY gene comprising SEQ ID NO:49 (Ozaki, H. and Shiio, I., J. Biochem. (1982) 91:1163–1171);

26. Homoserine kinase enzyme comprises the amino acid sequence of SEQ ID NO:52 and is encoded by a thrB gene comprising SEQ ID NO:51 (Huo, X. and Viola, R. E., Arch. Biochem. Biophys. (1996) 330:373–379);

27. Threonine synthase enzyme comprises the amino acid sequence of SEQ ID NO:54 and is encoded by a thrC gene comprising SEQ ID NO:53 (Malumbres, M., Mateos, L. M., Lumbreras, M. A., Guerrero, C. and Martin, J. F., Appl. Environ. Microbiol. (1994) 60:2209–2219).

The terms "stringent conditions" or "stringent hybridization conditions" includes reference to conditions under which a polynucleotide will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing).

Typically, stringent conditions will be those in which the salt concentration is less than approximately 1.5 M Na ion, typically about 0.01 to 1.0 M Na ion (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions also may be achieved with the addition of destabilizing agents such as formamide. Exemplary low stringency conditions include hybridization with a buffer solution of 30 to 35% formamide, 1 M NaCl, 1% SDS (w/v; sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the Tm can be approximated from the equation of Meinkoth and Wahl (Anal. Biochem., 138:267–284, 1984): Tm=81.5° C.+16.6 (log M)+0.41 (% GC)–0.61 (% form)–500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with approximately 90% identity are sought, the Tm can be decreased 10° C.

Generally, stringent conditions are selected to be about 5° C. lower than the thermal melting point (Tm) for the specific sequence and its complement at a defined ionic strength and pH. However, severely stringent conditions can utilize hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution), it is preferred to increase the SSC concentration so that a higher temperature can be used. An extensive guide to the hybridization of nucleic acids is found in Tijssen, Laboratory Techniques in Biochemistry and Molecular Biology-Hybridization with Nucleic Acid Probes, Part I, Chapter 2 "Overview of principles of hybridization and the strategy of nucleic acid probe assays", Elsevier, N.Y. (1993); and Current Protocols in Molecular Biology, Chapter 2, Ausubel, et al., Eds., Greene Publishing and Wiley-Interscience, New York (1995).

Stringent hybridization conditions are understood to mean those conditions where hybridization, either in solution or on a solid support, occur between two polynucleotide molecules which are 70% to 100% homologous in nucleotide sequence which include 75%, 80%, 85%, 90%, 95%, 98% and all values and subranges therebetween.

Homology, sequence similarity or sequence identity of nucleotide or amino acid sequences may be determined conventionally by using known software or computer programs. To find the best segment of identity or similarity of sequences, BLAST (Altschul et al (1990) J. Mol. Biol. 215:403–410 and Lipman et al (1990) J. Mol. Biol. 215: 403–410), FASTA (Lipman et al (1985) Science 227:1435–1441), or Smith and Waterman (Smith and Waterman (1981) J. Mol. Biol. 147:195–197) homology search programs can be used. To perform global alignments, sequence alignment programs such as the CLUSTAL W (Thompson et al (1994) Nucleic Acids Research 22:4673–4680) can be used.

The present invention also provides processes for preparing amino acids using bacteria that comprise at least one polynucleotide whose expression is enhanced or attenuated. Likewise, the invention also provides processes for preparing amino acids using bacteria that comprise at least on polypeptide whose activity is enhanced or attenuated. Preferably, a bacterial cell with enhanced or attenuated expression of one or more of the polypeptides and/or polynucleotides described herein will improve amino acid yield at least 1% compared to a bacterial strain not having the enhanced or attenuated expression. For the production of amino acids the *M. methylotrophus* polynucleotides described herein may be used to target expression, either by disruption to turn off or increase or enhance the expression or relative activity of the polypeptide enzymes encoded therein.

The term "enhancement" as used herein means increasing intracellular activity of one or more polypeptides in the bacterial cell, which in turn are encoded by the corresponding polynucleotides described herein. To facilitate such an increase, the copy number of the genes corresponding to the polynucleotides described herein may be increased. Alternatively, a strong and/or inducible promoter may be used to direct the expression of the polynucleotide, the polynucleotide being expressed either as a transient expression vehicle or homologously or heterologously incorporated into the bacterial genome. In another embodiment, the promoter, regulatory region and/or the ribosome binding site upstream of the gene can be altered to achieve the over-expression. The expression may also be enhanced by increasing the relative half-life of the messenger RNA.

In another embodiment, the enzymatic activity of the polypeptide itself may be increased by employing one or more mutations in the polypeptide amino acid sequence, which increases the activity. For example, altering the relative Km of the polypeptide with its corresponding substrate will result in enhanced activity. Likewise, the relative half-life of the polypeptide may be increased.

In either scenario, that being enhanced gene expression or enhanced enzymatic activity, the enhancement may be achieved by altering the composition of the cell culture media and/or methods used for culturing.

"Enhanced expression" or "enhanced activity" as used herein means an increase of at least 10%, 25%, 50%, 75%, 100%, 150%, 200%, 300%, 400% or 500% compared to a wild-type protein, polynucleotide, gene; or the activity and/or the concentration of the protein present before the polynucleotides or polypeptides are enhanced.

The term "attenuation" as used herein means a reduction or elimination of the intracellular activity of the polypeptides in a bacterial cell that are encoded by the corresponding polynucleotide. To facilitate such a reduction or elimination, the copy number of the genes corresponding to the polynucleotides described herein may be decreased or removed. Alternatively, a weak and/or inducible promoter may used to direct the expression of the polynucleotide, the polynucleotide being expressed either as a transient expression vehicle or homologously or heterologously incorporated into the bacterial genome. For example, the endogenous promoter or regulatory region of the gene corresponding to the isolated polynucleotides described herein may be replaced with the aforementioned weak and/or inducible promoter. Alternatively, the promoter or regulatory region may be removed. The expression may also be attenuated by decreasing the relative half-life of the messenger RNA.

In another embodiment, the enzymatic activity of the polypeptide itself may be decreased or deleted by employing one or more mutations in the polypeptide amino acid sequence, which decreases the activity or removes any detectable activity. For example, altering the relative Kd of the polypeptide with its corresponding substrate will result in attenuated activity. Likewise, a decrease in the relative half-life of the polypeptide will result in attenuated activity.

By attenuation measures, the activity or concentration of the corresponding protein is in general reduced to 0 to 75%, 0 to 50%, 0 to 25%, 0 to 10% or 0 to 5% of the activity or concentration of the wild-type protein or of the activity or concentration of the protein in the starting microorganism.

Suitable vectors for carrying *M. methylotrophus* polynucleotides include those vectors which can direct expression of the gene in bacterial cells as known in the art. One embodiment of the present invention is whereby the vectors contain an inducible or otherwise regulated expression system whereby the *M. methylotrophus* polynucleotides may be expressed under certain conditions and not expressed under other conditions. Furthermore, in another embodiment of the invention, the *M. methylotrophus* polynucleotides can be constitutively expressed. Examples of such vectors and suitable cells in which they can be introduced are described in Sambrook et al., Molecular Cloning: A Laboratory Manual, 3rd Ed., Cold Spring Harbor Laboratory Press, Cold Spring Harbor, N.Y. (2001) and Current Protocols in Molecular Biology, Ausebel et al, (Eds.), John Wiley and Sons, Inc., New York, 2000.

Methods of introducing *M. methylotrophus* polynucleotides or vectors containing the *M. methylotrophus* polynucleotides include electroporation, conjugation, calcium-mediated transfection, infection with bacteriophage and other methods known in the art. These and other methods are described in Sambrook et al., Molecular Cloning: A Laboratory Manual, 3rd Ed., Cold Spring Harbor Laboratory Press, Cold Spring Harbor, N.Y. (2001) and Current Protocols in Molecular Biology, Ausebel et al, (Eds.), John Wiley and Sons, Inc., New York (2000).

The microorganisms that can be used in the present invention should have the ability to produce amino acids, preferably L-amino acids, from a suitable carbon source, preferably carbon sources such as methanol, glucose, sucrose, lactose, fructose, maltose, molasses, starch, cellulose glycerol or ethanol. The microorganisms can be *Methylophilus* bacteria, preferably *Methylophilus methylotrophus*.

Suitable culture conditions for the growth and/or production of *M. methylotrophus* polynucleotides are dependent on the cell type used. Likewise, culturing cells that contain attenuated or enhanced expression of the *M. methylotrophus* polynucleotides or polypeptides, as described herein, may be cultured in accordance with methods known in the art. Examples of culture conditions for various cells is described in Sambrook et al., Molecular Cloning: A Laboratory Manual, 3rd Ed., Cold Spring Harbor Laboratory Press, Cold Spring Harbor, N.Y. (2001); Current Protocols in Molecular Biology, Ausebel et al, (Eds.), John Wiley and Sons, Inc., 2000; and Cells: A Laboratory Manual (Vols. 1–3), Spector et al, (Eds.), Cold Spring Harbor Laboratory Press, Cold Spring Harbor, N.Y., (1988).

Following culturing the polypeptide or protein products, which are encoded by the *M. methylotrophus* polynucleotides, may be purified using known methods of protein purification. These methods include high performance liquid chromatography (HPLC), ion-exchange chromatography, size exclusion chromatography; affinity separations using materials such as beads with exposed heparin, metals, or lipids; or other approaches known to those skilled in the art. These and other methods of protein purification are disclosed in Sambrook et al., Molecular Cloning: A Laboratory Manual, 3rd Ed., Cold Spring Harbor Laboratory Press, Cold Spring Harbor, N.Y. (2001); Current Protocols in Molecular Biology, Ausebel et al, eds., John Wiley and Sons, Inc., 2000 and Protein Purification, Scopes and Cantor, (Eds.), Springer-Verlag, (1994). Likewise, the amino acids produced may be purified by methods known in the art using similar chromatography devices.

The invention also provides antibodies that bind to the polypeptides of the present invention. Antibodies binding to the polypeptides can be either monoclonal or polyclonal, preferably the antibodies are monoclonal. Methods for obtaining antibodies that bind to the polypeptides are known in the art and are described, for example, in Harlow and Lane, Antibodies: A Laboratory Manual, Cold Spring Harbor Laboratory Press, Cold Spring Harbor, N.Y. (1988).

Having generally described this invention, a further understanding can be obtained by reference to certain specific examples which are provided herein for purposes of illustration only, and are not intended to be limiting unless otherwise specified.

EXAMPLES

Whole genome sequencing using random shotgun method is described in Fleischman R. D. et. al. (1995) Science, 269: 496–512.

Example 1

Construction of Genomic Libraries of *Methylophilus methylotrophus*

*M. methylotrophus* AS1 was cultured at 30° C. in the 121 medium described in the Catalogue of Strains (The National Collections of Industrial and Marine Bacteria Ltd., 1994). Cells were collected by centrifugation. Genomic DNA was isolated using the Genome-tip system (Qiagen K. K., Tokyo, Japan). The genomic DNA was sheared and fragmentized by sonication. The resultant fragments in the 1- to 2-kb size range were purified by gel electrophoresis through 1% low-melting agarose gel, followed by recovery using the Wizard DNA purification kit (Promega KK, Tokyo, Japan). The recovered fragments were ligated to the high-copy number vector pUC118 treated by HincII and bacterial alkaline phosphatase (Takara Shuzo, Kyoto, Japan), and this was designated pUC118 library.

For larger fragments (9- to 11-kb in size), the genomic DNA was partially digested by restriction endonuclease Sau3AI, followed by 0.6% agarose gel electrophoresis. The DNA fragments corresponding 9-kb to 11-kb in size were excised from gel and were recovered using the DNACELL (Daiichi Pure Chemicals, Tokyo, Japan). The recovered fragments were ligated into the low-coy number vector pMW118 (Nippon Gene, Toyama, Japan), which is a derivative of the pSC101 (Bernaidi, A. and Bernardi, F. (1984) Nucleic Acids Res. 12, 9415–4426). This library composed of large DNA fragments was designated pMW118 library.

General DNA manipulation was performed according to previously described methods (Sambrook. et. al. (1989) "Molecular Cloning: A Laboratory Manual/Second Edition", Cold Spring Harbor Laboratory Press).

Example 2

DNA Sequencing and Sequence Assembly

The pUC118 library were transformed into *Escherichia coli* DH5α and plated on Luria-Bertani medium containing 100 μg/ml ampicillin and 40 μg/ml 5-bromo-4-chloro-3indolyl-α-D-galactoside (X-Gal). The white colonies were picked up and cultured in Luria-Bertani medium containing 100 μg/ml ampicillin. The individual colony was cultured in the well of the 96 deep-well plates, and the plasmids were isolated using QIAprep Turbo Kit (Qiagen). The DNA fragments inserted into pUC118 were sequenced using a M13 reverse primer. The shotgun sequencing was performed with the BigDye terminators and 3700 DNA analyzer (Applied Biosystems Japan, Tokyo, Japan). Approximately 50,000 samples from pUC118 library corresponding to coverage of approximately 8-fold to the genome size were analyzed and the sequences were assembled by Phred/Phrap software (CodonCode, MA, USA). This assembly treatment yielded 60 contigs with more than 5 kb in size.

As for pMW118 library, 2,000 clones corresponding to coverage of approximately 5-fold were sequenced using both M13 forward and reverse primers. The end-sequence data were analyzed and the linking clones between contigs were selected from pMW118 library. The inserted fragments of selected clones were amplified by the polymerase chain reaction (PCR) using LA Taq polymerase (Takara Shuzo) and *M. methylotrophus* genomic DNA as a template. These products of PCR were entirely sequenced as described in Example 1, and the gap DNA sequences between contigs were determined. By the additional sequence information, the Phrap assembly software reduced the number of contigs with more than 5 kb in size to 24. Then the 48 DNA primers with sequences complementary to the end-sequences of the 24 contigs were prepared. All possible pairwise combination of the primers were tested by PCR to amplify the DNA fragments of *M. methylotrophus* genomic DNA. The amplified products were sequenced directly. In several cases, the additional primers complementary to different sequences at the end of the contig were used. This strategy could close all of the remaining physical gaps and resulted in a single circular contig. Several regions that had been sequenced in only one direction and had postulated secondary structure were confirmed. By this research, the genome of *M. methylotrophus* was found to be a single circular with the size of 2,869,603 bases and GC content of 49.6%.

Example 3

Sequence Analysis and Annotation

Sequence analysis and annotation was managed using the Genome Gambler software (Sakiyama, T. et. al. (2000) Biosci. Biotechnol. Biochem. 64: 670–673). All open reading frames of more than 150 bp in length were extracted and the translated amino acid sequences were searched against non-redundant protein sequences in GenBank using the BLAST program (Altschul, S. F. et. al. (1990) J. Mol. Biol. 215, 403–410). Of putative polynucleotide encoding sequences with significant similarities to the sequences in public databases (BLASTP scores of more than 100), the genes involved in biosynthesis of amino acids were selected. Start codons (AUG or GUG) were putatively identified by similarity of the genes and their proximity to the ribosome binding sequences (Shine, J. and Dalgarno, L. (1975) Eur. J. Biochem. 57: 221–230). Careful assignment of gene function resulted in the identification of aromatic amino acid biosynthetic genes, the shikimate kinase gene (aroK), the 3-dehydroquinate synthase gene (aroB), the 3-dehydroquinate dehydratase gene (aroC), the shikimate dehydrogenase gene (aroE), the 5-enolpyruvyl shikimate 3-phosphate synthase gene (aroA), the chorismate synthase gene (aroC), the chorismate mutase-prephenate dehydrogenase gene (tyrA), the anthranilate synthase, component I gene (trpE), the anthranilate synthase, component II gene (trpG), the anthranilate phosphoribosyl transferase gene (trpD), the phosphoribosyl anthranilate isomerase gene (trpF), the indole-3-glycerol phosphate synthase gene (trpC), the tryptophan synthase, B protein gene (trpB), and the tryptophan synthase, A protein gene (trpA). The pyruvate carboxylase A-subunit gene (pycA) and the pyruvate carboxylase B-subunit gene (pycB) were found probably in operon. The phosphoenolpyruvate carboxylase gene (ppc) and the aspaatate amino acid biosynthetic genes, the two aspartate aminotransferase genes (aat1 and aat2), the tetrahydrodipicolinate succinylase gene (dapD), the succinyl diaminopimelate aminotransferase gene (dapC), the succinyl-diaminopimelate desuccinylase gene (dapE), the diaminopimelate epimerase gene (dapF), the homoserine O-acetyltransferase gene (metX), the O-acetylhomoserine sulfhydrylase gene (metY), the homoserine kinase gene (thrB), and the threonine synthase gene (thrC) were identified.

Obviously, numerous modifications and variations on the present invention are possible in light of the above teachings. It is therefore to be understood that within the scope of the appended claims, the invention may be practiced otherwise than as specifically described herein.

What is claimed is:

1. An isolated polynucleotide encoding a protein comprising the amino acid sequence of SEQ ID NO:2.

2. A vector comprising the isolated polynucleotide of claim 1.

3. A host cell comprising the isolated polynucleotide of claim 1.

4. The host cell of claim 3, which is a *Methylophilus* bacterium.

5. The host cell of claim 4, which is a *Methylophilus methylotrophus* bacterium.

6. A method of making a protein comprising:
culturing the host cell of claim 3 for a time and under conditions suitable for expression of the protein; and
collecting said protein.

7. An isolated polynucleotide comprising the nucleotide sequence of SEQ ID NO:1.

8. A vector comprising the isolated polynucleotide of claim 7.

9. A host cell comprising the isolated polynucleotide of claim 7.

10. The host cell of claim 9, which is a *Methylophilus* bacterium.

11. The host cell of claim 10, which is a *Methylophilus methylotrophus* bacterium.

12. A method for making a protein comprising:
culturing the host cell of claim 9 for a time and under conditions suitable for the expression of the polynucleotide to produce a protein; and
collecting said protein.

13. An isolated polynucleotide, which hybridizes under high stringent conditions tote isolated polynucleotide of claim 7, wherein said high stringent conditions are hybridization in 50% formamide, 1 M NaCl, 1% SDS at 37° C., and a wash in 0.1×SSC at 60° C. to 65° C., and wherein said polynucleotide encodes a protein having shikimate kinase enzyme activity.

14. A vector comprising the isolated polynucleotide of claim 13.

15. A host cell comprising the isolated polynucleotide of claim 13.

16. A method of making a protein comprising:
culturing the host cell of claim 15 for a time and under conditions suitable for the expression of the polynucleotide to produce a protein; and
collecting said protein.

17. An isolated polynucleotide, which is at least 95% identical to the polynucleotide of claim 7, and wherein said polynucleotide encodes a protein having shikimate kinase enzyme activity.

18. A vector comprising the isolated polynucleotide of claim 17.

19. A host cell comprising the isolated polynucleotide of claim 17.

20. A method of making a protein comprising:
culturing the host cell of claim 19 for a time and under conditions suitable for the expression of the polynucleotide to produce a protein; and
collecting said protein.

* * * * *

SEQUENCE LISTING

<160> NUMBER OF SEQ ID NOS: 54

<210> SEQ ID NO 1
<211> LENGTH: 543
<212> TYPE: DNA
<213> ORGANISM: Methylophilus methylotrophus
<220> FEATURE:
<221> NAME/KEY: CDS
<222> LOCATION: (1)..(543)
<223> OTHER INFORMATION:

<400> SEQUENCE: 1

| atg | ggt | gcg | caa | ata | cca | aac | aac | att | ttt | ttg | atc | gga | ttg | atg | gga | 48 |
| Met | Gly | Ala | Gln | Ile | Pro | Asn | Asn | Ile | Phe | Leu | Ile | Gly | Leu | Met | Gly | |
| 1 | | | | 5 | | | | | 10 | | | | | 15 | | |

| gcg | ggc | aag | acc | acc | gtt | ggc | aaa | ttg | atc | gcc | aag | aat | tta | ggc | aag | 96 |
| Ala | Gly | Lys | Thr | Thr | Val | Gly | Lys | Leu | Ile | Ala | Lys | Asn | Leu | Gly | Lys | |
| | | | 20 | | | | | 25 | | | | | 30 | | | |

| acc | ttt | tac | gat | acc | gat | cat | gtg | att | gag | cag | cgg | act | ggc | gtc | aag | 144 |
| Thr | Phe | Tyr | Asp | Thr | Asp | His | Val | Ile | Glu | Gln | Arg | Thr | Gly | Val | Lys | |
| | | 35 | | | | | 40 | | | | | 45 | | | | |

| atc | ccg | acc | att | ttt | gag | ctg | gaa | ggc | gaa | gcg | ggg | ttt | cgc | aag | cgt | 192 |
| Ile | Pro | Thr | Ile | Phe | Glu | Leu | Glu | Gly | Glu | Ala | Gly | Phe | Arg | Lys | Arg | |
| | 50 | | | | | 55 | | | | | 60 | | | | | |

| gaa | acg | tct | acg | ctg | gaa | gag | ctg | gca | cag | cag | gat | aat | att | gtc | ctg | 240 |
| Glu | Thr | Ser | Thr | Leu | Glu | Glu | Leu | Ala | Gln | Gln | Asp | Asn | Ile | Val | Leu | |
| 65 | | | | | 70 | | | | | 75 | | | | | 80 | |

| gcc | acg | ggt | ggt | ggt | gcc | atc | atc | gct | cct | gaa | aac | cgg | gaa | ata | ctc | 288 |
| Ala | Thr | Gly | Gly | Gly | Ala | Ile | Ile | Ala | Pro | Glu | Asn | Arg | Glu | Ile | Leu | |
| | | | | 85 | | | | | 90 | | | | | 95 | | |

| aag | aaa | tat | ggc | tat | gtg | att | tac | ctg | cgg | gca | aat | gtg | aat | gag | ctg | 336 |

```
Lys Lys Tyr Gly Tyr Val Ile Tyr Leu Arg Ala Asn Val Asn Glu Leu
            100                 105                 110 tat ctg cgt acc cgc aat gat aaa aat cgt ccc ttg ttg cag aat gta        384
Tyr Leu Arg Thr Arg Asn Asp Lys Asn Arg Pro Leu Leu Gln Asn Val
            115                 120                 125 gat gtc aaa gcc agg ctg gaa caa ttg ttc cat gcg cgc aat cca ctt        432
Asp Val Lys Ala Arg Leu Glu Gln Leu Phe His Ala Arg Asn Pro Leu
130                 135                 140 tat acc gaa acc gca aac ctc att gtg gat acc ggg cat cag ccg gta        480
Tyr Thr Glu Thr Ala Asn Leu Ile Val Asp Thr Gly His Gln Pro Val
145                 150                 155                 160 gcg gtc att atc cag aaa att gaa aac gcc ctg aaa gcg ttg gag tca        528
Ala Val Ile Ile Gln Lys Ile Glu Asn Ala Leu Lys Ala Leu Glu Ser
                165                 170                 175 tca tgc aaa cct tga                                                    543
Ser Cys Lys Pro
            180

<210> SEQ ID NO 2
<211> LENGTH: 180
<212> TYPE: PRT
<213> ORGANISM: Methylophilus methylotrophus

<400> SEQUENCE: 2

Met Gly Ala Gln Ile Pro Asn Asn Ile Phe Leu Ile Gly Leu Met Gly
1               5                   10                  15

Ala Gly Lys Thr Thr Val Gly Lys Leu Ile Ala Lys Asn Leu Gly Lys
            20                  25                  30

Thr Phe Tyr Asp Thr Asp His Val Ile Glu Gln Arg Thr Gly Val Lys
        35                  40                  45

Ile Pro Thr Ile Phe Glu Leu Glu Gly Glu Ala Gly Phe Arg Lys Arg
    50                  55                  60

Glu Thr Ser Thr Leu Glu Glu Leu Ala Gln Gln Asp Asn Ile Val Leu
65                  70                  75                  80

Ala Thr Gly Gly Gly Ala Ile Ile Ala Pro Glu Asn Arg Glu Ile Leu
                85                  90                  95

Lys Lys Tyr Gly Tyr Val Ile Tyr Leu Arg Ala Asn Val Asn Glu Leu
            100                 105                 110

Tyr Leu Arg Thr Arg Asn Asp Lys Asn Arg Pro Leu Leu Gln Asn Val
            115                 120                 125

Asp Val Lys Ala Arg Leu Glu Gln Leu Phe His Ala Arg Asn Pro Leu
130                 135                 140

Tyr Thr Glu Thr Ala Asn Leu Ile Val Asp Thr Gly His Gln Pro Val
145                 150                 155                 160

Ala Val Ile Ile Gln Lys Ile Glu Asn Ala Leu Lys Ala Leu Glu Ser
                165                 170                 175

Ser Cys Lys Pro
            180

<210> SEQ ID NO 3
<211> LENGTH: 1080
<212> TYPE: DNA
<213> ORGANISM: Methylophilus methylotrophus
<220> FEATURE:
<221> NAME/KEY: CDS
<222> LOCATION: (1)..(1080)
<223> OTHER INFORMATION:

<400> SEQUENCE: 3
```

```
atg caa acc ttg acc gtc agc ctg gct gac cgt agc tat cct att cat      48
Met Gln Thr Leu Thr Val Ser Leu Ala Asp Arg Ser Tyr Pro Ile His
1               5                   10                  15 atc ggc aat aac ctg cta gga cag gcc aac ctg att ttg cca cat cta      96
Ile Gly Asn Asn Leu Leu Gly Gln Ala Asn Leu Ile Leu Pro His Leu
            20                  25                  30 aag cgt aaa caa gtg gcg att gtc agc aac acc act gtc gct cct tta     144
Lys Arg Lys Gln Val Ala Ile Val Ser Asn Thr Thr Val Ala Pro Leu
        35                  40                  45 tat atg cag gcc att gca aag cct tta cgc gac gct ggt gtc agt gtc     192
Tyr Met Gln Ala Ile Ala Lys Pro Leu Arg Asp Ala Gly Val Ser Val
    50                  55                  60 att gag att att ctg ccg gat ggc gag gct tac aaa aac aac gaa acc     240
Ile Glu Ile Ile Leu Pro Asp Gly Glu Ala Tyr Lys Asn Asn Glu Thr
65                  70                  75                  80 ctg caa acc att tac gat cat ttg ctg caa aac cgt tgt gaa cgt aac     288
Leu Gln Thr Ile Tyr Asp His Leu Leu Gln Asn Arg Cys Glu Arg Asn
                85                  90                  95 acg acc ctg att gca cta ggc ggc ggt gtg att ggt gac ctc act ggg     336
Thr Thr Leu Ile Ala Leu Gly Gly Gly Val Ile Gly Asp Leu Thr Gly
            100                 105                 110 tat gcg gcg gcg act tat ctg cgc ggc gtg ccg ttt att cag gtg ccc     384
Tyr Ala Ala Ala Thr Tyr Leu Arg Gly Val Pro Phe Ile Gln Val Pro
        115                 120                 125 acc act tta ttg tcg cag gtg gat tcc agc gtg ggc ggt aaa aca ggt     432
Thr Thr Leu Leu Ser Gln Val Asp Ser Ser Val Gly Gly Lys Thr Gly
    130                 135                 140 atc aat cac ccg ctg ggc aag aac atg ata ggt gcc ttt tac cag cct     480
Ile Asn His Pro Leu Gly Lys Asn Met Ile Gly Ala Phe Tyr Gln Pro
145                 150                 155                 160 aaa ctg gtg ttg gca gat atc gat acc ttg aaa act ctg cca caa cgg     528
Lys Leu Val Leu Ala Asp Ile Asp Thr Leu Lys Thr Leu Pro Gln Arg
                165                 170                 175 gaa ttg tct gca ggt atc gcc gaa gtc atc aaa tat ggc ctg att cgc     576
Glu Leu Ser Ala Gly Ile Ala Glu Val Ile Lys Tyr Gly Leu Ile Arg
            180                 185                 190 gat gct gat ttt ttt gag tgg ctg gaa atc aat atg tcc gca ctg atg     624
Asp Ala Asp Phe Phe Glu Trp Leu Glu Ile Asn Met Ser Ala Leu Met
        195                 200                 205 gcg ctg gat gcc gca gta gcc agt tat gcc att tac cgc tcg tgt cag     672
Ala Leu Asp Ala Ala Val Ala Ser Tyr Ala Ile Tyr Arg Ser Cys Gln
    210                 215                 220 aac aag gca gag gta gta gcc gct gat gag cac gaa cag ggt gag cgt     720
Asn Lys Ala Glu Val Val Ala Ala Asp Glu His Glu Gln Gly Glu Arg
225                 230                 235                 240 gcc ttg ctg aat tta ggc cac act ttt ggt cat gcg att gaa aat gcc     768
Ala Leu Leu Asn Leu Gly His Thr Phe Gly His Ala Ile Glu Asn Ala
                245                 250                 255 atg ggt tat ggt gtc tgg ttg cac ggc gaa gct gtg gca acc ggt acc     816
Met Gly Tyr Gly Val Trp Leu His Gly Glu Ala Val Ala Thr Gly Thr
            260                 265                 270 gtg atg gcc gca gat ttg tcg caa cgt atg ggt tgg ctg aat gat gcg     864
Val Met Ala Ala Asp Leu Ser Gln Arg Met Gly Trp Leu Asn Asp Ala
        275                 280                 285 caa att gca cgt att aaa acc att atg caa gca gcc aaa tta cct ata     912
Gln Ile Ala Arg Ile Lys Thr Ile Met Gln Ala Ala Lys Leu Pro Ile
    290                 295                 300 aaa gca cca gat ttg ggt gtg gag gag tat ttg cgg ctc atg caa ctg     960
Lys Ala Pro Asp Leu Gly Val Glu Glu Tyr Leu Arg Leu Met Gln Leu
305                 310                 315                 320
```

```
gat aag aag gtt gct gat gga cgt atc cgc ctt att ctg caa cag gac    1008
Asp Lys Lys Val Ala Asp Gly Arg Ile Arg Leu Ile Leu Gln Gln Asp
            325                 330                 335 att ggc aag gca gtg atc acg gca gat tat gat gat gat aag tta aag    1056
Ile Gly Lys Ala Val Ile Thr Ala Asp Tyr Asp Asp Asp Lys Leu Lys
        340                 345                 350 cag acg ctg tca ctg gcg gca taa                                    1080
Gln Thr Leu Ser Leu Ala Ala
            355
```

<210> SEQ ID NO 4
<211> LENGTH: 359
<212> TYPE: PRT
<213> ORGANISM: Methylophilus methylotrophus

<400> SEQUENCE: 4

```
Met Gln Thr Leu Thr Val Ser Leu Ala Asp Arg Ser Tyr Pro Ile His
1               5                   10                  15

Ile Gly Asn Asn Leu Leu Gly Gln Ala Asn Leu Ile Leu Pro His Leu
            20                  25                  30

Lys Arg Lys Gln Val Ala Ile Val Ser Asn Thr Thr Val Ala Pro Leu
        35                  40                  45

Tyr Met Gln Ala Ile Ala Lys Pro Leu Arg Asp Ala Gly Val Ser Val
    50                  55                  60

Ile Glu Ile Ile Leu Pro Asp Gly Glu Ala Tyr Lys Asn Asn Glu Thr
65                  70                  75                  80

Leu Gln Thr Ile Tyr Asp His Leu Leu Gln Asn Arg Cys Glu Arg Asn
                85                  90                  95

Thr Thr Leu Ile Ala Leu Gly Gly Gly Val Ile Gly Asp Leu Thr Gly
            100                 105                 110

Tyr Ala Ala Ala Thr Tyr Leu Arg Gly Val Pro Phe Ile Gln Val Pro
        115                 120                 125

Thr Thr Leu Leu Ser Gln Val Asp Ser Ser Val Gly Gly Lys Thr Gly
    130                 135                 140

Ile Asn His Pro Leu Gly Lys Asn Met Ile Gly Ala Phe Tyr Gln Pro
145                 150                 155                 160

Lys Leu Val Leu Ala Asp Ile Asp Thr Leu Lys Thr Leu Pro Gln Arg
                165                 170                 175

Glu Leu Ser Ala Gly Ile Ala Glu Val Ile Lys Tyr Gly Leu Ile Arg
            180                 185                 190

Asp Ala Asp Phe Phe Glu Trp Leu Glu Ile Asn Met Ser Ala Leu Met
        195                 200                 205

Ala Leu Asp Ala Ala Val Ala Ser Tyr Ala Ile Tyr Arg Ser Cys Gln
    210                 215                 220

Asn Lys Ala Glu Val Val Ala Ala Asp Glu His Glu Gln Gly Glu Arg
225                 230                 235                 240

Ala Leu Leu Asn Leu Gly His Thr Phe Gly His Ala Ile Glu Asn Ala
                245                 250                 255

Met Gly Tyr Gly Val Trp Leu His Gly Glu Ala Val Ala Thr Gly Thr
            260                 265                 270

Val Met Ala Ala Asp Leu Ser Gln Arg Met Gly Trp Leu Asn Asp Ala
        275                 280                 285

Gln Ile Ala Arg Ile Lys Thr Ile Met Gln Ala Ala Lys Leu Pro Ile
    290                 295                 300

Lys Ala Pro Asp Leu Gly Val Glu Glu Tyr Leu Arg Leu Met Gln Leu
```

```
                305                 310                 315                 320
Asp Lys Lys Val Ala Asp Gly Arg Ile Arg Leu Ile Leu Gln Gln Asp
                    325                 330                 335
Ile Gly Lys Ala Val Ile Thr Ala Asp Tyr Asp Asp Lys Leu Lys
            340                 345                 350
Gln Thr Leu Ser Leu Ala Ala
        355

<210> SEQ ID NO 5
<211> LENGTH: 438
<212> TYPE: DNA
<213> ORGANISM: Methylophilus methylotrophus
<220> FEATURE:
<221> NAME/KEY: CDS
<222> LOCATION: (1)..(438)
<223> OTHER INFORMATION:

<400> SEQUENCE: 5 atg ggc acc aaa tcc atc ctg gtg att cac gga ccc aat tta aat atg      48
Met Gly Thr Lys Ser Ile Leu Val Ile His Gly Pro Asn Leu Asn Met
1               5                   10                  15 ctg ggc acc cga gag ccg cag cat tat ggc agc caa acg ctt gca gac      96
Leu Gly Thr Arg Glu Pro Gln His Tyr Gly Ser Gln Thr Leu Ala Asp
                20                  25                  30 atc gac caa cgt ttg caa gcc ttg gct cgt gct gat caa gtg cgt ctg     144
Ile Asp Gln Arg Leu Gln Ala Leu Ala Arg Ala Asp Gln Val Arg Leu
            35                  40                  45 gaa aca ttc cag agt aat gcc gaa gct gag atc atc gag aaa ata cat     192
Glu Thr Phe Gln Ser Asn Ala Glu Ala Glu Ile Ile Glu Lys Ile His
        50                  55                  60 gca ttg tcc gtg aat cgt gtg gat tac atc att att aat cct gcg gcg     240
Ala Leu Ser Val Asn Arg Val Asp Tyr Ile Ile Ile Asn Pro Ala Ala
65                  70                  75                  80 ttc acg cac act tct atc gct atc cgc gat gcc att tct gca gtc aag     288
Phe Thr His Thr Ser Ile Ala Ile Arg Asp Ala Ile Ser Ala Val Lys
                85                  90                  95 gtg ccg ttt att gaa gtg cat ctc tcc aat gtg cat gca cga gag tca     336
Val Pro Phe Ile Glu Val His Leu Ser Asn Val His Ala Arg Glu Ser
                100                 105                 110 ttc cgg cac cat tct tat ttc agc gat att gct acc gca gtc att tgc     384
Phe Arg His His Ser Tyr Phe Ser Asp Ile Ala Thr Ala Val Ile Cys
            115                 120                 125 ggt ttg ggc gca gag gga tat ttc gcc gct tat cgc tat atc caa caa     432
Gly Leu Gly Ala Glu Gly Tyr Phe Ala Ala Tyr Arg Tyr Ile Gln Gln
        130                 135                 140 ctc taa                                                              438
Leu
145

<210> SEQ ID NO 6
<211> LENGTH: 145
<212> TYPE: PRT
<213> ORGANISM: Methylophilus methylotrophus

<400> SEQUENCE: 6

Met Gly Thr Lys Ser Ile Leu Val Ile His Gly Pro Asn Leu Asn Met
1               5                   10                  15

Leu Gly Thr Arg Glu Pro Gln His Tyr Gly Ser Gln Thr Leu Ala Asp
                20                  25                  30

Ile Asp Gln Arg Leu Gln Ala Leu Ala Arg Ala Asp Gln Val Arg Leu
            35                  40                  45
```

```
Glu Thr Phe Gln Ser Asn Ala Glu Ala Glu Ile Ile Glu Lys Ile His
    50                  55                  60

Ala Leu Ser Val Asn Arg Val Asp Tyr Ile Ile Asn Pro Ala Ala
65                  70                  75                  80

Phe Thr His Thr Ser Ile Ala Ile Arg Asp Ala Ile Ser Ala Val Lys
                    85                  90                  95

Val Pro Phe Ile Glu Val His Leu Ser Asn Val His Ala Arg Glu Ser
                100                 105                 110

Phe Arg His His Ser Tyr Phe Ser Asp Ile Ala Thr Ala Val Ile Cys
                115                 120                 125

Gly Leu Gly Ala Glu Gly Tyr Phe Ala Ala Tyr Arg Tyr Ile Gln Gln
    130                 135                 140

Leu
145

<210> SEQ ID NO 7
<211> LENGTH: 825
<212> TYPE: DNA
<213> ORGANISM: Methylophilus methylotrophus
<220> FEATURE:
<221> NAME/KEY: CDS
<222> LOCATION: (1)..(825)
<223> OTHER INFORMATION:

<400> SEQUENCE: 7
```

| | | | | | | | | | | | | | | | | |
|---|---|---|---|---|---|---|---|---|---|---|---|---|---|---|---|---|
| atg | gcc | gtt | gaa | aaa | tac | gca | gtg | att | ggc | aat | ccg | att | gaa | cac | agc | 48 |
| Met | Ala | Val | Glu | Lys | Tyr | Ala | Val | Ile | Gly | Asn | Pro | Ile | Glu | His | Ser | |
| 1 | | | | 5 | | | | | 10 | | | | | 15 | | |
| aaa | tcg | ccg | ttg | att | cac | cag | gct | ttt | gct | aaa | cag | ttc | aat | aaa | gtg | 96 |
| Lys | Ser | Pro | Leu | Ile | His | Gln | Ala | Phe | Ala | Lys | Gln | Phe | Asn | Lys | Val | |
| | | | 20 | | | | | 25 | | | | | 30 | | | |
| att | ggt | tat | gaa | aag | gtt | ttg | gca | ccg | ctg | gat | gga | ttc | gag | gtg | acg | 144 |
| Ile | Gly | Tyr | Glu | Lys | Val | Leu | Ala | Pro | Leu | Asp | Gly | Phe | Glu | Val | Thr | |
| | | 35 | | | | | 40 | | | | | 45 | | | | |
| cta | caa | agg | ttg | cgt | gcg | gaa | ggt | tat | ttg | ggt | gcc | aat | gtg | acc | gtg | 192 |
| Leu | Gln | Arg | Leu | Arg | Ala | Glu | Gly | Tyr | Leu | Gly | Ala | Asn | Val | Thr | Val | |
| | 50 | | | | | 55 | | | | | 60 | | | | | |
| cct | ttt | aag | ttt | gag | gct | ttt | aat | gcc | tgc | cag | gaa | ttg | tct | gca | cgt | 240 |
| Pro | Phe | Lys | Phe | Glu | Ala | Phe | Asn | Ala | Cys | Gln | Glu | Leu | Ser | Ala | Arg | |
| 65 | | | | | 70 | | | | | 75 | | | | | 80 | |
| gcg | cag | gca | gct | ggt | gca | gtc | aat | acc | tta | agc | ttt | aat | aag | cag | tat | 288 |
| Ala | Gln | Ala | Ala | Gly | Ala | Val | Asn | Thr | Leu | Ser | Phe | Asn | Lys | Gln | Tyr | |
| | | | | 85 | | | | | 90 | | | | | 95 | | |
| atc | gcc | ggt | gat | aat | acc | gat | ggc | tgt | ggg | cta | gtg | aac | gac | att | ctc | 336 |
| Ile | Ala | Gly | Asp | Asn | Thr | Asp | Gly | Cys | Gly | Leu | Val | Asn | Asp | Ile | Leu | |
| | | | | 100 | | | | | 105 | | | | | 110 | | |
| cag | cat | cag | cat | acc | cta | tta | gct | gga | aaa | aaa | gtg | tta | ttg | ctt | ggg | 384 |
| Gln | His | Gln | His | Thr | Leu | Leu | Ala | Gly | Lys | Lys | Val | Leu | Leu | Leu | Gly | |
| | | | 115 | | | | | 120 | | | | | 125 | | | |
| gct | ggc | ggt | gcg | gcc | caa | ggc | gtg | atg | ctg | cct | ctg | ctt | caa | caa | aag | 432 |
| Ala | Gly | Gly | Ala | Ala | Gln | Gly | Val | Met | Leu | Pro | Leu | Leu | Gln | Gln | Lys | |
| | 130 | | | | | 135 | | | | | 140 | | | | | |
| ccg | tca | cat | ttg | acc | gtg | gcc | aac | cgt | agt | gtc | gac | aag | gca | caa | gcg | 480 |
| Pro | Ser | His | Leu | Thr | Val | Ala | Asn | Arg | Ser | Val | Asp | Lys | Ala | Gln | Ala | |
| 145 | | | | | 150 | | | | | 155 | | | | | 160 | |
| atg | gtg | gac | aaa | ttt | tcc | agt | cac | gct | gtc | tcc | agt | gag | aca | ata | ttg | 528 |
| Met | Val | Asp | Lys | Phe | Ser | Ser | His | Ala | Val | Ser | Ser | Glu | Thr | Ile | Leu | |
| | | | | 165 | | | | | 170 | | | | | 175 | | |
| caa | gtg | aag | act | ttc | gtg | gat | tta | tcc | cta | gca | tat | gac | atc | gtc | att | 576 |

```
Gln Val Lys Thr Phe Val Asp Leu Ser Leu Ala Tyr Asp Ile Val Ile
            180                 185                 190 aat gcg acc tcg gcc gga tta acg gat agc tcg tta caa ctc ccg gtg       624
Asn Ala Thr Ser Ala Gly Leu Thr Asp Ser Ser Leu Gln Leu Pro Val
            195                 200                 205 gac ata ttt cag gcc aat aca ctg gct tac gac atg atg tat ggg cgc       672
Asp Ile Phe Gln Ala Asn Thr Leu Ala Tyr Asp Met Met Tyr Gly Arg
        210                 215                 220 gaa acg cca ttt atg cag cag gca cgt gca gcg gga gca cac gtg gct       720
Glu Thr Pro Phe Met Gln Gln Ala Arg Ala Ala Gly Ala His Val Ala
225                 230                 235                 240 gat ggt ttg ggt atg ctg gtg gaa caa gcg gct gaa gca ttt tat ctt       768
Asp Gly Leu Gly Met Leu Val Glu Gln Ala Ala Glu Ala Phe Tyr Leu
                    245                 250                 255 tgg cat ggt ttg cgt ccg gag acc gcc ccg gtg att cag tat ttc cgc       816
Trp His Gly Leu Arg Pro Glu Thr Ala Pro Val Ile Gln Tyr Phe Arg
                260                 265                 270 cag tct taa                                                           825
Gln Ser <210> SEQ ID NO 8
<211> LENGTH: 274
<212> TYPE: PRT
<213> ORGANISM: Methylophilus methylotrophus

<400> SEQUENCE: 8

Met Ala Val Glu Lys Tyr Ala Val Ile Gly Asn Pro Ile Glu His Ser
1               5                   10                  15

Lys Ser Pro Leu Ile His Gln Ala Phe Ala Lys Gln Phe Asn Lys Val
            20                  25                  30

Ile Gly Tyr Glu Lys Val Leu Ala Pro Leu Asp Gly Phe Glu Val Thr
        35                  40                  45

Leu Gln Arg Leu Arg Ala Glu Gly Tyr Leu Gly Ala Asn Val Thr Val
    50                  55                  60

Pro Phe Lys Phe Glu Ala Phe Asn Ala Cys Gln Glu Leu Ser Ala Arg
65                  70                  75                  80

Ala Gln Ala Ala Gly Ala Val Asn Thr Leu Ser Phe Asn Lys Gln Tyr
                85                  90                  95

Ile Ala Gly Asp Asn Thr Asp Gly Cys Gly Leu Val Asn Asp Ile Leu
            100                 105                 110

Gln His Gln His Thr Leu Leu Ala Gly Lys Lys Val Leu Leu Leu Gly
        115                 120                 125

Ala Gly Gly Ala Ala Gln Gly Val Met Leu Pro Leu Leu Gln Gln Lys
    130                 135                 140

Pro Ser His Leu Thr Val Ala Asn Arg Ser Val Asp Lys Ala Gln Ala
145                 150                 155                 160

Met Val Asp Lys Phe Ser Ser His Ala Val Ser Ser Glu Thr Ile Leu
                165                 170                 175

Gln Val Lys Thr Phe Val Asp Leu Ser Leu Ala Tyr Asp Ile Val Ile
            180                 185                 190

Asn Ala Thr Ser Ala Gly Leu Thr Asp Ser Ser Leu Gln Leu Pro Val
        195                 200                 205

Asp Ile Phe Gln Ala Asn Thr Leu Ala Tyr Asp Met Met Tyr Gly Arg
    210                 215                 220

Glu Thr Pro Phe Met Gln Gln Ala Arg Ala Ala Gly Ala His Val Ala
225                 230                 235                 240
```

```
Asp Gly Leu Gly Met Leu Val Glu Gln Ala Ala Glu Ala Phe Tyr Leu
            245                 250                 255

Trp His Gly Leu Arg Pro Glu Thr Ala Pro Val Ile Gln Tyr Phe Arg
        260                 265                 270

Gln Ser

<210> SEQ ID NO 9
<211> LENGTH: 1281
<212> TYPE: DNA
<213> ORGANISM: Methylophilus methylotrophus
<220> FEATURE:
<221> NAME/KEY: CDS
<222> LOCATION: (1)..(1281)
<223> OTHER INFORMATION:

<400> SEQUENCE: 9 atg gaa caa ctg cat tta cca gct gca cat caa gct caa ggc acc atc        48
Met Glu Gln Leu His Leu Pro Ala Ala His Gln Ala Gln Gly Thr Ile
1               5                   10                  15 acc ctg cct ggg tct aaa agt atc tca aac cgc act tta tta ctt gca       96
Thr Leu Pro Gly Ser Lys Ser Ile Ser Asn Arg Thr Leu Leu Leu Ala
            20                  25                  30 gcg ttg gcc gac ggc gtc aca att att cgc gac ttg ctt gct tct gat      144
Ala Leu Ala Asp Gly Val Thr Ile Ile Arg Asp Leu Leu Ala Ser Asp
        35                  40                  45 gac acg gca agg atg ttg gag gct ctg act tca tta ggt ttg caa ctt      192
Asp Thr Ala Arg Met Leu Glu Ala Leu Thr Ser Leu Gly Leu Gln Leu
    50                  55                  60 gag aat att ggc gaa aat gcc tgg cgg gtg aca ggt tgt ggc ggc aat      240
Glu Asn Ile Gly Glu Asn Ala Trp Arg Val Thr Gly Cys Gly Gly Asn
65                  70                  75                  80 ttc ccc aat aag cag gcg gat ctt ttt ttg ggc aat gct ggg aca gca      288
Phe Pro Asn Lys Gln Ala Asp Leu Phe Leu Gly Asn Ala Gly Thr Ala
                85                  90                  95 ttc agg cca ttg act gcg gcc ctt gcg ttt tct gaa ggc gaa tac cat      336
Phe Arg Pro Leu Thr Ala Ala Leu Ala Phe Ser Glu Gly Glu Tyr His
            100                 105                 110 ttg cat ggg gtc ccc cgt atg cac gag cgc ccg att ggc gat ctg gta      384
Leu His Gly Val Pro Arg Met His Glu Arg Pro Ile Gly Asp Leu Val
        115                 120                 125 gat gct tta aaa caa gtg ggt gca cag att gat tat ctg ggt aat cct      432
Asp Ala Leu Lys Gln Val Gly Ala Gln Ile Asp Tyr Leu Gly Asn Pro
    130                 135                 140 ggc tac cct ccc ctg caa att tcc ccg gcc aaa ctg aat gtc agt cag      480
Gly Tyr Pro Pro Leu Gln Ile Ser Pro Ala Lys Leu Asn Val Ser Gln
145                 150                 155                 160 ccc att caa atc cgg gga gat gtt tcc agc cag ttc ctg act gca tta      528
Pro Ile Gln Ile Arg Gly Asp Val Ser Ser Gln Phe Leu Thr Ala Leu
                165                 170                 175 tta atg gcg tta ccg ctc act ggg caa gcc gct acc ata gag gtg gtg      576
Leu Met Ala Leu Pro Leu Thr Gly Gln Ala Ala Thr Ile Glu Val Val
            180                 185                 190 ggc gaa tta atc tcc aag cct tat atc gaa atc aca ctt aac cta atg      624
Gly Glu Leu Ile Ser Lys Pro Tyr Ile Glu Ile Thr Leu Asn Leu Met
        195                 200                 205 caa cgc ttt ggt gtc agc gtt aaa cga gag ggc tgg cag cgc ttt tat      672
Gln Arg Phe Gly Val Ser Val Lys Arg Glu Gly Trp Gln Arg Phe Tyr
    210                 215                 220 atc ccc gcc gca gtc cgc tac caa tca cca ggc gaa atc tat gta gag      720
Ile Pro Ala Ala Val Arg Tyr Gln Ser Pro Gly Glu Ile Tyr Val Glu
225                 230                 235                 240
```

-continued

```
ggt gat gct tca agc gct tct tac ttt att gcc gcc ggt atc ctg gct     768
Gly Asp Ala Ser Ser Ala Ser Tyr Phe Ile Ala Ala Gly Ile Leu Ala
            245                 250                 255 ggg gat gtc act gtt aag ggc gtt ggt gaa aga agt atc cag ggc gat     816
Gly Asp Val Thr Val Lys Gly Val Gly Glu Arg Ser Ile Gln Gly Asp
        260                 265                 270 atc cgt ttt gcg gaa gcg gcc aat ttg atg ggt ggt cgt atc agc tat     864
Ile Arg Phe Ala Glu Ala Ala Asn Leu Met Gly Gly Arg Ile Ser Tyr
    275                 280                 285 ggt gag aac cat gta cgt gca gag aaa act gct gct tta aaa gca att     912
Gly Glu Asn His Val Arg Ala Glu Lys Thr Ala Ala Leu Lys Ala Ile
290                 295                 300 gac cta gac tgt aac cat att ccg gat gcg gcg atg aca ttg ggc gtc     960
Asp Leu Asp Cys Asn His Ile Pro Asp Ala Ala Met Thr Leu Gly Val
305                 310                 315                 320 atg gcg atg ttt gct gaa ggc aca acc acc ttg cgc aat att gcc agt    1008
Met Ala Met Phe Ala Glu Gly Thr Thr Thr Leu Arg Asn Ile Ala Ser
                325                 330                 335 tgg cgt gtc aaa gaa acc gac cgc att gcc gcc atg gcc aca gag tta    1056
Trp Arg Val Lys Glu Thr Asp Arg Ile Ala Ala Met Ala Thr Glu Leu
            340                 345                 350 cgc aaa gtg ggg gca acc gtg gtt gaa ggc gca gat ttt att cag gtg    1104
Arg Lys Val Gly Ala Thr Val Val Glu Gly Ala Asp Phe Ile Gln Val
        355                 360                 365 act ccg cca gcg cag ctc acg cct aat gca gtg atc gac acc tat gat    1152
Thr Pro Pro Ala Gln Leu Thr Pro Asn Ala Val Ile Asp Thr Tyr Asp
    370                 375                 380 gat cac cgc atg gcc atg tgc ttt tcg ctg att agc ctg gca ggt gtg    1200
Asp His Arg Met Ala Met Cys Phe Ser Leu Ile Ser Leu Ala Gly Val
385                 390                 395                 400 ccg att acg att aac gat cca aag tgc gta ggc aaa acg ttt cca gat    1248
Pro Ile Thr Ile Asn Asp Pro Lys Cys Val Gly Lys Thr Phe Pro Asp
                405                 410                 415 tac ttt aat gta ttc gcc agt att gcc cgc tag                        1281
Tyr Phe Asn Val Phe Ala Ser Ile Ala Arg
            420                 425
```

<210> SEQ ID NO 10
<211> LENGTH: 426
<212> TYPE: PRT
<213> ORGANISM: Methylophilus methylotrophus

<400> SEQUENCE: 10

```
Met Glu Gln Leu His Leu Pro Ala Ala His Gln Ala Gln Gly Thr Ile
1               5                   10                  15

Thr Leu Pro Gly Ser Lys Ser Ile Ser Asn Arg Thr Leu Leu Leu Ala
            20                  25                  30

Ala Leu Ala Asp Gly Val Thr Ile Ile Arg Asp Leu Leu Ala Ser Asp
        35                  40                  45

Asp Thr Ala Arg Met Leu Glu Ala Leu Thr Ser Leu Gly Leu Gln Leu
    50                  55                  60

Glu Asn Ile Gly Glu Asn Ala Trp Arg Val Thr Gly Cys Gly Gly Asn
65                  70                  75                  80

Phe Pro Asn Lys Gln Ala Asp Leu Phe Leu Gly Asn Ala Gly Thr Ala
                85                  90                  95

Phe Arg Pro Leu Thr Ala Ala Leu Ala Phe Ser Glu Gly Glu Tyr His
            100                 105                 110

Leu His Gly Val Pro Arg Met His Glu Arg Pro Ile Gly Asp Leu Val
```

```
            115                 120                 125
Asp Ala Leu Lys Gln Val Gly Ala Gln Ile Asp Tyr Leu Gly Asn Pro
    130                 135                 140
Gly Tyr Pro Pro Leu Gln Ile Ser Pro Ala Lys Leu Asn Val Ser Gln
145                 150                 155                 160
Pro Ile Gln Ile Arg Gly Asp Val Ser Ser Gln Phe Leu Thr Ala Leu
                165                 170                 175
Leu Met Ala Leu Pro Leu Thr Gly Gln Ala Ala Thr Ile Glu Val Val
            180                 185                 190
Gly Glu Leu Ile Ser Lys Pro Tyr Ile Glu Ile Thr Leu Asn Leu Met
        195                 200                 205
Gln Arg Phe Gly Val Ser Val Lys Arg Glu Gly Trp Gln Arg Phe Tyr
    210                 215                 220
Ile Pro Ala Ala Val Arg Tyr Gln Ser Pro Gly Glu Ile Tyr Val Glu
225                 230                 235                 240
Gly Asp Ala Ser Ser Ala Ser Tyr Phe Ile Ala Ala Gly Ile Leu Ala
                245                 250                 255
Gly Asp Val Thr Val Lys Gly Val Gly Glu Arg Ser Ile Gln Gly Asp
            260                 265                 270
Ile Arg Phe Ala Glu Ala Ala Asn Leu Met Gly Gly Arg Ile Ser Tyr
        275                 280                 285
Gly Glu Asn His Val Arg Ala Glu Lys Thr Ala Ala Leu Lys Ala Ile
    290                 295                 300
Asp Leu Asp Cys Asn His Ile Pro Asp Ala Ala Met Thr Leu Gly Val
305                 310                 315                 320
Met Ala Met Phe Ala Glu Gly Thr Thr Thr Leu Arg Asn Ile Ala Ser
                325                 330                 335
Trp Arg Val Lys Glu Thr Asp Arg Ile Ala Ala Met Ala Thr Glu Leu
            340                 345                 350
Arg Lys Val Gly Ala Thr Val Glu Gly Ala Asp Phe Ile Gln Val
        355                 360                 365
Thr Pro Pro Ala Gln Leu Thr Pro Asn Ala Val Ile Asp Thr Tyr Asp
    370                 375                 380
Asp His Arg Met Ala Met Cys Phe Ser Leu Ile Ser Leu Ala Gly Val
385                 390                 395                 400
Pro Ile Thr Ile Asn Asp Pro Lys Cys Val Gly Lys Thr Phe Pro Asp
                405                 410                 415
Tyr Phe Asn Val Phe Ala Ser Ile Ala Arg
            420                 425

<210> SEQ ID NO 11
<211> LENGTH: 1092
<212> TYPE: DNA
<213> ORGANISM: Methylophilus methylotrophus
<220> FEATURE:
<221> NAME/KEY: CDS
<222> LOCATION: (1)..(1092)
<223> OTHER INFORMATION:

<400> SEQUENCE: 11 atg tct ggc aat acc atc ggc acc ttg ttt acc ttg act tca ttt ggg    48
Met Ser Gly Asn Thr Ile Gly Thr Leu Phe Thr Leu Thr Ser Phe Gly
1               5                   10                  15 gag tca cat ggc cct ggc att ggc ggt att gtg gat ggg tgc cct cca    96
Glu Ser His Gly Pro Gly Ile Gly Gly Ile Val Asp Gly Cys Pro Pro
            20                  25                  30
```

```
gga ctc gag ctt agt gca gcc gat ttg caa gtg gat ctt gac cgc cgt    144
Gly Leu Glu Leu Ser Ala Ala Asp Leu Gln Val Asp Leu Asp Arg Arg
         35                  40                  45 aaa ccg gga act tct cgt cat gtg aca caa cgt aat gaa gcc gat gag    192
Lys Pro Gly Thr Ser Arg His Val Thr Gln Arg Asn Glu Ala Asp Glu
 50                  55                  60 gtt gaa atc ctc tct ggg gta ttt gag ggt aaa act acc ggt acc ccg    240
Val Glu Ile Leu Ser Gly Val Phe Glu Gly Lys Thr Thr Gly Thr Pro
 65                  70                  75                  80 ata ggc ttg ctg atc cgc aac acc gat cag cgc tcg cag gat tac agc    288
Ile Gly Leu Leu Ile Arg Asn Thr Asp Gln Arg Ser Gln Asp Tyr Ser
                 85                  90                  95 aag atc atg gat act ttc cgt cct gga cat gct gac tat acc tac agc    336
Lys Ile Met Asp Thr Phe Arg Pro Gly His Ala Asp Tyr Thr Tyr Ser
            100                 105                 110 cag aaa tac ggt atc cgt gat tat cgt ggc ggt ggc cgt tcc agc gca    384
Gln Lys Tyr Gly Ile Arg Asp Tyr Arg Gly Gly Gly Arg Ser Ser Ala
            115                 120                 125 cgt gaa acc gca gta cgc gtg gcc gca ggt gcc atc gcc aag aag tgg    432
Arg Glu Thr Ala Val Arg Val Ala Ala Gly Ala Ile Ala Lys Lys Trp
130                 135                 140 ctc aag gaa aaa tac ggc atc cag att cgt ggt tat ctc agc cag att    480
Leu Lys Glu Lys Tyr Gly Ile Gln Ile Arg Gly Tyr Leu Ser Gln Ile
145                 150                 155                 160 ggt gag atc gag atc cca ttc gtg agc tgg gag gca gtg tca caa gag    528
Gly Glu Ile Glu Ile Pro Phe Val Ser Trp Glu Ala Val Ser Gln Glu
                165                 170                 175 ggc aat gct ttc ttc tca ccc aat gtc gaa atc ctg ccg caa ctg gaa    576
Gly Asn Ala Phe Phe Ser Pro Asn Val Glu Ile Leu Pro Gln Leu Glu
            180                 185                 190 gcc tat atg gac cag atc cgt agt gag cgt gac tca gtg ggc gcg caa    624
Ala Tyr Met Asp Gln Ile Arg Ser Glu Arg Asp Ser Val Gly Ala Gln
            195                 200                 205 att act gtg gtc gct gaa aaa gtc cct gta ggc ctt gga gaa cct gta    672
Ile Thr Val Val Ala Glu Lys Val Pro Val Gly Leu Gly Glu Pro Val
            210                 215                 220 ttt gac cgg ctg gat gcc gat att gcc cat gcc atg atg ggc atc aac    720
Phe Asp Arg Leu Asp Ala Asp Ile Ala His Ala Met Met Gly Ile Asn
225                 230                 235                 240 gcc gtc aaa ggc gtt gaa atc ggt gcg ggg ttt gat tca gtc gca cag    768
Ala Val Lys Gly Val Glu Ile Gly Ala Gly Phe Asp Ser Val Ala Gln
                245                 250                 255 cgt ggc agt gtc cac agt gat gaa ctt acg cca gag ggc ttc gcc acc    816
Arg Gly Ser Val His Ser Asp Glu Leu Thr Pro Glu Gly Phe Ala Thr
            260                 265                 270 aat cac gct ggt ggt gtg ctg ggc ggc atc tcc acc ggt caa gat att    864
Asn His Ala Gly Gly Val Leu Gly Gly Ile Ser Thr Gly Gln Asp Ile
            275                 280                 285 gtg gtc aat gtc gcg ttc aag ccc act tcg agc atc ccg caa cag cgc    912
Val Val Asn Val Ala Phe Lys Pro Thr Ser Ser Ile Pro Gln Gln Arg
            290                 295                 300 cac tcc atc aat cag gcc ggt gat gcg gtc atg atg caa acc aca ggc    960
His Ser Ile Asn Gln Ala Gly Asp Ala Val Met Met Gln Thr Thr Gly
305                 310                 315                 320 cgt cat gat cca tgc gta ggc ata cgt gcg aca ccg atc gta gaa gca   1008
Arg His Asp Pro Cys Val Gly Ile Arg Ala Thr Pro Ile Val Glu Ala
                325                 330                 335 atg ctg gca ctg gtg ttg atg gat cat gcc ctg cgc cac cgt ggt cag   1056
Met Leu Ala Leu Val Leu Met Asp His Ala Leu Arg His Arg Gly Gln
            340                 345                 350
```

```
aat gca gac gtg cat acc agc gtt cca aaa ttg taa                    1092
Asn Ala Asp Val His Thr Ser Val Pro Lys Leu
        355                 360
```

<210> SEQ ID NO 12
<211> LENGTH: 363
<212> TYPE: PRT
<213> ORGANISM: Methylophilus methylotrophus

<400> SEQUENCE: 12

```
Met Ser Gly Asn Thr Ile Gly Thr Leu Phe Thr Leu Thr Ser Phe Gly
1               5                   10                  15

Glu Ser His Gly Pro Gly Ile Gly Gly Ile Val Asp Gly Cys Pro Pro
            20                  25                  30

Gly Leu Glu Leu Ser Ala Ala Asp Leu Gln Val Asp Leu Asp Arg Arg
        35                  40                  45

Lys Pro Gly Thr Ser Arg His Val Thr Gln Arg Asn Glu Ala Asp Glu
    50                  55                  60

Val Glu Ile Leu Ser Gly Val Phe Glu Gly Lys Thr Thr Gly Thr Pro
65                  70                  75                  80

Ile Gly Leu Leu Ile Arg Asn Thr Asp Gln Arg Ser Gln Asp Tyr Ser
                85                  90                  95

Lys Ile Met Asp Thr Phe Arg Pro Gly His Ala Asp Tyr Thr Tyr Ser
            100                 105                 110

Gln Lys Tyr Gly Ile Arg Asp Tyr Arg Gly Gly Arg Ser Ser Ala
        115                 120                 125

Arg Glu Thr Ala Val Arg Val Ala Ala Gly Ala Ile Ala Lys Lys Trp
    130                 135                 140

Leu Lys Glu Lys Tyr Gly Ile Gln Ile Arg Gly Tyr Leu Ser Gln Ile
145                 150                 155                 160

Gly Glu Ile Glu Ile Pro Phe Val Ser Trp Glu Ala Val Ser Gln Glu
                165                 170                 175

Gly Asn Ala Phe Phe Ser Pro Asn Val Glu Ile Leu Pro Gln Leu Glu
            180                 185                 190

Ala Tyr Met Asp Gln Ile Arg Ser Glu Arg Asp Ser Val Gly Ala Gln
        195                 200                 205

Ile Thr Val Val Ala Glu Lys Val Pro Val Gly Leu Gly Glu Pro Val
    210                 215                 220

Phe Asp Arg Leu Asp Ala Asp Ile Ala His Ala Met Met Gly Ile Asn
225                 230                 235                 240

Ala Val Lys Gly Val Glu Ile Gly Ala Gly Phe Asp Ser Val Ala Gln
                245                 250                 255

Arg Gly Ser Val His Ser Asp Glu Leu Thr Pro Glu Gly Phe Ala Thr
            260                 265                 270

Asn His Ala Gly Val Leu Gly Ile Ser Thr Gly Gln Asp Ile
        275                 280                 285

Val Val Asn Val Ala Phe Lys Pro Thr Ser Ser Ile Pro Gln Gln Arg
    290                 295                 300

His Ser Ile Asn Gln Ala Gly Asp Ala Val Met Met Gln Thr Thr Gly
305                 310                 315                 320

Arg His Asp Pro Cys Val Gly Ile Arg Ala Thr Pro Ile Val Glu Ala
                325                 330                 335

Met Leu Ala Leu Val Leu Met Asp His Ala Leu Arg His Arg Gly Gln
            340                 345                 350
```

```
         Asn Ala Asp Val His Thr Ser Val Pro Lys Leu
                 355                 360
```

<210> SEQ ID NO 13
<211> LENGTH: 891
<212> TYPE: DNA
<213> ORGANISM: Methylophilus methylotrophus
<220> FEATURE:
<221> NAME/KEY: CDS
<222> LOCATION: (1)..(891)
<223> OTHER INFORMATION:

<400> SEQUENCE: 13

```
atg aca tgg tac aat tcg act atg ttc aaa aaa att gtg att ttt ggg      48
Met Thr Trp Tyr Asn Ser Thr Met Phe Lys Lys Ile Val Ile Phe Gly
 1               5                  10                  15 gta ggt tta atc ggg gga tca gtt gct ctc tca ctg aaa aaa cag gca      96
Val Gly Leu Ile Gly Gly Ser Val Ala Leu Ser Leu Lys Lys Gln Ala
             20                  25                  30 cat atc cct caa gtg gta ggt gtt ggc cga tct ggt caa agc ctg caa     144
His Ile Pro Gln Val Val Gly Val Gly Arg Ser Gly Gln Ser Leu Gln
         35                  40                  45 gaa gcg ctg aaa ctg ggt ttg att gat gtc gct gaa aca gac gtt gcc     192
Glu Ala Leu Lys Leu Gly Leu Ile Asp Val Ala Glu Thr Asp Val Ala
     50                  55                  60 cat gca atg caa gat gcc gac ctg gta ctc atc gcc gcc ccc gta gcg     240
His Ala Met Gln Asp Ala Asp Leu Val Leu Ile Ala Ala Pro Val Ala
 65                  70                  75                  80 caa acg cct gca att tta cgt tcg att cgc ccg cat tta aat gca gcg     288
Gln Thr Pro Ala Ile Leu Arg Ser Ile Arg Pro His Leu Asn Ala Ala
                 85                  90                  95 acg att att act gat gct ggc agc aca aaa tcg gat gtg atg gct tat     336
Thr Ile Ile Thr Asp Ala Gly Ser Thr Lys Ser Asp Val Met Ala Tyr
            100                 105                 110 gca aaa gcc gag tta ggt gac aag ttt gac cag ttc gtc gga ggt cac     384
Ala Lys Ala Glu Leu Gly Asp Lys Phe Asp Gln Phe Val Gly Gly His
        115                 120                 125 ccg att gcc ggt gct gaa aaa agc ggc cct gct gcg gcc atg gct gat     432
Pro Ile Ala Gly Ala Glu Lys Ser Gly Pro Ala Ala Ala Met Ala Asp
    130                 135                 140 tta tat atc ggc aaa aat gta atc ctg acg ccg gac gca gat aca caa     480
Leu Tyr Ile Gly Lys Asn Val Ile Leu Thr Pro Asp Ala Asp Thr Gln
145                 150                 155                 160 tca aca gcg ata gac aaa gtc acc gca ctt tgg caa caa tgt ggt gct     528
Ser Thr Ala Ile Asp Lys Val Thr Ala Leu Trp Gln Gln Cys Gly Ala
                165                 170                 175 gtg gtg tcc agg atg agc cct cag gag cat gat aac gtg ttt gct gcg     576
Val Val Ser Arg Met Ser Pro Gln Glu His Asp Asn Val Phe Ala Ala
            180                 185                 190 gtt agc cat ttg ccc cat tta ctg gca ttt gcc ttg gta gag gac ctg     624
Val Ser His Leu Pro His Leu Leu Ala Phe Ala Leu Val Glu Asp Leu
        195                 200                 205 gct aaa cga gac aat gcc gaa ttg ctg ttt aag ttt gcc gcc agt ggt     672
Ala Lys Arg Asp Asn Ala Glu Leu Leu Phe Lys Phe Ala Ala Ser Gly
    210                 215                 220 ttc aga gat ttt acg cgc att gct ggc agt cat cct gaa atg tgg cga     720
Phe Arg Asp Phe Thr Arg Ile Ala Gly Ser His Pro Glu Met Trp Arg
225                 230                 235                 240 gac att gct ctc gct aac aaa acg gct ctg cta ggc gaa ctc aaa ctt     768
Asp Ile Ala Leu Ala Asn Lys Thr Ala Leu Leu Gly Glu Leu Lys Leu
                245                 250                 255
```

-continued

```
tac cag cag gcc ttg agt gaa atg aca gcc ctg ctt gaa aag gca gat    816
Tyr Gln Gln Ala Leu Ser Glu Met Thr Ala Leu Leu Glu Lys Ala Asp
        260                 265                 270 gcc gat ggg ttg caa gcc cta ttt gaa cat gcc agc cgt gcc cgc aac    864
Ala Asp Gly Leu Gln Ala Leu Phe Glu His Ala Ser Arg Ala Arg Asn
        275                 280                 285 gat tgg gca aaa act aaa att caa taa                                891
Asp Trp Ala Lys Thr Lys Ile Gln
        290                 295
```

<210> SEQ ID NO 14
<211> LENGTH: 296
<212> TYPE: PRT
<213> ORGANISM: Methylophilus methylotrophus

<400> SEQUENCE: 14

```
Met Thr Trp Tyr Asn Ser Thr Met Phe Lys Lys Ile Val Ile Phe Gly
  1               5                  10                  15

Val Gly Leu Ile Gly Gly Ser Val Ala Leu Ser Leu Lys Lys Gln Ala
                 20                  25                  30

His Ile Pro Gln Val Val Gly Val Gly Arg Ser Gly Gln Ser Leu Gln
             35                  40                  45

Glu Ala Leu Lys Leu Gly Leu Ile Asp Val Ala Glu Thr Asp Val Ala
         50                  55                  60

His Ala Met Gln Asp Ala Asp Leu Val Leu Ile Ala Ala Pro Val Ala
 65                  70                  75                  80

Gln Thr Pro Ala Ile Leu Arg Ser Ile Arg Pro His Leu Asn Ala Ala
                 85                  90                  95

Thr Ile Ile Thr Asp Ala Gly Ser Thr Lys Ser Asp Val Met Ala Tyr
            100                 105                 110

Ala Lys Ala Glu Leu Gly Asp Lys Phe Asp Gln Phe Val Gly Gly His
        115                 120                 125

Pro Ile Ala Gly Ala Glu Lys Ser Gly Pro Ala Ala Met Ala Asp
        130                 135                 140

Leu Tyr Ile Gly Lys Asn Val Ile Leu Thr Pro Asp Ala Asp Thr Gln
145                 150                 155                 160

Ser Thr Ala Ile Asp Lys Val Thr Ala Leu Trp Gln Gln Cys Gly Ala
                165                 170                 175

Val Val Ser Arg Met Ser Pro Gln Glu His Asp Asn Val Phe Ala Ala
            180                 185                 190

Val Ser His Leu Pro His Leu Leu Ala Phe Ala Leu Val Glu Asp Leu
        195                 200                 205

Ala Lys Arg Asp Asn Ala Glu Leu Leu Phe Lys Phe Ala Ala Ser Gly
    210                 215                 220

Phe Arg Asp Phe Thr Arg Ile Ala Gly Ser His Pro Glu Met Trp Arg
225                 230                 235                 240

Asp Ile Ala Leu Ala Asn Lys Thr Ala Leu Leu Gly Glu Leu Lys Leu
                245                 250                 255

Tyr Gln Gln Ala Leu Ser Glu Met Thr Ala Leu Leu Glu Lys Ala Asp
            260                 265                 270

Ala Asp Gly Leu Gln Ala Leu Phe Glu His Ala Ser Arg Ala Arg Asn
        275                 280                 285

Asp Trp Ala Lys Thr Lys Ile Gln
        290                 295
```

<210> SEQ ID NO 15

```
-continued

<211> LENGTH: 1518
<212> TYPE: DNA
<213> ORGANISM: Methylophilus methylotrophus
<220> FEATURE:
<221> NAME/KEY: CDS
<222> LOCATION: (1)..(1518)
<223> OTHER INFORMATION:

<400> SEQUENCE: 15 atg tta agc aca tta agc aag acc gaa ttc gac gcg ctg gcg gcg caa        48
Met Leu Ser Thr Leu Ser Lys Thr Glu Phe Asp Ala Leu Ala Ala Gln
1               5                   10                  15 ggc tac aac cgt att ccg ctg gtg cta gaa acc ttt gcc gat ctg gat        96
Gly Tyr Asn Arg Ile Pro Leu Val Leu Glu Thr Phe Ala Asp Leu Asp
            20                  25                  30 aca ccc tta tca ctg tat ctc aaa ctg gcc aat caa cct tat tcc tac       144
Thr Pro Leu Ser Leu Tyr Leu Lys Leu Ala Asn Gln Pro Tyr Ser Tyr
        35                  40                  45 ctg ctc gaa agc gta caa ggc ggc gag cgc ttt ggc cgt tat tcg att       192
Leu Leu Glu Ser Val Gln Gly Gly Glu Arg Phe Gly Arg Tyr Ser Ile
    50                  55                  60 ata ggc ctg cct gcc act acc cgc atc gtg gtg cga gac cag caa ttg       240
Ile Gly Leu Pro Ala Thr Thr Arg Ile Val Val Arg Asp Gln Gln Leu
65                  70                  75                  80 cag gtg att cag gat cat cag gtc ata gaa tca cat tcc gat caa aac       288
Gln Val Ile Gln Asp His Gln Val Ile Glu Ser His Ser Asp Gln Asn
                85                  90                  95 ccg ctg gac ttt atc aag gcg tat cag gcg cgc ttt aaa acg ccg cct       336
Pro Leu Asp Phe Ile Lys Ala Tyr Gln Ala Arg Phe Lys Thr Pro Pro
            100                 105                 110 tat gat ggt tta ccg cgc ttt acc ggc ggc ttg gcc ggt tat ttt ggc       384
Tyr Asp Gly Leu Pro Arg Phe Thr Gly Gly Leu Ala Gly Tyr Phe Gly
        115                 120                 125 tac gag acc att caa tac atc gaa aaa cgt ctc ggc aaa cag aaa aaa       432
Tyr Glu Thr Ile Gln Tyr Ile Glu Lys Arg Leu Gly Lys Gln Lys Lys
    130                 135                 140 cct gac gcg ata ggt gta ccc gat atc ctg ctc atg gtg tct gaa gag       480
Pro Asp Ala Ile Gly Val Pro Asp Ile Leu Leu Met Val Ser Glu Glu
145                 150                 155                 160 att gcc gtg gta gat aac ctc tcg ggc aag ctc tat ttt att gta tac       528
Ile Ala Val Val Asp Asn Leu Ser Gly Lys Leu Tyr Phe Ile Val Tyr
                165                 170                 175 gca gaa ccc gca aag gca gat gcc tac gaa acg gct tgt gcc cgt atg       576
Ala Glu Pro Ala Lys Ala Asp Ala Tyr Glu Thr Ala Cys Ala Arg Met
            180                 185                 190 cat gat tta ttg gct aga tta cgc act cag gtt gac att cct gac gca       624
His Asp Leu Leu Ala Arg Leu Arg Thr Gln Val Asp Ile Pro Asp Ala
        195                 200                 205 tta gcc acc cat aaa aca cag gcg gtg tct gag ttt ggt gag gat aac       672
Leu Ala Thr His Lys Thr Gln Ala Val Ser Glu Phe Gly Glu Asp Asn
    210                 215                 220 ttc aag gcg gca gtc aaa aag gca cag caa tat att cta gaa ggc gac       720
Phe Lys Ala Ala Val Lys Lys Ala Gln Gln Tyr Ile Leu Glu Gly Asp
225                 230                 235                 240 atc atg cag gtg gta ttg agc cag cgg atg tcg caa gat ttt gat gcc       768
Ile Met Gln Val Val Leu Ser Gln Arg Met Ser Gln Asp Phe Asp Ala
                245                 250                 255 tcg cca ttg agc ttg tac cgc gct ttg cgt agc ctc aac cct tcc cca       816
Ser Pro Leu Ser Leu Tyr Arg Ala Leu Arg Ser Leu Asn Pro Ser Pro
            260                 265                 270 tat atg ttc tat tac gat atg gat gat cac cat gtg gtc gga gct tca       864
```

-continued

```
                    Tyr Met Phe Tyr Tyr Asp Met Asp Asp His His Val Val Gly Ala Ser
                                275                 280                 285 cca gaa atc ctg gtg cgt ctg gaa gag acc acc gtg acc tca cgg ccg        912
Pro Glu Ile Leu Val Arg Leu Glu Glu Thr Thr Val Thr Ser Arg Pro
    290                 295                 300 att gcc ggg aca cgt cca cgt ggt aaa aac cgt gac cat gac ctg gcg        960
Ile Ala Gly Thr Arg Pro Arg Gly Lys Asn Arg Asp His Asp Leu Ala
305                 310                 315                 320 ctt gaa gca gag ttg ctg gcc gat ccg aaa gaa cgt gcc gag cat gtg       1008
Leu Glu Ala Glu Leu Leu Ala Asp Pro Lys Glu Arg Ala Glu His Val
                325                 330                 335 caa ctg atg gat ctg ggc cgc aac gac gtc ggc cgt gtc gca ctg act       1056
Gln Leu Met Asp Leu Gly Arg Asn Asp Val Gly Arg Val Ala Leu Thr
            340                 345                 350 ggt acg gtc aaa gtc act gac aat atg acc att gag cgc tat tca cat       1104
Gly Thr Val Lys Val Thr Asp Asn Met Thr Ile Glu Arg Tyr Ser His
        355                 360                 365 gtc atg cat att gtc agc aac gtc gaa ggc cag ctc aag cca ggc ttg       1152
Val Met His Ile Val Ser Asn Val Glu Gly Gln Leu Lys Pro Gly Leu
    370                 375                 380 gat gcg att gat gtg ctc aaa gcg act ttc cct gcc ggg acg gtg tct       1200
Asp Ala Ile Asp Val Leu Lys Ala Thr Phe Pro Ala Gly Thr Val Ser
385                 390                 395                 400 ggt gcc cct aaa gtg cgc gcc atg gaa atc att gaa gaa ctg gag cct       1248
Gly Ala Pro Lys Val Arg Ala Met Glu Ile Ile Glu Glu Leu Glu Pro
                405                 410                 415 tcc aaa cgt ggc att tat gct ggt gcc gtc ggc tat tta ggc ttt aat       1296
Ser Lys Arg Gly Ile Tyr Ala Gly Ala Val Gly Tyr Leu Gly Phe Asn
            420                 425                 430 ggc gac atg gat gtc gcg att gcg atc cgt acg gct gtg atc aaa aac       1344
Gly Asp Met Asp Val Ala Ile Ala Ile Arg Thr Ala Val Ile Lys Asn
        435                 440                 445 aaa aaa ctc tat gtg cag gcg ggc gcg ggc att gtg gcc gat tcg gtg       1392
Lys Lys Leu Tyr Val Gln Ala Gly Ala Gly Ile Val Ala Asp Ser Val
    450                 455                 460 ccg caa agc gaa tgg gaa gaa acc caa aac aag gcc aaa gcc gtc atc       1440
Pro Gln Ser Glu Trp Glu Glu Thr Gln Asn Lys Ala Lys Ala Val Ile
465                 470                 475                 480 cgc gcc gct gaa ctg gtg cag gca ggt ctg gat agc cag gcc gct aat       1488
Arg Ala Ala Glu Leu Val Gln Ala Gly Leu Asp Ser Gln Ala Ala Asn
                485                 490                 495 gtt caa acc cat gca gga aaa gga gcc tga                               1518
Val Gln Thr His Ala Gly Lys Gly Ala
            500                 505

<210> SEQ ID NO 16
<211> LENGTH: 505
<212> TYPE: PRT
<213> ORGANISM: Methylophilus methylotrophus

<400> SEQUENCE: 16

Met Leu Ser Thr Leu Ser Lys Thr Glu Phe Asp Ala Leu Ala Ala Gln
1               5                   10                  15

Gly Tyr Asn Arg Ile Pro Leu Val Leu Glu Thr Phe Ala Asp Leu Asp
            20                  25                  30

Thr Pro Leu Ser Leu Tyr Leu Lys Leu Ala Asn Gln Pro Tyr Ser Tyr
        35                  40                  45

Leu Leu Glu Ser Val Gln Gly Gly Glu Arg Phe Gly Arg Tyr Ser Ile
    50                  55                  60
```

```
Ile Gly Leu Pro Ala Thr Thr Arg Ile Val Val Arg Asp Gln Gln Leu
 65                  70                  75                  80

Gln Val Ile Gln Asp His Gln Val Ile Glu Ser His Ser Asp Gln Asn
             85                  90                  95

Pro Leu Asp Phe Ile Lys Ala Tyr Gln Ala Arg Phe Lys Thr Pro Pro
            100                 105                 110

Tyr Asp Gly Leu Pro Arg Phe Thr Gly Gly Leu Ala Gly Tyr Phe Gly
        115                 120                 125

Tyr Glu Thr Ile Gln Tyr Ile Glu Lys Arg Leu Gly Lys Gln Lys Lys
    130                 135                 140

Pro Asp Ala Ile Gly Val Pro Asp Ile Leu Leu Met Val Ser Glu Glu
145                 150                 155                 160

Ile Ala Val Val Asp Asn Leu Ser Gly Lys Leu Tyr Phe Ile Val Tyr
                165                 170                 175

Ala Glu Pro Ala Lys Ala Asp Ala Tyr Glu Thr Ala Cys Ala Arg Met
            180                 185                 190

His Asp Leu Leu Ala Arg Leu Arg Thr Gln Val Asp Ile Pro Asp Ala
        195                 200                 205

Leu Ala Thr His Lys Thr Gln Ala Val Ser Glu Phe Gly Glu Asp Asn
    210                 215                 220

Phe Lys Ala Ala Val Lys Lys Ala Gln Gln Tyr Ile Leu Glu Gly Asp
225                 230                 235                 240

Ile Met Gln Val Val Leu Ser Gln Arg Met Ser Gln Asp Phe Asp Ala
                245                 250                 255

Ser Pro Leu Ser Leu Tyr Arg Ala Leu Arg Ser Leu Asn Pro Ser Pro
            260                 265                 270

Tyr Met Phe Tyr Tyr Asp Met Asp Asp His His Val Val Gly Ala Ser
        275                 280                 285

Pro Glu Ile Leu Val Arg Leu Glu Glu Thr Thr Val Thr Ser Arg Pro
    290                 295                 300

Ile Ala Gly Thr Arg Pro Arg Gly Lys Asn Arg Asp His Asp Leu Ala
305                 310                 315                 320

Leu Glu Ala Glu Leu Leu Ala Asp Pro Lys Glu Arg Ala Glu His Val
                325                 330                 335

Gln Leu Met Asp Leu Gly Arg Asn Asp Val Gly Arg Val Ala Leu Thr
            340                 345                 350

Gly Thr Val Lys Val Thr Asp Asn Met Thr Ile Glu Arg Tyr Ser His
        355                 360                 365

Val Met His Ile Val Ser Asn Val Glu Gly Gln Leu Lys Pro Gly Leu
    370                 375                 380

Asp Ala Ile Asp Val Leu Lys Ala Thr Phe Pro Ala Gly Thr Val Ser
385                 390                 395                 400

Gly Ala Pro Lys Val Arg Ala Met Glu Ile Ile Glu Glu Leu Glu Pro
                405                 410                 415

Ser Lys Arg Gly Ile Tyr Ala Gly Ala Val Gly Tyr Leu Gly Phe Asn
            420                 425                 430

Gly Asp Met Asp Val Ala Ile Ala Ile Arg Thr Ala Val Ile Lys Asn
        435                 440                 445

Lys Lys Leu Tyr Val Gln Ala Gly Ala Gly Ile Val Ala Asp Ser Val
    450                 455                 460

Pro Gln Ser Glu Trp Glu Glu Thr Gln Asn Lys Ala Lys Ala Val Ile
465                 470                 475                 480

Arg Ala Ala Glu Leu Val Gln Ala Gly Leu Asp Ser Gln Ala Ala Asn
```

```
                       485                  490                  495
Val Gln Thr His Ala Gly Lys Gly Ala
            500                  505

<210> SEQ ID NO 17
<211> LENGTH: 567
<212> TYPE: DNA
<213> ORGANISM: Methylophilus methylotrophus
<220> FEATURE:
<221> NAME/KEY: CDS
<222> LOCATION: (1)..(567)
<223> OTHER INFORMATION:

<400> SEQUENCE: 17 atg ttg ttg atg att gat aac tac gac tct ttt acc tat aac ctc gtg      48
Met Leu Leu Met Ile Asp Asn Tyr Asp Ser Phe Thr Tyr Asn Leu Val
1               5                   10                  15 cag tat ttt ggc gag ctc ggg caa gat gtg cat gtg cac cgc aat gac      96
Gln Tyr Phe Gly Glu Leu Gly Gln Asp Val His Val His Arg Asn Asp
                20                  25                  30 gaa atc acg cta gaa cag atc aaa gcg atg gcg ccg gaa aaa atc gtg     144
Glu Ile Thr Leu Glu Gln Ile Lys Ala Met Ala Pro Glu Lys Ile Val
            35                  40                  45 att tct ccc gga ccg tgc aca cca aac gaa gcc ggg att tcc gtg ccc     192
Ile Ser Pro Gly Pro Cys Thr Pro Asn Glu Ala Gly Ile Ser Val Pro
        50                  55                  60 ctg att cac gag ttt gct ggc aaa att cct ttg ctg ggc gtg tgc ttg     240
Leu Ile His Glu Phe Ala Gly Lys Ile Pro Leu Leu Gly Val Cys Leu
65                  70                  75                  80 ggt cat cag agc ata ggc cag gct ttt ggt ggc aac atc atc aag gcc     288
Gly His Gln Ser Ile Gly Gln Ala Phe Gly Gly Asn Ile Ile Lys Ala
                85                  90                  95 aaa acg ctg atg cac ggt aaa acc tca ttg att cac cat acc aat acc     336
Lys Thr Leu Met His Gly Lys Thr Ser Leu Ile His His Thr Asn Thr
            100                 105                 110 ggc gtg ttc aga aac ctg cct aat ccc tat acg gca acg cgt tac cac     384
Gly Val Phe Arg Asn Leu Pro Asn Pro Tyr Thr Ala Thr Arg Tyr His
        115                 120                 125 tca ttg gtg att gag cgt gaa acc atc ccg gat tgc ctg gag atc acg     432
Ser Leu Val Ile Glu Arg Glu Thr Ile Pro Asp Cys Leu Glu Ile Thr
130                 135                 140 gcc tgg act gaa gat ggc gag atc atg ggc gtc aag cat aaa aca cta     480
Ala Trp Thr Glu Asp Gly Glu Ile Met Gly Val Lys His Lys Thr Leu
145                 150                 155                 160 gcc gtg gaa ggc gta cag ttt cac ccc gag tct atc ttg act gaa tat     528
Ala Val Glu Gly Val Gln Phe His Pro Glu Ser Ile Leu Thr Glu Tyr
                165                 170                 175 ggg cat gag ctg ctg gac aac ttc ctg aaa ggc tat tga                  567
Gly His Glu Leu Leu Asp Asn Phe Leu Lys Gly Tyr
            180                 185

<210> SEQ ID NO 18
<211> LENGTH: 188
<212> TYPE: PRT
<213> ORGANISM: Methylophilus methylotrophus

<400> SEQUENCE: 18

Met Leu Leu Met Ile Asp Asn Tyr Asp Ser Phe Thr Tyr Asn Leu Val
1               5                   10                  15

Gln Tyr Phe Gly Glu Leu Gly Gln Asp Val His Val His Arg Asn Asp
                20                  25                  30
```

```
Glu Ile Thr Leu Glu Gln Ile Lys Ala Met Ala Pro Glu Lys Ile Val
             35                  40                  45

Ile Ser Pro Gly Pro Cys Thr Pro Asn Glu Ala Gly Ile Ser Val Pro
 50                  55                  60

Leu Ile His Glu Phe Ala Gly Lys Ile Pro Leu Leu Gly Val Cys Leu
 65                  70                  75                  80

Gly His Gln Ser Ile Gly Gln Ala Phe Gly Gly Asn Ile Ile Lys Ala
             85                  90                  95

Lys Thr Leu Met His Gly Lys Thr Ser Leu Ile His His Thr Asn Thr
            100                 105                 110

Gly Val Phe Arg Asn Leu Pro Asn Pro Tyr Thr Ala Thr Arg Tyr His
            115                 120                 125

Ser Leu Val Ile Glu Arg Glu Thr Ile Pro Asp Cys Leu Glu Ile Thr
130                 135                 140

Ala Trp Thr Glu Asp Gly Glu Ile Met Gly Val Lys His Lys Thr Leu
145                 150                 155                 160

Ala Val Glu Gly Val Gln Phe His Pro Glu Ser Ile Leu Thr Glu Tyr
                165                 170                 175

Gly His Glu Leu Leu Asp Asn Phe Leu Lys Gly Tyr
            180                 185

<210> SEQ ID NO 19
<211> LENGTH: 1026
<212> TYPE: DNA
<213> ORGANISM: Methylophilus methylotrophus
<220> FEATURE:
<221> NAME/KEY: CDS
<222> LOCATION: (1)..(1026)
<223> OTHER INFORMATION:

<400> SEQUENCE: 19 atg gcc atc acg cct aaa atc gcc tta cag cgc ctg att gac cac acc      48
Met Ala Ile Thr Pro Lys Ile Ala Leu Gln Arg Leu Ile Asp His Thr
  1               5                  10                  15 gat ttc acg cat gat gaa atg ctg gaa atc atg cag cag atc atg agt     96
Asp Phe Thr His Asp Glu Met Leu Glu Ile Met Gln Gln Ile Met Ser
             20                  25                  30 ggt gaa ttc acg cag atc cag att gcc ggc ttt ttg tca gcc ttg cgc    144
Gly Glu Phe Thr Gln Ile Gln Ile Ala Gly Phe Leu Ser Ala Leu Arg
         35                  40                  45 gtc aag ggc gaa acc gtg acc gaa att gcc gcc gct gcg cag gtg atg    192
Val Lys Gly Glu Thr Val Thr Glu Ile Ala Ala Ala Ala Gln Val Met
 50                  55                  60 cgc gag ctt tcc agc aag gta gag atc acc gat acc cgc cac ctg att    240
Arg Glu Leu Ser Ser Lys Val Glu Ile Thr Asp Thr Arg His Leu Ile
 65                  70                  75                  80 gat acc tgt ggc act ggc ggt gcg ccg aac aag gta ttt aac gtc tcc    288
Asp Thr Cys Gly Thr Gly Gly Ala Pro Asn Lys Val Phe Asn Val Ser
                 85                  90                  95 acc gcg tca gcc ttt gtc gcc gca ggc gca ggt gca aaa atc gcc aag    336
Thr Ala Ser Ala Phe Val Ala Ala Gly Ala Gly Ala Lys Ile Ala Lys
            100                 105                 110 cat ggt ggc cgc gca gct tct tca aaa agc ggc tct gcc gat gtg ctg    384
His Gly Gly Arg Ala Ala Ser Ser Lys Ser Gly Ser Ala Asp Val Leu
        115                 120                 125 gaa gcg ttg ggt gtc aat att gtg tta acg cct gaa caa gtg gta cgt    432
Glu Ala Leu Gly Val Asn Ile Val Leu Thr Pro Glu Gln Val Val Arg
130                 135                 140 tgc gtc aac gag gcc ggt att ggc ttt atg ttt gcg cct aat cac cac    480
```

```
                                                                         528
gcg gcc atg aaa tac gca gcg ccc gtg cgc cgc gaa ctg ggt gta cgc
Ala Ala Met Lys Tyr Ala Ala Pro Val Arg Arg Glu Leu Gly Val Arg
            165                 170                 175

576
acc atg ttt aac ctg tta ggg ccg atg acg aat ccg gcc ggg gcc aaa
Thr Met Phe Asn Leu Leu Gly Pro Met Thr Asn Pro Ala Gly Ala Lys
        180                 185                 190

624
cgc cag gtg atg ggc gtg ttt cac cgc gat tta gtg cca ttg ctg gcg
Arg Gln Val Met Gly Val Phe His Arg Asp Leu Val Pro Leu Leu Ala
    195                 200                 205

672
caa acc ctg caa aaa ttg ggt agc gag cac gtg atg gtg gtg cat agt
Gln Thr Leu Gln Lys Leu Gly Ser Glu His Val Met Val Val His Ser
210                 215                 220

720
gct gat gaa atg gat gaa atc tct ttt tct gcg gac acc tat gtg gcc
Ala Asp Glu Met Asp Glu Ile Ser Phe Ser Ala Asp Thr Tyr Val Ala
225                 230                 235                 240

768
gaa ttg aaa aat ggc aac atc aat gaa tat atc ctg aat cct gca caa
Glu Leu Lys Asn Gly Asn Ile Asn Glu Tyr Ile Leu Asn Pro Ala Gln
                245                 250                 255

816
ttt ggc atg ccg tta cat gat atc aac agt atc cgt gtt gaa agt gca
Phe Gly Met Pro Leu His Asp Ile Asn Ser Ile Arg Val Glu Ser Ala
            260                 265                 270

864
caa cat tcc agc gag att atc ctc ggt ttg cta tct ggt gaa aaa ggc
Gln His Ser Ser Glu Ile Ile Leu Gly Leu Leu Ser Gly Glu Lys Gly
        275                 280                 285

912
cct gca aga gat atc gta ttg cta aac gca ggc gct gcg att tac gtc
Pro Ala Arg Asp Ile Val Leu Leu Asn Ala Gly Ala Ala Ile Tyr Val
    290                 295                 300

960
tct ggg ctg gta aat gat tta act tct ggc att gca caa gcg gcg caa
Ser Gly Leu Val Asn Asp Leu Thr Ser Gly Ile Ala Gln Ala Ala Gln
305                 310                 315                 320

1008
tcg att gat tca ggt gcg gct ttg aat aag ttg cag caa ctg aaa gct
Ser Ile Asp Ser Gly Ala Ala Leu Asn Lys Leu Gln Gln Leu Lys Ala
                325                 330                 335

1026
tta agt cag gcc aca tga
Leu Ser Gln Ala Thr
            340

<210> SEQ ID NO 20
<211> LENGTH: 341
<212> TYPE: PRT
<213> ORGANISM: Methylophilus methylotrophus

<400> SEQUENCE: 20

Met Ala Ile Thr Pro Lys Ile Ala Leu Gln Arg Leu Ile Asp His Thr
1               5                   10                  15

Asp Phe Thr His Asp Glu Met Leu Glu Ile Met Gln Ile Met Ser
            20                  25                  30

Gly Glu Phe Thr Gln Ile Gln Ile Ala Gly Phe Leu Ser Ala Leu Arg
        35                  40                  45

Val Lys Gly Glu Thr Val Thr Glu Ile Ala Ala Ala Gln Val Met
    50                  55                  60

Arg Glu Leu Ser Ser Lys Val Glu Ile Thr Asp Thr Arg His Leu Ile
65                  70                  75                  80

Asp Thr Cys Gly Thr Gly Gly Ala Pro Asn Lys Val Phe Asn Val Ser
                85                  90                  95

Thr Ala Ser Ala Phe Val Ala Ala Gly Ala Gly Ala Lys Ile Ala Lys
            100                 105                 110
```

His Gly Gly Arg Ala Ala Ser Ser Lys Ser Gly Ser Ala Asp Val Leu
            115                 120                 125

Glu Ala Leu Gly Val Asn Ile Val Leu Thr Pro Glu Gln Val Val Arg
        130                 135                 140

Cys Val Asn Glu Ala Gly Ile Gly Phe Met Phe Ala Pro Asn His His
145                 150                 155                 160

Ala Ala Met Lys Tyr Ala Ala Pro Val Arg Arg Glu Leu Gly Val Arg
                165                 170                 175

Thr Met Phe Asn Leu Leu Gly Pro Met Thr Asn Pro Ala Gly Ala Lys
            180                 185                 190

Arg Gln Val Met Gly Val Phe His Arg Asp Leu Val Pro Leu Leu Ala
        195                 200                 205

Gln Thr Leu Gln Lys Leu Gly Ser Glu His Val Met Val Val His Ser
    210                 215                 220

Ala Asp Glu Met Asp Glu Ile Ser Phe Ser Ala Asp Thr Tyr Val Ala
225                 230                 235                 240

Glu Leu Lys Asn Gly Asn Ile Asn Glu Tyr Ile Leu Asn Pro Ala Gln
                245                 250                 255

Phe Gly Met Pro Leu His Asp Ile Asn Ser Ile Arg Val Glu Ser Ala
            260                 265                 270

Gln His Ser Ser Glu Ile Ile Leu Gly Leu Leu Ser Gly Glu Lys Gly
        275                 280                 285

Pro Ala Arg Asp Ile Val Leu Leu Asn Ala Gly Ala Ala Ile Tyr Val
    290                 295                 300

Ser Gly Leu Val Asn Asp Leu Thr Ser Gly Ile Ala Gln Ala Ala Gln
305                 310                 315                 320

Ser Ile Asp Ser Gly Ala Ala Leu Asn Lys Leu Gln Gln Leu Lys Ala
                325                 330                 335

Leu Ser Gln Ala Thr
            340

<210> SEQ ID NO 21
<211> LENGTH: 648
<212> TYPE: DNA
<213> ORGANISM: Methylophilus methylotrophus
<220> FEATURE:
<221> NAME/KEY: CDS
<222> LOCATION: (1)..(648)
<223> OTHER INFORMATION:

<400> SEQUENCE: 21

```
atg aca aga acc agg gtt aaa att tgt ggt atc aca cgt cag cag gat        48
Met Thr Arg Thr Arg Val Lys Ile Cys Gly Ile Thr Arg Gln Gln Asp
1               5                   10                  15 gca tta gaa gcg att agt gca ggc gca gat gcg cta gga ttt gtg ttt        96
Ala Leu Glu Ala Ile Ser Ala Gly Ala Asp Ala Leu Gly Phe Val Phe
            20                  25                  30 tat gcc cct agc cca cgt gct gtc ctg ccc gct gag gtg cag gcg atc       144
Tyr Ala Pro Ser Pro Arg Ala Val Leu Pro Ala Glu Val Gln Ala Ile
        35                  40                  45 acg gcg atg ttg ccg cca ttc gtc agc aaa gtc ggt ttg ttt gtg aat       192
Thr Ala Met Leu Pro Pro Phe Val Ser Lys Val Gly Leu Phe Val Asn
    50                  55                  60 gca tca gcc agc gaa gtg cgt gag gcg att gtg acc gca ggc ctg gat       240
Ala Ser Ala Ser Glu Val Arg Glu Ala Ile Val Thr Ala Gly Leu Asp
65                  70                  75                  80 tgt ttg cag ttt cac ggc gat gaa tct gcg gac tat tgc gcg caa ttt       288
Cys Leu Gln Phe His Gly Asp Glu Ser Ala Asp Tyr Cys Ala Gln Phe
```

```
Cys Leu Gln Phe His Gly Asp Glu Ser Ala Asp Tyr Cys Ala Gln Phe
            85                  90                  95 aat ctg cca tat tac aaa gca atc cgc gtc aaa cca gag gta aat ttg      336
Asn Leu Pro Tyr Tyr Lys Ala Ile Arg Val Lys Pro Glu Val Asn Leu
            100                 105                 110 ata caa tgc gag ctt gat ttt gca tcg gcg act gca ttg ttg ctg gat      384
Ile Gln Cys Glu Leu Asp Phe Ala Ser Ala Thr Ala Leu Leu Leu Asp
            115                 120                 125 acc tat tca gaa aaa gcg gta ggt gga aca ggc gag gcc ttt gac tgg      432
Thr Tyr Ser Glu Lys Ala Val Gly Gly Thr Gly Glu Ala Phe Asp Trp
    130                 135                 140 tcg gtg att cct gct ggc atg caa aag ccg ctg gtt ctg gcg ggt ggt      480
Ser Val Ile Pro Ala Gly Met Gln Lys Pro Leu Val Leu Ala Gly Gly
145                 150                 155                 160 ttg aat cct gac aat gtg acc caa gcc atg cat cag gta cat cct tat      528
Leu Asn Pro Asp Asn Val Thr Gln Ala Met His Gln Val His Pro Tyr
                165                 170                 175 gct ttg gat gtc agt ggc ggt gtt gaa gta gaa aag gga ata aaa tcc      576
Ala Leu Asp Val Ser Gly Gly Val Glu Val Glu Lys Gly Ile Lys Ser
            180                 185                 190 gca caa aaa ata gct gca ttc atg cag cag gtg atg cag tgt gat gct      624
Ala Gln Lys Ile Ala Ala Phe Met Gln Gln Val Met Gln Cys Asp Ala
            195                 200                 205 gca cgt aat ggg tgg tta gag taa                                      648
Ala Arg Asn Gly Trp Leu Glu
        210                 215
```

<210> SEQ ID NO 22
<211> LENGTH: 215
<212> TYPE: PRT
<213> ORGANISM: Methylophilus methylotrophus

<400> SEQUENCE: 22

```
Met Thr Arg Thr Arg Val Lys Ile Cys Gly Ile Thr Arg Gln Gln Asp
1               5                   10                  15

Ala Leu Glu Ala Ile Ser Ala Gly Ala Asp Ala Leu Gly Phe Val Phe
            20                  25                  30

Tyr Ala Pro Ser Pro Arg Ala Val Leu Pro Ala Glu Val Gln Ala Ile
        35                  40                  45

Thr Ala Met Leu Pro Pro Phe Val Ser Lys Val Gly Leu Phe Val Asn
    50                  55                  60

Ala Ser Ala Ser Glu Val Arg Glu Ala Ile Val Thr Ala Gly Leu Asp
65                  70                  75                  80

Cys Leu Gln Phe His Gly Asp Glu Ser Ala Asp Tyr Cys Ala Gln Phe
            85                  90                  95

Asn Leu Pro Tyr Tyr Lys Ala Ile Arg Val Lys Pro Glu Val Asn Leu
            100                 105                 110

Ile Gln Cys Glu Leu Asp Phe Ala Ser Ala Thr Ala Leu Leu Leu Asp
            115                 120                 125

Thr Tyr Ser Glu Lys Ala Val Gly Gly Thr Gly Glu Ala Phe Asp Trp
    130                 135                 140

Ser Val Ile Pro Ala Gly Met Gln Lys Pro Leu Val Leu Ala Gly Gly
145                 150                 155                 160

Leu Asn Pro Asp Asn Val Thr Gln Ala Met His Gln Val His Pro Tyr
                165                 170                 175

Ala Leu Asp Val Ser Gly Gly Val Glu Val Glu Lys Gly Ile Lys Ser
            180                 185                 190
```

```
Ala Gln Lys Ile Ala Ala Phe Met Gln Gln Val Met Gln Cys Asp Ala
        195                 200                 205

Ala Arg Asn Gly Trp Leu Glu
    210                 215

<210> SEQ ID NO 23
<211> LENGTH: 618
<212> TYPE: DNA
<213> ORGANISM: Methylophilus methylotrophus
<220> FEATURE:
<221> NAME/KEY: CDS
<222> LOCATION: (1)..(618)
<223> OTHER INFORMATION:

<400> SEQUENCE: 23 atg agt gat att tta aat aaa atc ctg gcg aca aaa gcc gaa gag atc      48
Met Ser Asp Ile Leu Asn Lys Ile Leu Ala Thr Lys Ala Glu Glu Ile
1               5                   10                  15 gcg aca gca caa gcc aag ctg cca ttg gcc gag gtg cag gcg ctc gca      96
Ala Thr Ala Gln Ala Lys Leu Pro Leu Ala Glu Val Gln Ala Leu Ala
            20                  25                  30 act cga caa gcg cct gcg cgt gat ttt gtc ggt gcg att cgc agc aag     144
Thr Arg Gln Ala Pro Ala Arg Asp Phe Val Gly Ala Ile Arg Ser Lys
        35                  40                  45 att gcc gca ggc aaa gcc gcc gtg att gcc gaa att aaa aaa gcc agt     192
Ile Ala Ala Gly Lys Ala Ala Val Ile Ala Glu Ile Lys Lys Ala Ser
    50                  55                  60 cct tcc aaa ggt gtg atc cgt gcc gac ttt aaa cct gca gaa att gct     240
Pro Ser Lys Gly Val Ile Arg Ala Asp Phe Lys Pro Ala Glu Ile Ala
65                  70                  75                  80 gcc agc tat gaa cta ggc ggc gca gca tgc ttg tct gtg cta acc gac     288
Ala Ser Tyr Glu Leu Gly Gly Ala Ala Cys Leu Ser Val Leu Thr Asp
                85                  90                  95 gag caa tac ttc cag ggt tcg gcc gat tac ctc aaa caa gcg cgg gcc     336
Glu Gln Tyr Phe Gln Gly Ser Ala Asp Tyr Leu Lys Gln Ala Arg Ala
            100                 105                 110 gtg tgc agc ctg ccc gtg tta cgc aaa gat ttt atg ata gat gaa tac     384
Val Cys Ser Leu Pro Val Leu Arg Lys Asp Phe Met Ile Asp Glu Tyr
        115                 120                 125 cag gtc tat gaa gca cgt gcc atg ggt gcg gat tgt att ctg ctg att     432
Gln Val Tyr Glu Ala Arg Ala Met Gly Ala Asp Cys Ile Leu Leu Ile
    130                 135                 140 gct gct gcg ctt acg ttg gcc caa atg cag caa ctg gaa agt gtt gca     480
Ala Ala Ala Leu Thr Leu Ala Gln Met Gln Gln Leu Glu Ser Val Ala
145                 150                 155                 160 cac agt ctg ggc atg gca gta ttg gta gaa gtg cac aac ggt gaa gaa     528
His Ser Leu Gly Met Ala Val Leu Val Glu Val His Asn Gly Glu Glu
                165                 170                 175 ctg gcg caa gct att cag ctg acc acg cca tta cta ggc att aat aac     576
Leu Ala Gln Ala Ile Gln Leu Thr Thr Pro Leu Leu Gly Ile Asn Asn
            180                 185                 190 cga acc tgc gca cgt ttg aag tca cgc tgg ata cca cat tag             618
Arg Thr Cys Ala Arg Leu Lys Ser Arg Trp Ile Pro His
        195                 200                 205

<210> SEQ ID NO 24
<211> LENGTH: 205
<212> TYPE: PRT
<213> ORGANISM: Methylophilus methylotrophus

<400> SEQUENCE: 24

Met Ser Asp Ile Leu Asn Lys Ile Leu Ala Thr Lys Ala Glu Glu Ile
```

```
                1               5                  10                  15
            Ala Thr Ala Gln Ala Lys Leu Pro Leu Ala Glu Val Gln Ala Leu Ala
                        20                  25                  30

Thr Arg Gln Ala Pro Ala Arg Asp Phe Val Gly Ala Ile Arg Ser Lys
                        35                  40                  45

Ile Ala Ala Gly Lys Ala Ala Val Ile Ala Glu Ile Lys Lys Ala Ser
                 50                  55                  60

Pro Ser Lys Gly Val Ile Arg Ala Asp Phe Lys Pro Ala Glu Ile Ala
             65                  70                  75                  80

Ala Ser Tyr Glu Leu Gly Gly Ala Ala Cys Leu Ser Val Leu Thr Asp
                             85                  90                  95

Glu Gln Tyr Phe Gln Gly Ser Ala Asp Tyr Leu Lys Gln Ala Arg Ala
                        100                 105                 110

Val Cys Ser Leu Pro Val Leu Arg Lys Asp Phe Met Ile Asp Glu Tyr
                        115                 120                 125

Gln Val Tyr Glu Ala Arg Ala Met Gly Ala Asp Cys Ile Leu Leu Ile
                    130                 135                 140

Ala Ala Ala Leu Thr Leu Ala Gln Met Gln Gln Leu Glu Ser Val Ala
            145                 150                 155                 160

His Ser Leu Gly Met Ala Val Leu Val Glu Val His Asn Gly Glu Glu
                            165                  170                 175

Leu Ala Gln Ala Ile Gln Leu Thr Thr Pro Leu Leu Gly Ile Asn Asn
                        180                 185                 190

Arg Thr Cys Ala Arg Leu Lys Ser Arg Trp Ile Pro His
                        195                 200                 205

<210> SEQ ID NO 25
<211> LENGTH: 1203
<212> TYPE: DNA
<213> ORGANISM: Methylophilus methylotrophus
<220> FEATURE:
<221> NAME/KEY: CDS
<222> LOCATION: (1)..(1203)
<223> OTHER INFORMATION:

<400> SEQUENCE: 25 atg aaa gtc tat gac atg cct gat gag cgc ggc cac ttt gga cct ttt        48
Met Lys Val Tyr Asp Met Pro Asp Glu Arg Gly His Phe Gly Pro Phe
 1               5                  10                  15 ggt ggc gtt ttt gtt gca gaa acc ttg gta gag gcc ttg gaa gaa ctg        96
Gly Gly Val Phe Val Ala Glu Thr Leu Val Glu Ala Leu Glu Glu Leu
                20                  25                  30 cgc gtg atg tat gaa aaa tat cgt cat gac cct gaa ttc ctg gca gaa       144
Arg Val Met Tyr Glu Lys Tyr Arg His Asp Pro Glu Phe Leu Ala Glu
            35                  40                  45 ttt gct tac gac ctc aag cat ttt gtt ggt cgc ccc agc ccg att tac       192
Phe Ala Tyr Asp Leu Lys His Phe Val Gly Arg Pro Ser Pro Ile Tyr
         50                  55                  60 cat gcc aag cgt ctt tcc gaa aag gtg ggt ggc gcg caa att tat ctt       240
His Ala Lys Arg Leu Ser Glu Lys Val Gly Gly Ala Gln Ile Tyr Leu
 65                  70                  75                  80 aag cgc gaa gat tta aac cac acc ggt gcg cat aaa atc aat aat aca       288
Lys Arg Glu Asp Leu Asn His Thr Gly Ala His Lys Ile Asn Asn Thr
                 85                  90                  95 atc ggc cag gct ttg ttg gcc aag cgc atg ggc aag cct cgc gtc atc       336
Ile Gly Gln Ala Leu Leu Ala Lys Arg Met Gly Lys Pro Arg Val Ile
            100                 105                 110 gcc gaa acc ggt gcc gga cag cat ggc gtg gca acg gcc acg att gct       384
Ala Glu Thr Gly Ala Gly Gln His Gly Val Ala Thr Ala Thr Ile Ala
```

-continued

| | | |
|---|---|---|
| Ala Glu Thr Gly Ala Gly Gln His Gly Val Ala Thr Ala Thr Ile Ala<br>115                       120                    125 | | |
| gcg cgt tta ggc ttg gaa tgt gtt gtc tat atg ggt gcc gaa gat gtc<br>Ala Arg Leu Gly Leu Glu Cys Val Val Tyr Met Gly Ala Glu Asp Val<br>    130                     135                    140 | 432 |
| aaa cgc cag gca ccg aac gtc ttt cgc atg aag ctg ctg ggg gcc acg<br>Lys Arg Gln Ala Pro Asn Val Phe Arg Met Lys Leu Leu Gly Ala Thr<br>145                     150                   155                160 | 480 |
| gta gtc ccc gtc gaa agt ggt tcc aaa acc ctg aaa gat gca ttg aat<br>Val Val Pro Val Glu Ser Gly Ser Lys Thr Leu Lys Asp Ala Leu Asn<br>                     165                    170                 175 | 528 |
| gaa gcc atg cgt gac tgg gtc acc aat atc tcc aat act ttc tat att<br>Glu Ala Met Arg Asp Trp Val Thr Asn Ile Ser Asn Thr Phe Tyr Ile<br>                          180                    185                190 | 576 |
| atc ggt act gtg gca ggc cct cat ccc tac ccg atg atg gtg cgt gat<br>Ile Gly Thr Val Ala Gly Pro His Pro Tyr Pro Met Met Val Arg Asp<br>                 195                    200                   205 | 624 |
| ttt cag gcg gtg att ggt att gaa gcc aaa gag caa atg cag gaa atg<br>Phe Gln Ala Val Ile Gly Ile Glu Ala Lys Glu Gln Met Gln Glu Met<br>210                     215                    220 | 672 |
| ata ggc cga cag cca gat gcc gtg gtg gcc tgt gtt ggc ggt ggt tcc<br>Ile Gly Arg Gln Pro Asp Ala Val Val Ala Cys Val Gly Gly Gly Ser<br>225                     230                   235                240 | 720 |
| aat gca atg ggc att ttc tat cct tac att gat gtg gaa ggt gta cgc<br>Asn Ala Met Gly Ile Phe Tyr Pro Tyr Ile Asp Val Glu Gly Val Arg<br>                          245                    250                255 | 768 |
| ctg ata ggt gtg gag gct ggc gga cat ggt ctg cac aca ggc cag cat<br>Leu Ile Gly Val Glu Ala Gly Gly His Gly Leu His Thr Gly Gln His<br>                 260                    265                  270 | 816 |
| gcg gcg cca ctg acc gca aat agc ccg att ggt gtg ttg cat ggt aac<br>Ala Ala Pro Leu Thr Ala Asn Ser Pro Ile Gly Val Leu His Gly Asn<br>275                     280                    285 | 864 |
| cgt act tac ctc atg cag gac gaa gat ggc aat atc atc gag acg cat<br>Arg Thr Tyr Leu Met Gln Asp Glu Asp Gly Asn Ile Ile Glu Thr His<br>    290                     295                    300 | 912 |
| tcg att tct gca ggt ctc gat tat ccg ggt gta ggt cct gag cat gcc<br>Ser Ile Ser Ala Gly Leu Asp Tyr Pro Gly Val Gly Pro Glu His Ala<br>305                     310                    315                320 | 960 |
| tgg tta aaa gat atc aag cgt gct gaa tat gtg gcc att acc gac gat<br>Trp Leu Lys Asp Ile Lys Arg Ala Glu Tyr Val Ala Ile Thr Asp Asp<br>                          325                    330                335 | 1008 |
| gag gcc atg gcg gcc ttt cat aat ctg tgc cgt act gaa ggc att att<br>Glu Ala Met Ala Ala Phe His Asn Leu Cys Arg Thr Glu Gly Ile Ile<br>                 340                    345                  350 | 1056 |
| cct gcc atg gaa acc agt cat gct cta gca cat gcc gag aaa atg gca<br>Pro Ala Met Glu Thr Ser His Ala Leu Ala His Ala Glu Lys Met Ala<br>355                     360                    365 | 1104 |
| aaa acc atg tcc cca gac cag gtc gtt ctg gtg aac ctg tct ggc cgt<br>Lys Thr Met Ser Pro Asp Gln Val Val Leu Val Asn Leu Ser Gly Arg<br>    370                     375                    380 | 1152 |
| ggt gac aaa gac att aat acg gtg gca cgc ctg gct aac att aca ctg<br>Gly Asp Lys Asp Ile Asn Thr Val Ala Arg Leu Ala Asn Ile Thr Leu<br>385                     390                    395                400 | 1200 |
| tga | 1203 |

<210> SEQ ID NO 26
<211> LENGTH: 400
<212> TYPE: PRT
<213> ORGANISM: Methylophilus methylotrophus -continued

```
<400> SEQUENCE: 26

Met Lys Val Tyr Asp Met Pro Asp Glu Arg Gly His Phe Gly Pro Phe
1               5                   10                  15

Gly Gly Val Phe Val Ala Glu Thr Leu Val Glu Ala Leu Glu Glu Leu
            20                  25                  30

Arg Val Met Tyr Glu Lys Tyr Arg His Asp Pro Glu Phe Leu Ala Glu
        35                  40                  45

Phe Ala Tyr Asp Leu Lys His Phe Val Gly Arg Pro Ser Pro Ile Tyr
    50                  55                  60

His Ala Lys Arg Leu Ser Glu Lys Val Gly Ala Gln Ile Tyr Leu
65                  70                  75                  80

Lys Arg Glu Asp Leu Asn His Thr Gly Ala His Lys Ile Asn Asn Thr
                85                  90                  95

Ile Gly Gln Ala Leu Leu Ala Lys Arg Met Gly Lys Pro Arg Val Ile
            100                 105                 110

Ala Glu Thr Gly Ala Gly Gln His Gly Val Ala Thr Ala Thr Ile Ala
        115                 120                 125

Ala Arg Leu Gly Leu Glu Cys Val Val Tyr Met Gly Ala Glu Asp Val
    130                 135                 140

Lys Arg Gln Ala Pro Asn Val Phe Arg Met Lys Leu Leu Gly Ala Thr
145                 150                 155                 160

Val Val Pro Val Glu Ser Gly Ser Lys Thr Leu Lys Asp Ala Leu Asn
                165                 170                 175

Glu Ala Met Arg Asp Trp Val Thr Asn Ile Ser Asn Thr Phe Tyr Ile
            180                 185                 190

Ile Gly Thr Val Ala Gly Pro His Pro Tyr Pro Met Met Val Arg Asp
        195                 200                 205

Phe Gln Ala Val Ile Gly Ile Glu Ala Lys Glu Gln Met Gln Glu Met
    210                 215                 220

Ile Gly Arg Gln Pro Asp Ala Val Val Ala Cys Val Gly Gly Gly Ser
225                 230                 235                 240

Asn Ala Met Gly Ile Phe Tyr Pro Tyr Ile Asp Val Glu Gly Val Arg
                245                 250                 255

Leu Ile Gly Val Glu Ala Gly Gly His Gly Leu His Thr Gly Gln His
            260                 265                 270

Ala Ala Pro Leu Thr Ala Asn Ser Pro Ile Gly Val Leu His Gly Asn
        275                 280                 285

Arg Thr Tyr Leu Met Gln Asp Glu Asp Gly Asn Ile Ile Glu Thr His
    290                 295                 300

Ser Ile Ser Ala Gly Leu Asp Tyr Pro Gly Val Gly Pro Glu His Ala
305                 310                 315                 320

Trp Leu Lys Asp Ile Lys Arg Ala Glu Tyr Val Ala Ile Thr Asp Asp
                325                 330                 335

Glu Ala Met Ala Ala Phe His Asn Leu Cys Arg Thr Glu Gly Ile Ile
            340                 345                 350

Pro Ala Met Glu Thr Ser His Ala Leu Ala His Ala Glu Lys Met Ala
        355                 360                 365

Lys Thr Met Ser Pro Asp Gln Val Val Leu Val Asn Leu Ser Gly Arg
    370                 375                 380

Gly Asp Lys Asp Ile Asn Thr Val Ala Arg Leu Ala Asn Ile Thr Leu
385                 390                 395                 400

<210> SEQ ID NO 27
```

-continued

```
<211> LENGTH: 801
<212> TYPE: DNA
<213> ORGANISM: Methylophilus methylotrophus
<220> FEATURE:
<221> NAME/KEY: CDS
<222> LOCATION: (1)..(801)
<223> OTHER INFORMATION:

<400> SEQUENCE: 27 atg tca cgc att caa tct gta ttt tcc gca ctc aaa gcg caa ggc aaa        48
Met Ser Arg Ile Gln Ser Val Phe Ser Ala Leu Lys Ala Gln Gly Lys
1               5                   10                  15 aag gcg ctg att ccg tat atc acg gca ggt gat ccg cat cct gac caa        96
Lys Ala Leu Ile Pro Tyr Ile Thr Ala Gly Asp Pro His Pro Asp Gln
                20                  25                  30 aca gtc acg ctg atg cat acg ttg gta agt tcc ggg gca gac atg att       144
Thr Val Thr Leu Met His Thr Leu Val Ser Ser Gly Ala Asp Met Ile
            35                  40                  45 gag ctt ggc gtc ccg ttt tct gac ccg atg gcc gac ggt cct gtt atc       192
Glu Leu Gly Val Pro Phe Ser Asp Pro Met Ala Asp Gly Pro Val Ile
        50                  55                  60 cag cgc gcc agc gag cgc gcc cta gtg cac aaa atg ggg ctg cgt aag       240
Gln Arg Ala Ser Glu Arg Ala Leu Val His Lys Met Gly Leu Arg Lys
65                  70                  75                  80 gta ctg gaa atg gtg aaa acc ttt cgt gaa acc aat caa gcg acg ccg       288
Val Leu Glu Met Val Lys Thr Phe Arg Glu Thr Asn Gln Ala Thr Pro
                85                  90                  95 att gtg ctg atg ggc tat gca aat ccg att gaa gcc atg ggg agt gcg       336
Ile Val Leu Met Gly Tyr Ala Asn Pro Ile Glu Ala Met Gly Ser Ala
                100                 105                 110 aaa ttc gtc gca ttg gct aaa gag gca ggt gtc gat ggc gta ctg acg       384
Lys Phe Val Ala Leu Ala Lys Glu Ala Gly Val Asp Gly Val Leu Thr
            115                 120                 125 gtg gat tat cca cca gaa gag tgc gaa gca ttt aat cgc gag ctt gcc       432
Val Asp Tyr Pro Pro Glu Glu Cys Glu Ala Phe Asn Arg Glu Leu Ala
        130                 135                 140 gat gcg ggg atg gat agt att ttc ctg ttg tcg cct acg aca gaa cca       480
Asp Ala Gly Met Asp Ser Ile Phe Leu Leu Ser Pro Thr Thr Glu Pro
145                 150                 155                 160 tcg cgt acg gag ttg att gtg aag cag gcg acg ggc ttt ctt tac tat       528
Ser Arg Thr Glu Leu Ile Val Lys Gln Ala Thr Gly Phe Leu Tyr Tyr
                165                 170                 175 gtt tcc ctc aag ggc gtg acg ggt gct gca aac ctg gat att act gaa       576
Val Ser Leu Lys Gly Val Thr Gly Ala Ala Asn Leu Asp Ile Thr Glu
                180                 185                 190 gtt aaa aag cgt gtc gca gag att cgc aag caa acc acg ctg cca atc       624
Val Lys Lys Arg Val Ala Glu Ile Arg Lys Gln Thr Thr Leu Pro Ile
            195                 200                 205 ggg gtt ggt ttt gga gtt aaa gat gct gcg act gcc cgt gaa gtg gct       672
Gly Val Gly Phe Gly Val Lys Asp Ala Ala Thr Ala Arg Glu Val Ala
        210                 215                 220 gcg ata gct gac gcg gta gtg gtt ggt agc cgt atg gtg ctg gcg att       720
Ala Ile Ala Asp Ala Val Val Val Gly Ser Arg Met Val Leu Ala Ile
225                 230                 235                 240 gag ggg tcg gat gca aat aat ctg atc agt aat gtg cag aca tta atg       768
Glu Gly Ser Asp Ala Asn Asn Leu Ile Ser Asn Val Gln Thr Leu Met
                245                 250                 255 aag gaa ttg cgt act gcg att gat tcc gta tag                           801
Lys Glu Leu Arg Thr Ala Ile Asp Ser Val
                260                 265
```

<210> SEQ ID NO 28
<211> LENGTH: 266
<212> TYPE: PRT
<213> ORGANISM: Methylophilus methylotrophus

<400> SEQUENCE: 28

```
Met Ser Arg Ile Gln Ser Val Phe Ser Ala Leu Lys Ala Gln Gly Lys
1               5                   10                  15

Lys Ala Leu Ile Pro Tyr Ile Thr Ala Gly Asp Pro His Pro Asp Gln
            20                  25                  30

Thr Val Thr Leu Met His Thr Leu Val Ser Ser Gly Ala Asp Met Ile
        35                  40                  45

Glu Leu Gly Val Pro Phe Ser Asp Pro Met Ala Asp Gly Pro Val Ile
    50                  55                  60

Gln Arg Ala Ser Glu Arg Ala Leu Val His Lys Met Gly Leu Arg Lys
65                  70                  75                  80

Val Leu Glu Met Val Lys Thr Phe Arg Glu Thr Asn Gln Ala Thr Pro
                85                  90                  95

Ile Val Leu Met Gly Tyr Ala Asn Pro Ile Glu Ala Met Gly Ser Ala
            100                 105                 110

Lys Phe Val Ala Leu Ala Lys Glu Ala Gly Val Asp Gly Val Leu Thr
        115                 120                 125

Val Asp Tyr Pro Pro Glu Glu Cys Glu Ala Phe Asn Arg Glu Leu Ala
    130                 135                 140

Asp Ala Gly Met Asp Ser Ile Phe Leu Leu Ser Pro Thr Thr Glu Pro
145                 150                 155                 160

Ser Arg Thr Glu Leu Ile Val Lys Gln Ala Thr Gly Phe Leu Tyr Tyr
                165                 170                 175

Val Ser Leu Lys Gly Val Thr Gly Ala Ala Asn Leu Asp Ile Thr Glu
            180                 185                 190

Val Lys Lys Arg Val Ala Glu Ile Arg Lys Gln Thr Thr Leu Pro Ile
        195                 200                 205

Gly Val Gly Phe Gly Val Lys Asp Ala Ala Thr Ala Arg Glu Val Ala
    210                 215                 220

Ala Ile Ala Asp Ala Val Val Gly Ser Arg Met Val Leu Ala Ile
225                 230                 235                 240

Glu Gly Ser Asp Ala Asn Asn Leu Ile Ser Asn Val Gln Thr Leu Met
                245                 250                 255

Lys Glu Leu Arg Thr Ala Ile Asp Ser Val
            260                 265
```

<210> SEQ ID NO 29
<211> LENGTH: 1419
<212> TYPE: DNA
<213> ORGANISM: Methylophilus methylotrophus
<220> FEATURE:
<221> NAME/KEY: CDS
<222> LOCATION: (1)..(1419)
<223> OTHER INFORMATION:

<400> SEQUENCE: 29

```
gtg ttt aag aaa att tta gtc gcg aat cgc ggt gaa att gcg gta cgt    48
Val Phe Lys Lys Ile Leu Val Ala Asn Arg Gly Glu Ile Ala Val Arg
1               5                   10                  15 att gtg cgc gcc tgc tcg gaa atg ggc atc aaa tcg gtc gcc att tat    96
Ile Val Arg Ala Cys Ser Glu Met Gly Ile Lys Ser Val Ala Ile Tyr
            20                  25                  30 tcc gac gct gac cgt cat gcc ctg cat gtc aaa aaa gcc gac gaa gct   144
```

-continued

```
                Ser Asp Ala Asp Arg His Ala Leu His Val Lys Lys Ala Asp Glu Ala
                    35                  40                  45 tat aac att ggt tcc gat cct gta gca ggc tat ctg aac gca cat aat        192
Tyr Asn Ile Gly Ser Asp Pro Val Ala Gly Tyr Leu Asn Ala His Asn
 50                  55                  60 att gtg aat att gcc gtg gct gct ggt tgt gat gcc ttg cat cca ggc        240
Ile Val Asn Ile Ala Val Ala Ala Gly Cys Asp Ala Leu His Pro Gly
 65                  70                  75                  80 tat ggc ttc ctt tca gaa aat cct gaa ttg gct gag gtt tgc gcc cgc        288
Tyr Gly Phe Leu Ser Glu Asn Pro Glu Leu Ala Glu Val Cys Ala Arg
                 85                  90                  95 cgc ggc atc aag ttt att ggc cca gag gca gac gtt atc cgc cag atg        336
Arg Gly Ile Lys Phe Ile Gly Pro Glu Ala Asp Val Ile Arg Gln Met
            100                 105                 110 ggt gac aag att cag gcg cgt aac gcc atg att aat gca ggt att ccc        384
Gly Asp Lys Ile Gln Ala Arg Asn Ala Met Ile Asn Ala Gly Ile Pro
        115                 120                 125 tgt gta ccg ggc agc gat ggc aac ctc gaa tct gtt gac gcc gcc atc        432
Cys Val Pro Gly Ser Asp Gly Asn Leu Glu Ser Val Asp Ala Ala Ile
    130                 135                 140 aag ctg gca aat aaa ata ggc tat cca gtg atg ctg aaa gcc acc aat        480
Lys Leu Ala Asn Lys Ile Gly Tyr Pro Val Met Leu Lys Ala Thr Asn
145                 150                 155                 160 ggt ggt ggt ggc cgt ggt att cgc cgt tgc gac aac gaa aaa gaa tta        528
Gly Gly Gly Gly Arg Gly Ile Arg Arg Cys Asp Asn Glu Lys Glu Leu
                165                 170                 175 tta agc aat tat gac cgt gtc att tct gaa gcc agc aaa gcc ttc ggc        576
Leu Ser Asn Tyr Asp Arg Val Ile Ser Glu Ala Ser Lys Ala Phe Gly
            180                 185                 190 aag ccg gaa gtg ttc ctt gaa aaa tgt gtg gtt cat cca cgc cat atc        624
Lys Pro Glu Val Phe Leu Glu Lys Cys Val Val His Pro Arg His Ile
        195                 200                 205 gaa gtg cag gtg ctg gct gat tcc cat ggc aat gtc att cac ctg ttt        672
Glu Val Gln Val Leu Ala Asp Ser His Gly Asn Val Ile His Leu Phe
    210                 215                 220 gag cgt gac tgc tct atc cag cgc cgc aat cag aag ctg att gaa atc        720
Glu Arg Asp Cys Ser Ile Gln Arg Arg Asn Gln Lys Leu Ile Glu Ile
225                 230                 235                 240 gcc ccg tca cca caa ctg acg cag gca cag cgt gaa tat att ggc ggg        768
Ala Pro Ser Pro Gln Leu Thr Gln Ala Gln Arg Glu Tyr Ile Gly Gly
                245                 250                 255 ctg ggt gtc aag gca gcc aaa gca gtg ggt tat gaa aat gcc ggc aca        816
Leu Gly Val Lys Ala Ala Lys Ala Val Gly Tyr Glu Asn Ala Gly Thr
            260                 265                 270 gtc gag ttt ctg ctc gac tct gac aat aat ttc tat ttc atg gaa atg        864
Val Glu Phe Leu Leu Asp Ser Asp Asn Asn Phe Tyr Phe Met Glu Met
        275                 280                 285 aac acc cgc ttg cag gtg gaa cat act gtg act gaa acc att acc ggt        912
Asn Thr Arg Leu Gln Val Glu His Thr Val Thr Glu Thr Ile Thr Gly
    290                 295                 300 gtt gat atc gtt cag cag cag atc cgc gtg gcg gca ggc ctg cct ttg        960
Val Asp Ile Val Gln Gln Gln Ile Arg Val Ala Ala Gly Leu Pro Leu
305                 310                 315                 320 cag tac aag caa agc gaa att gcg ttc cgt ggt tat gcc atg gag tac       1008
Gln Tyr Lys Gln Ser Glu Ile Ala Phe Arg Gly Tyr Ala Met Glu Tyr
                325                 330                 335 cgc atc aac gcc gaa gac ccg caa aaa gac ttc ttg cca agc ttt ggt       1056
Arg Ile Asn Ala Glu Asp Pro Gln Lys Asp Phe Leu Pro Ser Phe Gly
            340                 345                 350
```

-continued

```
aag att aca cgc tac tac gcg ccc ggc ggt cct ggc gta cgt atg gat     1104
Lys Ile Thr Arg Tyr Tyr Ala Pro Gly Gly Pro Gly Val Arg Met Asp
        355                 360                 365 gca gct att tat agc ggg tat gtc att cca cct tac tat gac tcc atg     1152
Ala Ala Ile Tyr Ser Gly Tyr Val Ile Pro Pro Tyr Tyr Asp Ser Met
370                 375                 380 tgt gcc aag ctg acg gtt tgg gcg ctg gat tgg gaa ggc gtg atc gag     1200
Cys Ala Lys Leu Thr Val Trp Ala Leu Asp Trp Glu Gly Val Ile Glu
385                 390                 395                 400 cgc ggc cgt cgt gcg ctg aac gac atg att gtg tat ggc gtc aaa aca     1248
Arg Gly Arg Arg Ala Leu Asn Asp Met Ile Val Tyr Gly Val Lys Thr
                405                 410                 415 acg att cct tat tac cag caa atc atg caa cat ccg gat ttc cgt gca     1296
Thr Ile Pro Tyr Tyr Gln Gln Ile Met Gln His Pro Asp Phe Arg Ala
            420                 425                 430 gct gac ttt aat acc agc ttt gtg gaa caa cat ccc gag ctg acg caa     1344
Ala Asp Phe Asn Thr Ser Phe Val Glu Gln His Pro Glu Leu Thr Gln
        435                 440                 445 tat gac gtc gga tta ccg aaa gaa ttg atg gct gcg gcg att gct gca     1392
Tyr Asp Val Gly Leu Pro Lys Glu Leu Met Ala Ala Ala Ile Ala Ala
450                 455                 460 gca atc gcc gcc cac gaa ggc att tga                                 1419
Ala Ile Ala Ala His Glu Gly Ile
465                 470
```

<210> SEQ ID NO 30
<211> LENGTH: 472
<212> TYPE: PRT
<213> ORGANISM: Methylophilus methylotrophus

<400> SEQUENCE: 30

```
Val Phe Lys Lys Ile Leu Val Ala Asn Arg Gly Glu Ile Ala Val Arg
1               5                   10                  15

Ile Val Arg Ala Cys Ser Glu Met Gly Ile Lys Ser Val Ala Ile Tyr
            20                  25                  30

Ser Asp Ala Asp Arg His Ala Leu His Val Lys Lys Ala Asp Glu Ala
        35                  40                  45

Tyr Asn Ile Gly Ser Asp Pro Val Ala Gly Tyr Leu Asn Ala His Asn
    50                  55                  60

Ile Val Asn Ile Ala Val Ala Ala Gly Cys Asp Ala Leu His Pro Gly
65                  70                  75                  80

Tyr Gly Phe Leu Ser Glu Asn Pro Glu Leu Ala Glu Val Cys Ala Arg
                85                  90                  95

Arg Gly Ile Lys Phe Ile Gly Pro Glu Ala Asp Val Ile Arg Gln Met
            100                 105                 110

Gly Asp Lys Ile Gln Ala Arg Asn Ala Met Ile Asn Ala Gly Ile Pro
        115                 120                 125

Cys Val Pro Gly Ser Asp Gly Asn Leu Glu Ser Val Asp Ala Ala Ile
    130                 135                 140

Lys Leu Ala Asn Lys Ile Gly Tyr Pro Val Met Leu Lys Ala Thr Asn
145                 150                 155                 160

Gly Gly Gly Gly Arg Gly Ile Arg Arg Cys Asp Asn Glu Lys Glu Leu
                165                 170                 175

Leu Ser Asn Tyr Asp Arg Val Ile Ser Glu Ala Ser Lys Ala Phe Gly
            180                 185                 190

Lys Pro Glu Val Phe Leu Glu Lys Cys Val Val His Pro Arg His Ile
        195                 200                 205
```

-continued

```
Glu Val Gln Val Leu Ala Asp Ser His Gly Asn Val Ile His Leu Phe
    210                 215                 220
Glu Arg Asp Cys Ser Ile Gln Arg Arg Asn Gln Lys Leu Ile Glu Ile
225                 230                 235                 240
Ala Pro Ser Pro Gln Leu Thr Gln Ala Gln Arg Glu Tyr Ile Gly Gly
                245                 250                 255
Leu Gly Val Lys Ala Ala Lys Ala Val Gly Tyr Glu Asn Ala Gly Thr
            260                 265                 270
Val Glu Phe Leu Leu Asp Ser Asp Asn Phe Tyr Phe Met Glu Met
        275                 280                 285
Asn Thr Arg Leu Gln Val Glu His Thr Val Thr Glu Thr Ile Thr Gly
290                 295                 300
Val Asp Ile Val Gln Gln Gln Ile Arg Val Ala Ala Gly Leu Pro Leu
305                 310                 315                 320
Gln Tyr Lys Gln Ser Glu Ile Ala Phe Arg Gly Tyr Ala Met Glu Tyr
                325                 330                 335
Arg Ile Asn Ala Glu Asp Pro Gln Lys Asp Phe Leu Pro Ser Phe Gly
            340                 345                 350
Lys Ile Thr Arg Tyr Tyr Ala Pro Gly Gly Pro Gly Val Arg Met Asp
        355                 360                 365
Ala Ala Ile Tyr Ser Gly Tyr Val Ile Pro Pro Tyr Tyr Asp Ser Met
370                 375                 380
Cys Ala Lys Leu Thr Val Trp Ala Leu Asp Trp Glu Gly Val Ile Glu
385                 390                 395                 400
Arg Gly Arg Arg Ala Leu Asn Asp Met Ile Val Tyr Gly Val Lys Thr
                405                 410                 415
Thr Ile Pro Tyr Tyr Gln Gln Ile Met Gln His Pro Asp Phe Arg Ala
            420                 425                 430
Ala Asp Phe Asn Thr Ser Phe Val Glu Gln His Pro Glu Leu Thr Gln
        435                 440                 445
Tyr Asp Val Gly Leu Pro Lys Glu Leu Met Ala Ala Ile Ala Ala
450                 455                 460
Ala Ile Ala Ala His Glu Gly Ile
465                 470

<210> SEQ ID NO 31
<211> LENGTH: 1848
<212> TYPE: DNA
<213> ORGANISM: Methylophilus methylotrophus
<220> FEATURE:
<221> NAME/KEY: CDS
<222> LOCATION: (1)..(1848)
<223> OTHER INFORMATION:

<400> SEQUENCE: 31 atg agc aaa ata cat gtc acc gaa ctc gtt tta aga gat gga cac caa      48
Met Ser Lys Ile His Val Thr Glu Leu Val Leu Arg Asp Gly His Gln
1               5                  10                  15 tcc ctg att gcg acg cgc atg cgt act gaa gat atg ctg cca atc gcc      96
Ser Leu Ile Ala Thr Arg Met Arg Thr Glu Asp Met Leu Pro Ile Ala
            20                  25                  30 agc aag ctg gat gac att ggt ttc tgg tcc ctg gaa gcc tgg ggc gga     144
Ser Lys Leu Asp Asp Ile Gly Phe Trp Ser Leu Glu Ala Trp Gly Gly
        35                  40                  45 gcg aca ttt gac gcc tgc gta cgc ttt ttg aaa gaa gat cca tgg gag     192
Ala Thr Phe Asp Ala Cys Val Arg Phe Leu Lys Glu Asp Pro Trp Glu
    50                  55                  60
```

-continued

| | | |
|---|---|---|
| cgt tta cgc agc ctg cgt aaa gcc ttg ccc aat acg cct atc aat atg<br>Arg Leu Arg Ser Leu Arg Lys Ala Leu Pro Asn Thr Pro Ile Asn Met<br>65                         70                    75                  80 | | 240 |
| ctt ctg cgt ggc cag aac ctg ttg ggt tac cgc cat tac tcg gac gat<br>Leu Leu Arg Gly Gln Asn Leu Leu Gly Tyr Arg His Tyr Ser Asp Asp<br>                        85                    90                  95 | | 288 |
| gtc gtc cac gcc ttt gtt aaa cag gcg gca gat acc ggt gtg gat gtg<br>Val Val His Ala Phe Val Lys Gln Ala Ala Asp Thr Gly Val Asp Val<br>              100                    105                   110 | | 336 |
| ttt cgt atc ttt gat gcg atg aat gac atc cgc aac ctg aca acc gcc<br>Phe Arg Ile Phe Asp Ala Met Asn Asp Ile Arg Asn Leu Thr Thr Ala<br>          115                    120                   125 | | 384 |
| atc aaa gcc gtt aaa gct gcg aaa aaa cac gca att ggt acg ctg tca<br>Ile Lys Ala Val Lys Ala Ala Lys Lys His Ala Ile Gly Thr Leu Ser<br>130                       135                  140 | | 432 |
| ttc acc act agc cca gtg cat gat gtc gcc tac ttt gta aac atg gcc<br>Phe Thr Thr Ser Pro Val His Asp Val Ala Tyr Phe Val Asn Met Ala<br>145                       150                   155                   160 | | 480 |
| aaa gag ctt gaa gcg cta ggt tgc gac agc att ggt gtg aaa gac atg<br>Lys Glu Leu Glu Ala Leu Gly Cys Asp Ser Ile Gly Val Lys Asp Met<br>              165                    170                   175 | | 528 |
| gcc ggc ctg ctc act cca acc atg gcc gct gaa ctg gtg aaa ggc ctc<br>Ala Gly Leu Leu Thr Pro Thr Met Ala Ala Glu Leu Val Lys Gly Leu<br>          180                    185                   190 | | 576 |
| aag gct gcc gtc agc gtg cct gta cac atg cac agc cat gcc acc tca<br>Lys Ala Ala Val Ser Val Pro Val His Met His Ser His Ala Thr Ser<br>              195                    200                   205 | | 624 |
| ggc ctt gcc agc atg gta ttg ctc aag agc gtg gaa aac ggc gta gat<br>Gly Leu Ala Ser Met Val Leu Leu Lys Ser Val Glu Asn Gly Val Asp<br>          210                    215                   220 | | 672 |
| att att gat acc tgc aat tct tct ttc tcc gaa ggt gcc agc cat cca<br>Ile Ile Asp Thr Cys Asn Ser Ser Phe Ser Glu Gly Ala Ser His Pro<br>225                       230                   235                   240 | | 720 |
| acg aca gag agc ctg gtt gcg gcc ctg aaa ggt act gaa tac gat acc<br>Thr Thr Glu Ser Leu Val Ala Ala Leu Lys Gly Thr Glu Tyr Asp Thr<br>              245                    250                   255 | | 768 |
| ggc ctt gat ctt ggc aaa ctg cag gaa att act gcc tac ttc aaa gaa<br>Gly Leu Asp Leu Gly Lys Leu Gln Glu Ile Thr Ala Tyr Phe Lys Glu<br>          260                    265                   270 | | 816 |
| gtg cgc aga aaa tac tgg cag ttt gaa agc gag ttc act ggg gta gat<br>Val Arg Arg Lys Tyr Trp Gln Phe Glu Ser Glu Phe Thr Gly Val Asp<br>              275                    280                   285 | | 864 |
| acc cgc gta ctg gtt aac cag gta ccc ggt ggc atg att tcc aac ctg<br>Thr Arg Val Leu Val Asn Gln Val Pro Gly Gly Met Ile Ser Asn Leu<br>290                       295                   300 | | 912 |
| tcc aac caa ctg aaa gaa caa ggc gca ctc aac cgc atg gat gaa gtg<br>Ser Asn Gln Leu Lys Glu Gln Gly Ala Leu Asn Arg Met Asp Glu Val<br>305                       310                   315                   320 | | 960 |
| ctg gcc gaa atc ccg cgt gtc cgt gaa gat ctg ggt tat cct cca tta<br>Leu Ala Glu Ile Pro Arg Val Arg Glu Asp Leu Gly Tyr Pro Pro Leu<br>                        325                    330                   335 | | 1008 |
| gtc acc cct act tca cag att gta ggg aca cag gcg gta tta aac gtc<br>Val Thr Pro Thr Ser Gln Ile Val Gly Thr Gln Ala Val Leu Asn Val<br>          340                    345                   350 | | 1056 |
| ttg acc ggt agc cgt tac aaa tcc atc act aat gaa gtg aaa aat tac<br>Leu Thr Gly Ser Arg Tyr Lys Ser Ile Thr Asn Glu Val Lys Asn Tyr<br>              355                    360                   365 | | 1104 |
| ctg ttg ggc caa tat ggt aaa gcg cct gca gcg gtg aat gct gat gtg<br>Leu Leu Gly Gln Tyr Gly Lys Ala Pro Ala Ala Val Asn Ala Asp Val<br>          370                    375                   380 | | 1152 |

-continued

| | | |
|---|---|---|
| cgc aaa cag gcc gta ggc gat gct gaa gtc atc acc tgc cgt cct gca<br>Arg Lys Gln Ala Val Gly Asp Ala Glu Val Ile Thr Cys Arg Pro Ala<br>385                             390                      395                  400 | 1200 |
| gat ttg ctg caa cca gaa atg gcc aga ttg caa tct gaa gcc gag cgt<br>Asp Leu Leu Gln Pro Glu Met Ala Arg Leu Gln Ser Glu Ala Glu Arg<br>                   405                      410                      415 | 1248 |
| ttc gcc aat aac gaa caa gac gta ctg acc tac gcc atg ttc ccg gat<br>Phe Ala Asn Asn Glu Gln Asp Val Leu Thr Tyr Ala Met Phe Pro Asp<br>             420                      425                      430 | 1296 |
| atc ggg cag act ttc ttg caa gag cgc aac gca ggt tcc ttg cag cca<br>Ile Gly Gln Thr Phe Leu Gln Glu Arg Asn Ala Gly Ser Leu Gln Pro<br>                   435                      440                      445 | 1344 |
| gaa caa ttg ctg agc aaa gaa gcc gtg acc cag caa act gcc gca gca<br>Glu Gln Leu Leu Ser Lys Glu Ala Val Thr Gln Gln Thr Ala Ala Ala<br>450                             455                      460 | 1392 |
| cgt tat gcg cct aac gaa ttc aac atc acc ctg cac ggc gag acc tac<br>Arg Tyr Ala Pro Asn Glu Phe Asn Ile Thr Leu His Gly Glu Thr Tyr<br>465                           470                      475                  480 | 1440 |
| cat atc aaa ctg aca ggt agc ggt cat gcc ggt gaa gag cgc aag cca<br>His Ile Lys Leu Thr Gly Ser Gly His Ala Gly Glu Glu Arg Lys Pro<br>                   485                      490                      495 | 1488 |
| tac tat gtc aaa gtc gac gga atc tct gaa gaa gtg ttt gta gaa acg<br>Tyr Tyr Val Lys Val Asp Gly Ile Ser Glu Glu Val Phe Val Glu Thr<br>             500                      505                      510 | 1536 |
| ctg agc gag atg gaa gtc agc ggg ggc aat tca aac ggc agc aag aaa<br>Leu Ser Glu Met Glu Val Ser Gly Gly Asn Ser Asn Gly Ser Lys Lys<br>                   515                      520                      525 | 1584 |
| aaa gca gca gcg gtg gct gcc agc ggc cgt cca cgg ccc aac cat cca<br>Lys Ala Ala Ala Val Ala Ala Ser Gly Arg Pro Arg Pro Asn His Pro<br>530                             535                      540 | 1632 |
| ggc tgt gtc acg act gca atg cca ggc acc att gtc act gtg aaa gtg<br>Gly Cys Val Thr Thr Ala Met Pro Gly Thr Ile Val Thr Val Lys Val<br>545                             550                      555                  560 | 1680 |
| aat gtc ggt gac aag gtc aat gct ggc gat ggc gtg ctg gtg att gag<br>Asn Val Gly Asp Lys Val Asn Ala Gly Asp Gly Val Leu Val Ile Glu<br>                   565                      570                      575 | 1728 |
| gca atg aaa atg gaa aac gaa atc cag gcc agt aaa tcc ggt act gta<br>Ala Met Lys Met Glu Asn Glu Ile Gln Ala Ser Lys Ser Gly Thr Val<br>             580                      585                      590 | 1776 |
| gtg gcg atc cat gtt gcc aaa ggt gac agt gtg acc ccg gac gaa aca<br>Val Ala Ile His Val Ala Lys Gly Asp Ser Val Thr Pro Asp Glu Thr<br>                   595                      600                      605 | 1824 |
| ctg att gaa att cag ccg gaa taa<br>Leu Ile Glu Ile Gln Pro Glu<br>610                             615 | 1848 |

<210> SEQ ID NO 32
<211> LENGTH: 615
<212> TYPE: PRT
<213> ORGANISM: Methylophilus methylotrophus

<400> SEQUENCE: 32

Met Ser Lys Ile His Val Thr Glu Leu Val Leu Arg Asp Gly His Gln
1                 5                    10                 15

Ser Leu Ile Ala Thr Arg Met Arg Thr Glu Asp Met Leu Pro Ile Ala
                 20                    25                 30

Ser Lys Leu Asp Asp Ile Gly Phe Trp Ser Leu Glu Ala Trp Gly Gly
                   35                    40                    45

Ala Thr Phe Asp Ala Cys Val Arg Phe Leu Lys Glu Asp Pro Trp Glu

-continued

```
                50                  55                  60
Arg Leu Arg Ser Leu Arg Lys Ala Leu Pro Asn Thr Pro Ile Asn Met
 65                  70                  75                  80

Leu Leu Arg Gly Gln Asn Leu Leu Gly Tyr Arg His Tyr Ser Asp Asp
                     85                  90                  95

Val Val His Ala Phe Val Lys Gln Ala Asp Thr Gly Val Asp Val
                100                 105                 110

Phe Arg Ile Phe Asp Ala Met Asn Asp Ile Arg Asn Leu Thr Thr Ala
                115                 120                 125

Ile Lys Ala Val Lys Ala Lys Lys His Ala Ile Gly Thr Leu Ser
130                 135                 140

Phe Thr Thr Ser Pro Val His Asp Val Ala Tyr Phe Val Asn Met Ala
145                 150                 155                 160

Lys Glu Leu Glu Ala Leu Gly Cys Asp Ser Ile Gly Val Lys Asp Met
                165                 170                 175

Ala Gly Leu Leu Thr Pro Thr Met Ala Ala Glu Leu Val Lys Gly Leu
                180                 185                 190

Lys Ala Ala Val Ser Val Pro Val His Met His Ser His Ala Thr Ser
                195                 200                 205

Gly Leu Ala Ser Met Val Leu Leu Lys Ser Val Glu Asn Gly Val Asp
210                 215                 220

Ile Ile Asp Thr Cys Asn Ser Ser Phe Ser Glu Gly Ala Ser His Pro
225                 230                 235                 240

Thr Thr Glu Ser Leu Val Ala Ala Leu Lys Gly Thr Glu Tyr Asp Thr
                245                 250                 255

Gly Leu Asp Leu Gly Lys Leu Gln Glu Ile Thr Ala Tyr Phe Lys Glu
                260                 265                 270

Val Arg Arg Lys Tyr Trp Gln Phe Glu Ser Glu Phe Thr Gly Val Asp
                275                 280                 285

Thr Arg Val Leu Val Asn Gln Val Pro Gly Gly Met Ile Ser Asn Leu
                290                 295                 300

Ser Asn Gln Leu Lys Glu Gln Gly Ala Leu Asn Arg Met Asp Glu Val
305                 310                 315                 320

Leu Ala Glu Ile Pro Arg Val Arg Glu Asp Leu Gly Tyr Pro Pro Leu
                325                 330                 335

Val Thr Pro Thr Ser Gln Ile Val Gly Thr Gln Ala Val Leu Asn Val
                340                 345                 350

Leu Thr Gly Ser Arg Tyr Lys Ser Ile Thr Asn Glu Val Lys Asn Tyr
                355                 360                 365

Leu Leu Gly Gln Tyr Gly Lys Ala Pro Ala Ala Val Asn Ala Asp Val
                370                 375                 380

Arg Lys Gln Ala Val Gly Asp Ala Glu Val Ile Thr Cys Arg Pro Ala
385                 390                 395                 400

Asp Leu Leu Gln Pro Glu Met Ala Arg Leu Gln Ser Glu Ala Glu Arg
                405                 410                 415

Phe Ala Asn Asn Glu Gln Asp Val Leu Thr Tyr Ala Met Phe Pro Asp
                420                 425                 430

Ile Gly Gln Thr Phe Leu Gln Glu Arg Asn Ala Gly Ser Leu Gln Pro
                435                 440                 445

Glu Gln Leu Leu Ser Lys Glu Ala Val Thr Gln Gln Thr Ala Ala Ala
                450                 455                 460

Arg Tyr Ala Pro Asn Glu Phe Asn Ile Thr Leu His Gly Glu Thr Tyr
465                 470                 475                 480
```

```
His Ile Lys Leu Thr Gly Ser Gly His Ala Gly Glu Arg Lys Pro
            485                 490                 495

Tyr Tyr Val Lys Val Asp Gly Ile Ser Glu Glu Val Phe Val Glu Thr
            500                 505                 510

Leu Ser Glu Met Glu Val Ser Gly Gly Asn Ser Asn Gly Ser Lys Lys
            515                 520                 525

Lys Ala Ala Val Ala Ala Ser Gly Arg Pro Arg Pro Asn His Pro
            530                 535                 540

Gly Cys Val Thr Thr Ala Met Pro Gly Thr Ile Val Thr Val Lys Val
545                 550                 555                 560

Asn Val Gly Asp Lys Val Asn Ala Gly Asp Gly Val Leu Val Ile Glu
                565                 570                 575

Ala Met Lys Met Glu Asn Glu Ile Gln Ala Ser Lys Ser Gly Thr Val
                580                 585                 590

Val Ala Ile His Val Ala Lys Gly Asp Ser Val Thr Pro Asp Glu Thr
            595                 600                 605

Leu Ile Glu Ile Gln Pro Glu
    610                 615

<210> SEQ ID NO 33
<211> LENGTH: 2781
<212> TYPE: DNA
<213> ORGANISM: Methylophilus methylotrophus
<220> FEATURE:
<221> NAME/KEY: CDS
<222> LOCATION: (1)..(2781)
<223> OTHER INFORMATION:

<400> SEQUENCE: 33 atg ata aaa aaa ctg gct gcc agc gcg atg gtt tca gca gag gcg caa      48
Met Ile Lys Lys Leu Ala Ala Ser Ala Met Val Ser Ala Glu Ala Gln
1               5                   10                  15 ctg gcc gaa aat ata cag tta ttg ggt gca ctg ctg gat aaa gca gtc      96
Leu Ala Glu Asn Ile Gln Leu Leu Gly Ala Leu Leu Asp Lys Ala Val
            20                  25                  30 ttg gat gtg gaa ggc gaa gag gtc gca caa aaa att gcc gct atc cgc     144
Leu Asp Val Glu Gly Glu Glu Val Ala Gln Lys Ile Ala Ala Ile Arg
        35                  40                  45 cag gcg gcg ttg cgt ttt cac cag acg cat gat cag cag gct tct ttg     192
Gln Ala Ala Leu Arg Phe His Gln Thr His Asp Gln Gln Ala Ser Leu
    50                  55                  60 gat ctc gaa caa tta ctg gcc aat ctg agt ctg gag cat acg gtg cgt     240
Asp Leu Glu Gln Leu Leu Ala Asn Leu Ser Leu Glu His Thr Val Arg
65                  70                  75                  80 gtc gtg cgg gca ctg gct tat ttc aag cat ctg gcc aac ttg gcc gaa     288
Val Val Arg Ala Leu Ala Tyr Phe Lys His Leu Ala Asn Leu Ala Glu
                85                  90                  95 gat tta tat ggt cag caa ttg ggg cat tgc cag cag aat acc ccg gcg     336
Asp Leu Tyr Gly Gln Gln Leu Gly His Cys Gln Gln Asn Thr Pro Ala
            100                 105                 110 ccc ggc atg ctg tcg tat acc ctg gcg aaa atc aag acg gct ttt atc     384
Pro Gly Met Leu Ser Tyr Thr Leu Ala Lys Ile Lys Thr Ala Phe Ile
        115                 120                 125 cca gcc gaa acg att aaa gcg ttg tta gaa agt gca ctg atc tcg ccc     432
Pro Ala Glu Thr Ile Lys Ala Leu Leu Glu Ser Ala Leu Ile Ser Pro
    130                 135                 140 gtg ctg aca gca cat cct acc gag gtg caa cgc aaa agt gtg ctg gat     480
Val Leu Thr Ala His Pro Thr Glu Val Gln Arg Lys Ser Val Leu Asp
145                 150                 155                 160
```

-continued

```
att gag cgc cag att gcc gaa ctg ctg gcc gaa agg tca cat ctg gtg      528
Ile Glu Arg Gln Ile Ala Glu Leu Leu Ala Glu Arg Ser His Leu Val
            165                 170                 175 tcc gag cgt caa ttg gcg cgc aac acc ttg tta ctg caa ggg gca gtc      576
Ser Glu Arg Gln Leu Ala Arg Asn Thr Leu Leu Leu Gln Gly Ala Val
        180                 185                 190 tcg gca cta tgg caa aca cgc atg atg cgt tat tcc aag ctc agt gtg      624
Ser Ala Leu Trp Gln Thr Arg Met Met Arg Tyr Ser Lys Leu Ser Val
    195                 200                 205 caa aac gag att gaa aat tcg ctg act tat tat gaa tcg act ttc ctc      672
Gln Asn Glu Ile Glu Asn Ser Leu Thr Tyr Tyr Glu Ser Thr Phe Leu
210                 215                 220 aat gtc atc cca gag ata ttg cag gac atc gag cgc gac ctg tct gac      720
Asn Val Ile Pro Glu Ile Leu Gln Asp Ile Glu Arg Asp Leu Ser Asp
225                 230                 235                 240 ctg ttg ccg gat gtg acg cta ccg ggc ttt ttg cgc atg ggt agc tgg      768
Leu Leu Pro Asp Val Thr Leu Pro Gly Phe Leu Arg Met Gly Ser Trp
                245                 250                 255 ata ggt ggc gac cgc gat ggt aac ccg ttt gtg aac ggc acg aca ttg      816
Ile Gly Gly Asp Arg Asp Gly Asn Pro Phe Val Asn Gly Thr Thr Leu
            260                 265                 270 cgg gac agc gtg cgt ttg cag gcc act act ttg ttc agg ttt tat ttg      864
Arg Asp Ser Val Arg Leu Gln Ala Thr Thr Leu Phe Arg Phe Tyr Leu
        275                 280                 285 cag gaa ctg gca gcc ctt aaa cgc gaa ctg gcg gtg tct acc cgt gtg      912
Gln Glu Leu Ala Ala Leu Lys Arg Glu Leu Ala Val Ser Thr Arg Val
    290                 295                 300 gtc ggc gtc agc gag gct gta ttg cag atg gcc agg acc tcg cgt gac      960
Val Gly Val Ser Glu Ala Val Leu Gln Met Ala Arg Thr Ser Arg Asp
305                 310                 315                 320 caa tcg caa cat cgg cta gac gaa cct tat cgc ctg gcg ctc aat ggc     1008
Gln Ser Gln His Arg Leu Asp Glu Pro Tyr Arg Leu Ala Leu Asn Gly
                325                 330                 335 atc tat gac cgt gtg ctg gtc acg gca gat cag ttg ttg ccg gga gag     1056
Ile Tyr Asp Arg Val Leu Val Thr Ala Asp Gln Leu Leu Pro Gly Glu
            340                 345                 350 ggc tgg gtg gtg gat gaa agt atc gct gcc gac cct tat gaa agc gca     1104
Gly Trp Val Val Asp Glu Ser Ile Ala Ala Asp Pro Tyr Glu Ser Ala
        355                 360                 365 cat gac ctg ctg gag cca ttg gaa att atc gct gcg tct tta cgc gaa     1152
His Asp Leu Leu Glu Pro Leu Glu Ile Ile Ala Ala Ser Leu Arg Glu
    370                 375                 380 cat cag ggc gaa tcc ctg att tac ccg cgg ctg ggc aag ctg atc aag     1200
His Gln Gly Glu Ser Leu Ile Tyr Pro Arg Leu Gly Lys Leu Ile Lys
385                 390                 395                 400 gcc atc cat agc ttt ggt ttc cat ctg gca aca gtg gat atc cgc caa     1248
Ala Ile His Ser Phe Gly Phe His Leu Ala Thr Val Asp Ile Arg Gln
                405                 410                 415 tca tcg gat gtg cat gaa gcg gtc atc act gag tta ttg cat aaa gct     1296
Ser Ser Asp Val His Glu Ala Val Ile Thr Glu Leu Leu His Lys Ala
            420                 425                 430 ggc cat gat ttt gat tat gcc ggg ttt aat gag gac gaa aaa atc ggc     1344
Gly His Asp Phe Asp Tyr Ala Gly Phe Asn Glu Asp Glu Lys Ile Gly
        435                 440                 445 gtc ttg ctc gag gaa ctc aaa cag ccg cgc ctg ctg ttt tcg cca ttc     1392
Val Leu Leu Glu Glu Leu Lys Gln Pro Arg Leu Leu Phe Ser Pro Phe
    450                 455                 460 cag caa tac tct gag ctg gtg cat aag gaa atc ggc gtg ctg gtt gca     1440
Gln Gln Tyr Ser Glu Leu Val His Lys Glu Ile Gly Val Leu Val Ala
```

```
                  465                 470                 475                 480
gta cgt gaa atg cgt gag cgc ttt ggt gag cat gcc gtg cgg caa tat        1488
Val Arg Glu Met Arg Glu Arg Phe Gly Glu His Ala Val Arg Gln Tyr
                        485                 490                 495 att att tcg cat acc gaa acg ctg tct gac ctg ctt gaa gtc gcc ttg        1536
Ile Ile Ser His Thr Glu Thr Leu Ser Asp Leu Leu Glu Val Ala Leu
                500                 505                 510 tta caa cgc gag gcc ggg ctg ctg cgc ggc gtg tgg ggt tca gcc aat        1584
Leu Gln Arg Glu Ala Gly Leu Leu Arg Gly Val Trp Gly Ser Ala Asn
        515                 520                 525 gta cag gta gat ttg cat atc gtg ccg ttg ttt gaa acc att gct gac        1632
Val Gln Val Asp Leu His Ile Val Pro Leu Phe Glu Thr Ile Ala Asp
530                 535                 540 tta cgt tac gcg ccc atg att atg ggt aaa tgg ctg agc ctg ctg ggc        1680
Leu Arg Tyr Ala Pro Met Ile Met Gly Lys Trp Leu Ser Leu Leu Gly
545                 550                 555                 560 atc cgt cat atc atc cgt tac cag ggc agt gag cag gaa atc atg ctg        1728
Ile Arg His Ile Ile Arg Tyr Gln Gly Ser Glu Gln Glu Ile Met Leu
                565                 570                 575 ggc tat tcc gac agc aac aag gat gga gga ttc ctg acc tcg aac tgg        1776
Gly Tyr Ser Asp Ser Asn Lys Asp Gly Gly Phe Leu Thr Ser Asn Trp
                580                 585                 590 gag ttg tat aag gca gaa att tcg ctt gtc gaa tta ttc aat cag gcc        1824
Glu Leu Tyr Lys Ala Glu Ile Ser Leu Val Glu Leu Phe Asn Gln Ala
        595                 600                 605 aac gtg aag ttg cgc ctg ttt cat ggc cgc ggc ggc acg gtg ggt cgg        1872
Asn Val Lys Leu Arg Leu Phe His Gly Arg Gly Gly Thr Val Gly Arg
610                 615                 620 gga ggg ggg cct act tac cag gct gtg atg gcg caa ccc aag gga aca        1920
Gly Gly Gly Pro Thr Tyr Gln Ala Val Met Ala Gln Pro Lys Gly Thr
625                 630                 635                 640 gtc gat ggg cag ata cgc ctg acc gaa caa ggt gag atc att tct aca        1968
Val Asp Gly Gln Ile Arg Leu Thr Glu Gln Gly Glu Ile Ile Ser Thr
                645                 650                 655 agg tat gct gac ccc gtg gtg ggc cgc cag cat ctg gaa aca ctg att        2016
Arg Tyr Ala Asp Pro Val Val Gly Arg Gln His Leu Glu Thr Leu Ile
                660                 665                 670 gca gcg acg ctg gac gcc acc ctg ttt ccg tct gac cag ttg gaa tcc        2064
Ala Ala Thr Leu Asp Ala Thr Leu Phe Pro Ser Asp Gln Leu Glu Ser
        675                 680                 685 tcc aaa cgg cga gcc ttc gaa agt gtg atg gaa aca tta tca acc acg        2112
Ser Lys Arg Arg Ala Phe Glu Ser Val Met Glu Thr Leu Ser Thr Thr
690                 695                 700 gca atg acc agc tac cgc agc ctg gta tat gaa acg cca ggg ttt gcc        2160
Ala Met Thr Ser Tyr Arg Ser Leu Val Tyr Glu Thr Pro Gly Phe Ala
705                 710                 715                 720 gaa tac ttt ttt aat act acc ccg ata gac gaa att gct ggc ttg aac        2208
Glu Tyr Phe Phe Asn Thr Thr Pro Ile Asp Glu Ile Ala Gly Leu Asn
                725                 730                 735 ctg ggc agc cgc ccg gct gcg cgt aaa tcc acg cgg cgc att gag gac        2256
Leu Gly Ser Arg Pro Ala Ala Arg Lys Ser Thr Arg Arg Ile Glu Asp
                740                 745                 750 ttg cga gcg att ccc tgg gga ttt tcc tgg gga caa tgc cgc ttg tta        2304
Leu Arg Ala Ile Pro Trp Gly Phe Ser Trp Gly Gln Cys Arg Leu Leu
        755                 760                 765 ttg ccg ggc tgg tat ggg ctg ggt agt gca ata cag cat ttt ttg cag        2352
Leu Pro Gly Trp Tyr Gly Leu Gly Ser Ala Ile Gln His Phe Leu Gln
770                 775                 780 cag gat cct gct ttg aaa gac gtg cgc ctg gcg atg ctg cat gac atg        2400
```

```
Gln Asp Pro Ala Leu Lys Asp Val Arg Leu Ala Met Leu His Asp Met
785                 790                 795                 800 cag gca cac tgg ccg ctg ttc aat acg ctg atc aat aat gtg gac atg        2448
Gln Ala His Trp Pro Leu Phe Asn Thr Leu Ile Asn Asn Val Asp Met
                805                 810                 815 gtg ctg gcc aag act gac ctg atc gtg gcg cga cac tat gca cat ttg        2496
Val Leu Ala Lys Thr Asp Leu Ile Val Ala Arg His Tyr Ala His Leu
            820                 825                 830 ctg gaa gac cgc gag ctg cgt gaa gag att ttc agc cgc ata gaa cat        2544
Leu Glu Asp Arg Glu Leu Arg Glu Glu Ile Phe Ser Arg Ile Glu His
        835                 840                 845 gag cac aaa ttg acc acg gat gcc att aac ctg tta ttg ggc acc acg        2592
Glu His Lys Leu Thr Thr Asp Ala Ile Asn Leu Leu Leu Gly Thr Thr
850                 855                 860 cag cgt ttg gcc acc caa ccc gtg att gca aaa tcc atc cgc gac cgg        2640
Gln Arg Leu Ala Thr Gln Pro Val Ile Ala Lys Ser Ile Arg Asp Arg
865                 870                 875                 880 ctg cct tac ctc gat cct tta aat cat ttg caa gta gaa atg att caa        2688
Leu Pro Tyr Leu Asp Pro Leu Asn His Leu Gln Val Glu Met Ile Gln
                885                 890                 895 cga tat cgc aag ggc gaa acg gat gaa aaa ctg aaa tgg gct atc ccg        2736
Arg Tyr Arg Lys Gly Glu Thr Asp Glu Lys Leu Lys Trp Ala Ile Pro
            900                 905                 910 tta acc att aat ggc att gcg acc agt ttg cgt aac acc ggt taa            2781
Leu Thr Ile Asn Gly Ile Ala Thr Ser Leu Arg Asn Thr Gly
        915                 920                 925
```

<210> SEQ ID NO 34
<211> LENGTH: 926
<212> TYPE: PRT
<213> ORGANISM: Methylophilus methylotrophus

<400> SEQUENCE: 34

```
Met Ile Lys Lys Leu Ala Ala Ser Ala Met Val Ser Ala Glu Ala Gln
1               5                   10                  15

Leu Ala Glu Asn Ile Gln Leu Leu Gly Ala Leu Leu Asp Lys Ala Val
            20                  25                  30

Leu Asp Val Glu Gly Glu Val Ala Gln Lys Ile Ala Ala Ile Arg
        35                  40                  45

Gln Ala Ala Leu Arg Phe His Gln Thr His Asp Gln Gln Ala Ser Leu
    50                  55                  60

Asp Leu Glu Gln Leu Leu Ala Asn Leu Ser Leu Glu His Thr Val Arg
65                  70                  75                  80

Val Val Arg Ala Leu Ala Tyr Phe Lys His Leu Ala Asn Leu Ala Glu
                85                  90                  95

Asp Leu Tyr Gly Gln Gln Leu Gly His Cys Gln Gln Asn Thr Pro Ala
            100                 105                 110

Pro Gly Met Leu Ser Tyr Thr Leu Ala Lys Ile Lys Thr Ala Phe Ile
        115                 120                 125

Pro Ala Glu Thr Ile Lys Ala Leu Leu Glu Ser Ala Leu Ile Ser Pro
    130                 135                 140

Val Leu Thr Ala His Pro Thr Glu Val Gln Arg Lys Ser Val Leu Asp
145                 150                 155                 160

Ile Glu Arg Gln Ile Ala Glu Leu Leu Ala Glu Arg Ser His Leu Val
                165                 170                 175

Ser Glu Arg Gln Leu Ala Arg Asn Thr Leu Leu Leu Gln Gly Ala Val
            180                 185                 190
```

-continued

```
Ser Ala Leu Trp Gln Thr Arg Met Met Arg Tyr Ser Lys Leu Ser Val
            195                 200                 205
Gln Asn Glu Ile Glu Asn Ser Leu Thr Tyr Tyr Glu Ser Thr Phe Leu
        210                 215                 220
Asn Val Ile Pro Glu Ile Leu Gln Asp Ile Glu Arg Asp Leu Ser Asp
225                 230                 235                 240
Leu Leu Pro Asp Val Thr Leu Pro Gly Phe Leu Arg Met Gly Ser Trp
                245                 250                 255
Ile Gly Gly Asp Arg Asp Gly Asn Pro Phe Val Asn Gly Thr Thr Leu
            260                 265                 270
Arg Asp Ser Val Arg Leu Gln Ala Thr Thr Leu Phe Arg Phe Tyr Leu
        275                 280                 285
Gln Glu Leu Ala Ala Leu Lys Arg Glu Leu Ala Val Ser Thr Arg Val
        290                 295                 300
Val Gly Val Ser Glu Ala Val Leu Gln Met Ala Arg Thr Ser Arg Asp
305                 310                 315                 320
Gln Ser Gln His Arg Leu Asp Glu Pro Tyr Arg Leu Ala Leu Asn Gly
                325                 330                 335
Ile Tyr Asp Arg Val Leu Val Thr Ala Asp Gln Leu Leu Pro Gly Glu
            340                 345                 350
Gly Trp Val Val Asp Glu Ser Ile Ala Ala Asp Pro Tyr Glu Ser Ala
        355                 360                 365
His Asp Leu Leu Glu Pro Leu Glu Ile Ile Ala Ala Ser Leu Arg Glu
        370                 375                 380
His Gln Gly Glu Ser Leu Ile Tyr Pro Arg Leu Gly Lys Leu Ile Lys
385                 390                 395                 400
Ala Ile His Ser Phe Gly Phe His Leu Ala Thr Val Asp Ile Arg Gln
                405                 410                 415
Ser Ser Asp Val His Glu Ala Val Ile Thr Glu Leu Leu His Lys Ala
            420                 425                 430
Gly His Asp Phe Asp Tyr Ala Gly Phe Asn Glu Asp Glu Lys Ile Gly
        435                 440                 445
Val Leu Leu Glu Glu Leu Lys Gln Pro Arg Leu Leu Phe Ser Pro Phe
        450                 455                 460
Gln Gln Tyr Ser Glu Leu Val His Lys Glu Ile Gly Val Leu Val Ala
465                 470                 475                 480
Val Arg Glu Met Arg Glu Arg Phe Gly Glu His Ala Val Arg Gln Tyr
                485                 490                 495
Ile Ile Ser His Thr Glu Thr Leu Ser Asp Leu Leu Glu Val Ala Leu
            500                 505                 510
Leu Gln Arg Glu Ala Gly Leu Leu Arg Gly Val Trp Gly Ser Ala Asn
        515                 520                 525
Val Gln Val Asp Leu His Ile Val Pro Leu Phe Glu Thr Ile Ala Asp
        530                 535                 540
Leu Arg Tyr Ala Pro Met Ile Met Gly Lys Trp Leu Ser Leu Leu Gly
545                 550                 555                 560
Ile Arg His Ile Ile Arg Tyr Gln Gly Ser Glu Gln Glu Ile Met Leu
                565                 570                 575
Gly Tyr Ser Asp Ser Asn Lys Asp Gly Gly Phe Leu Thr Ser Asn Trp
            580                 585                 590
Glu Leu Tyr Lys Ala Glu Ile Ser Leu Val Glu Leu Phe Asn Gln Ala
        595                 600                 605
Asn Val Lys Leu Arg Leu Phe His Gly Arg Gly Gly Thr Val Gly Arg
```

-continued

```
                610                 615                 620
Gly Gly Gly Pro Thr Tyr Gln Ala Val Met Ala Gln Pro Lys Gly Thr
625                 630                 635                 640

Val Asp Gly Gln Ile Arg Leu Thr Glu Gln Gly Glu Ile Ile Ser Thr
                645                 650                 655

Arg Tyr Ala Asp Pro Val Val Gly Arg Gln His Leu Glu Thr Leu Ile
            660                 665                 670

Ala Ala Thr Leu Asp Ala Thr Leu Phe Pro Ser Asp Gln Leu Glu Ser
            675                 680                 685

Ser Lys Arg Arg Ala Phe Glu Ser Val Met Glu Thr Leu Ser Thr Thr
690                 695                 700

Ala Met Thr Ser Tyr Arg Ser Leu Val Tyr Glu Thr Pro Gly Phe Ala
705                 710                 715                 720

Glu Tyr Phe Phe Asn Thr Thr Pro Ile Asp Glu Ile Ala Gly Leu Asn
                725                 730                 735

Leu Gly Ser Arg Pro Ala Ala Arg Lys Ser Thr Arg Ile Glu Asp
            740                 745                 750

Leu Arg Ala Ile Pro Trp Gly Phe Ser Trp Gly Gln Cys Arg Leu Leu
            755                 760                 765

Leu Pro Gly Trp Tyr Gly Leu Gly Ser Ala Ile Gln His Phe Leu Gln
770                 775                 780

Gln Asp Pro Ala Leu Lys Asp Val Arg Leu Ala Met Leu His Asp Met
785                 790                 795                 800

Gln Ala His Trp Pro Leu Phe Asn Thr Leu Ile Asn Asn Val Asp Met
                805                 810                 815

Val Leu Ala Lys Thr Asp Leu Ile Val Ala Arg His Tyr Ala His Leu
            820                 825                 830

Leu Glu Asp Arg Glu Leu Arg Glu Glu Ile Phe Ser Arg Ile Glu His
            835                 840                 845

Glu His Lys Leu Thr Thr Asp Ala Ile Asn Leu Leu Gly Thr Thr
                850                 855                 860

Gln Arg Leu Ala Thr Gln Pro Val Ile Ala Lys Ser Ile Arg Asp Arg
865                 870                 875                 880

Leu Pro Tyr Leu Asp Pro Leu Asn His Leu Gln Val Glu Met Ile Gln
                885                 890                 895

Arg Tyr Arg Lys Gly Glu Thr Asp Glu Lys Leu Lys Trp Ala Ile Pro
            900                 905                 910

Leu Thr Ile Asn Gly Ile Ala Thr Ser Leu Arg Asn Thr Gly
            915                 920                 925
```

<210> SEQ ID NO 35
<211> LENGTH: 1227
<212> TYPE: DNA
<213> ORGANISM: Methylophilus methylotrophus
<220> FEATURE:
<221> NAME/KEY: CDS
<222> LOCATION: (1)..(1227)
<223> OTHER INFORMATION:

<400> SEQUENCE: 35

```
atg cag cca gtc aat aaa tcc agc aaa ctc agt aat gtc tgt tac gac      48
Met Gln Pro Val Asn Lys Ser Ser Lys Leu Ser Asn Val Cys Tyr Asp
1               5                   10                  15 atc cgc ggc cct gtc cta caa cgt gcg cgc cag atg gaa gag gat ggg      96
Ile Arg Gly Pro Val Leu Gln Arg Ala Arg Gln Met Glu Glu Asp Gly
                20                  25                  30
```

-continued

| | | |
|---|---|---|
| caa cgc att atc aag ttg aat atc ggc aac ccc atg ccg ttc ggt ttt<br>Gln Arg Ile Ile Lys Leu Asn Ile Gly Asn Pro Met Pro Phe Gly Phe<br>35　　　　　　　　40　　　　　　　　45 | 144 | |
| aat gcc ccc gaa gaa att gtc cag gac gtg atc cat aat atg gac cag<br>Asn Ala Pro Glu Glu Ile Val Gln Asp Val Ile His Asn Met Asp Gln<br>50　　　　　　　　55　　　　　　　　60 | 192 | |
| gcc tcg ggt tat acc gat tcc aaa gga ttg ttc gcg gcg cgc aaa gcg<br>Ala Ser Gly Tyr Thr Asp Ser Lys Gly Leu Phe Ala Ala Arg Lys Ala<br>65　　　　　　　　70　　　　　　　　75　　　　　　　　80 | 240 | |
| att atg cat tac acc cag caa aaa aac att gcc ggg gtg acc ata gac<br>Ile Met His Tyr Thr Gln Gln Lys Asn Ile Ala Gly Val Thr Ile Asp<br>　　　　　85　　　　　　　　90　　　　　　　　95 | 288 | |
| gac atc att atc ggt aat ggt gtg tct gaa ctc att gtg atg gcc atg<br>Asp Ile Ile Ile Gly Asn Gly Val Ser Glu Leu Ile Val Met Ala Met<br>　　　　100　　　　　　　　105　　　　　　　　110 | 336 | |
| cag ggc ttg ctc aat aat ggt gac cag att ctg gtg ccc atg ccg gat<br>Gln Gly Leu Leu Asn Asn Gly Asp Gln Ile Leu Val Pro Met Pro Asp<br>115　　　　　　　　120　　　　　　　　125 | 384 | |
| tat ccg ttg tgg acc gct gca gtg aac ctg gca ggt ggt acg gcg cgt<br>Tyr Pro Leu Trp Thr Ala Ala Val Asn Leu Ala Gly Gly Thr Ala Arg<br>130　　　　　　　　135　　　　　　　　140 | 432 | |
| cat tac gtc tgt gac gag cag tcc ggc tgg ctg cca gac ctc aag gat<br>His Tyr Val Cys Asp Glu Gln Ser Gly Trp Leu Pro Asp Leu Lys Asp<br>145　　　　　　　　150　　　　　　　　155　　　　　　　　160 | 480 | |
| att gag aac aag atc acg gcc aat acc aaa ggt atc gtg att atc aat<br>Ile Glu Asn Lys Ile Thr Ala Asn Thr Lys Gly Ile Val Ile Ile Asn<br>　　　　　165　　　　　　　　170　　　　　　　　175 | 528 | |
| cct aac aat ccg acc ggt gcc ttg tat ccc aaa gaa acg ctg gaa ggc<br>Pro Asn Asn Pro Thr Gly Ala Leu Tyr Pro Lys Glu Thr Leu Glu Gly<br>　　　　180　　　　　　　　185　　　　　　　　190 | 576 | |
| att atc gag att gcg cgt cat cat agc ctg gtg att ttt gcc gac gag<br>Ile Ile Glu Ile Ala Arg His His Ser Leu Val Ile Phe Ala Asp Glu<br>195　　　　　　　　200　　　　　　　　205 | 624 | |
| att tac gac aag gtg ttg tat gac ggt aac acg cat acg tcc atc gcg<br>Ile Tyr Asp Lys Val Leu Tyr Asp Gly Asn Thr His Thr Ser Ile Ala<br>210　　　　　　　　215　　　　　　　　220 | 672 | |
| tcg ctg gct gac gat gtg ctg ttt gtg acc ttt aac ggc ttg tcc aaa<br>Ser Leu Ala Asp Asp Val Leu Phe Val Thr Phe Asn Gly Leu Ser Lys<br>225　　　　　　　　230　　　　　　　　235　　　　　　　　240 | 720 | |
| aat tac cgc gcc tgt ggc tac cgc tca ggc tgg atg att atc tcc ggc<br>Asn Tyr Arg Ala Cys Gly Tyr Arg Ser Gly Trp Met Ile Ile Ser Gly<br>　　　　　245　　　　　　　　250　　　　　　　　255 | 768 | |
| gat aaa aag gat gcc aag gat tat atc gaa ggc ctc aat atg ctg gcc<br>Asp Lys Lys Asp Ala Lys Asp Tyr Ile Glu Gly Leu Asn Met Leu Ala<br>　　　　260　　　　　　　　265　　　　　　　　270 | 816 | |
| tcc atg cgt ttg tgt gcc aat gtg ccc ggg caa ctg gcg att cag aca<br>Ser Met Arg Leu Cys Ala Asn Val Pro Gly Gln Leu Ala Ile Gln Thr<br>275　　　　　　　　280　　　　　　　　285 | 864 | |
| gca cta ggc ggt tac cag agt att aat gac ctg gtc gcg ccc agt ggc<br>Ala Leu Gly Gly Tyr Gln Ser Ile Asn Asp Leu Val Ala Pro Ser Gly<br>290　　　　　　　　295　　　　　　　　300 | 912 | |
| cgc ttg tgc aag cag cgt gac ctg gct tac gac atg ctc act tcc atg<br>Arg Leu Cys Lys Gln Arg Asp Leu Ala Tyr Asp Met Leu Thr Ser Met<br>305　　　　　　　　310　　　　　　　　315　　　　　　　　320 | 960 | |
| ccg ggc gtg act tgt gtc aag cca gct gca gcc atg tat ctg ttt cca<br>Pro Gly Val Thr Cys Val Lys Pro Ala Ala Ala Met Tyr Leu Phe Pro<br>　　　　　325　　　　　　　　330　　　　　　　　335 | 1008 | |
| aag ttg gat cca gcg atg tat ccg atc gaa gat gat cag cag ttt atc<br>Lys Leu Asp Pro Ala Met Tyr Pro Ile Glu Asp Asp Gln Gln Phe Ile<br>　　　　340　　　　　　　　345　　　　　　　　350 | 1056 | |

```
ctc gac tta ttg ctg gaa gaa aaa gta ctg ctg gtt caa ggc acg ggc    1104
Leu Asp Leu Leu Leu Glu Glu Lys Val Leu Leu Val Gln Gly Thr Gly
        355                 360                 365 ttt aac tgg aaa gcg cct gat cat ttc agg gta gtg ttc ctg cct aat    1152
Phe Asn Trp Lys Ala Pro Asp His Phe Arg Val Val Phe Leu Pro Asn
    370                 375                 380 gtg gat gac ctg acc gag gcg atg aca cgc ata ggc cgc tac ctg gat    1200
Val Asp Asp Leu Thr Glu Ala Met Thr Arg Ile Gly Arg Tyr Leu Asp
385                 390                 395                 400 agc tat cgt aag aag cat gca aaa taa                                1227
Ser Tyr Arg Lys Lys His Ala Lys
                405

<210> SEQ ID NO 36
<211> LENGTH: 408
<212> TYPE: PRT
<213> ORGANISM: Methylophilus methylotrophus

<400> SEQUENCE: 36

Met Gln Pro Val Asn Lys Ser Ser Lys Leu Ser Asn Val Cys Tyr Asp
1               5                   10                  15

Ile Arg Gly Pro Val Leu Gln Arg Ala Arg Gln Met Glu Glu Asp Gly
            20                  25                  30

Gln Arg Ile Ile Lys Leu Asn Ile Gly Asn Pro Met Pro Phe Gly Phe
        35                  40                  45

Asn Ala Pro Glu Glu Ile Val Gln Asp Val Ile His Asn Met Asp Gln
    50                  55                  60

Ala Ser Gly Tyr Thr Asp Ser Lys Gly Leu Phe Ala Ala Arg Lys Ala
65                  70                  75                  80

Ile Met His Tyr Thr Gln Gln Lys Asn Ile Ala Gly Val Thr Ile Asp
                85                  90                  95

Asp Ile Ile Gly Asn Gly Val Ser Glu Leu Ile Val Met Ala Met
            100                 105                 110

Gln Gly Leu Leu Asn Asn Gly Asp Gln Ile Leu Val Pro Met Pro Asp
        115                 120                 125

Tyr Pro Leu Trp Thr Ala Ala Val Asn Leu Ala Gly Gly Thr Ala Arg
    130                 135                 140

His Tyr Val Cys Asp Glu Gln Ser Gly Trp Leu Pro Asp Leu Lys Asp
145                 150                 155                 160

Ile Glu Asn Lys Ile Thr Ala Asn Thr Lys Gly Ile Val Ile Ile Asn
                165                 170                 175

Pro Asn Asn Pro Thr Gly Ala Leu Tyr Pro Lys Glu Thr Leu Glu Gly
            180                 185                 190

Ile Ile Glu Ile Ala Arg His His Ser Leu Val Ile Phe Ala Asp Glu
        195                 200                 205

Ile Tyr Asp Lys Val Leu Tyr Asp Gly Asn Thr His Thr Ser Ile Ala
    210                 215                 220

Ser Leu Ala Asp Asp Val Leu Phe Val Thr Phe Asn Gly Leu Ser Lys
225                 230                 235                 240

Asn Tyr Arg Ala Cys Gly Tyr Arg Ser Gly Trp Met Ile Ile Ser Gly
                245                 250                 255

Asp Lys Lys Asp Ala Lys Asp Tyr Ile Glu Gly Leu Asn Met Leu Ala
            260                 265                 270

Ser Met Arg Leu Cys Ala Asn Val Pro Gly Gln Leu Ala Ile Gln Thr
        275                 280                 285
```

```
Ala Leu Gly Gly Tyr Gln Ser Ile Asn Asp Leu Val Ala Pro Ser Gly
    290                 295                 300

Arg Leu Cys Lys Gln Arg Asp Leu Ala Tyr Asp Met Leu Thr Ser Met
305                 310                 315                 320

Pro Gly Val Thr Cys Val Lys Pro Ala Ala Met Tyr Leu Phe Pro
                325                 330                 335

Lys Leu Asp Pro Ala Met Tyr Pro Ile Glu Asp Gln Gln Phe Ile
                340                 345                 350

Leu Asp Leu Leu Leu Glu Glu Lys Val Leu Leu Val Gln Gly Thr Gly
            355                 360                 365

Phe Asn Trp Lys Ala Pro Asp His Phe Arg Val Val Phe Leu Pro Asn
370                 375                 380

Val Asp Asp Leu Thr Glu Ala Met Thr Arg Ile Gly Arg Tyr Leu Asp
385                 390                 395                 400

Ser Tyr Arg Lys Lys His Ala Lys
                405

<210> SEQ ID NO 37
<211> LENGTH: 1191
<212> TYPE: DNA
<213> ORGANISM: Methylophilus methylotrophus
<220> FEATURE:
<221> NAME/KEY: CDS
<222> LOCATION: (1)..(1191)
<223> OTHER INFORMATION:

<400> SEQUENCE: 37 gtg ctg tct gcg cgc gtg tta tcg att aaa gaa tcc ccc act ctg gcc        48
Val Leu Ser Ala Arg Val Leu Ser Ile Lys Glu Ser Pro Thr Leu Ala
1               5                   10                  15 att act gcc aaa gcg gct aaa tac aag tca gaa ggc cgc ccg att att        96
Ile Thr Ala Lys Ala Ala Lys Tyr Lys Ser Glu Gly Arg Pro Ile Ile
            20                  25                  30 ggc ttg gcc gcc ggc gag cct gac ttt gat acg ccc cag cat att aaa       144
Gly Leu Ala Ala Gly Glu Pro Asp Phe Asp Thr Pro Gln His Ile Lys
        35                  40                  45 gat gcc gcc aaa gca gcg att gat gca ggc tat acc aaa tac aca ccg       192
Asp Ala Ala Lys Ala Ala Ile Asp Ala Gly Tyr Thr Lys Tyr Thr Pro
    50                  55                  60 gtc agc ggc atc cct gcc ctg aaa aaa gcc atc gtc aac aaa ttc aag       240
Val Ser Gly Ile Pro Ala Leu Lys Lys Ala Ile Val Asn Lys Phe Lys
65                  70                  75                  80 aac gaa aac ggt ttt gac tat gcc gtg aac gaa gtg att gtc ggc gtc       288
Asn Glu Asn Gly Phe Asp Tyr Ala Val Asn Glu Val Ile Val Gly Val
                85                  90                  95 ggc ggc aag cag acc att ttc aac ctt tgt ctg gcc gtg ttg aat cct       336
Gly Gly Lys Gln Thr Ile Phe Asn Leu Cys Leu Ala Val Leu Asn Pro
            100                 105                 110 ggc gac gaa gtg att gtg ccc gcc cct tac tgg gtc agc tat gcc gat       384
Gly Asp Glu Val Ile Val Pro Ala Pro Tyr Trp Val Ser Tyr Ala Asp
        115                 120                 125 atc gcc atg gtg gcc gag gcc aaa cca gtg att atc gag tgc ggt att       432
Ile Ala Met Val Ala Glu Ala Lys Pro Val Ile Ile Glu Cys Gly Ile
    130                 135                 140 gag caa ggc ttc aaa ctg ttg cca gcc cag ctg gaa tcc gcc atc act       480
Glu Gln Gly Phe Lys Leu Leu Pro Ala Gln Leu Glu Ser Ala Ile Thr
145                 150                 155                 160 gcg aag acc aaa ctg gtg atg ttt aac tcc cct tcc aac ccc acc ggc       528
Ala Lys Thr Lys Leu Val Met Phe Asn Ser Pro Ser Asn Pro Thr Gly
                165                 170                 175
```

```
gcc gta tat acc ttg gac gaa tta aaa gcg cta ggt gag gta ttg cta    576
Ala Val Tyr Thr Leu Asp Glu Leu Lys Ala Leu Gly Glu Val Leu Leu
            180                 185                 190 aaa cac ccg cac gta ctg gtc gca aca gac gac atg tac gag cac gtc    624
Lys His Pro His Val Leu Val Ala Thr Asp Asp Met Tyr Glu His Val
                195                 200                 205 aac ctc act ggc gaa aaa ttc cat aac atc ctc aat gct gcc ccg ggc    672
Asn Leu Thr Gly Glu Lys Phe His Asn Ile Leu Asn Ala Ala Pro Gly
    210                 215                 220 ctt aaa gac cgc tgc ata gtt ttg aat ggc gtt tcc aaa gcc tac tca    720
Leu Lys Asp Arg Cys Ile Val Leu Asn Gly Val Ser Lys Ala Tyr Ser
225                 230                 235                 240 atg aca ggc tgg cgc att ggt tac gcg gca ggt cct gct tat atc atc    768
Met Thr Gly Trp Arg Ile Gly Tyr Ala Ala Gly Pro Ala Tyr Ile Ile
                245                 250                 255 aag gcc atg gaa atc ctg caa agc cag tca acc agt aat ccg gct tct    816
Lys Ala Met Glu Ile Leu Gln Ser Gln Ser Thr Ser Asn Pro Ala Ser
            260                 265                 270 att tca caa tat gca gca gaa gcc gcc ttg agc ggc tcg caa gac tgt    864
Ile Ser Gln Tyr Ala Ala Glu Ala Ala Leu Ser Gly Ser Gln Asp Cys
        275                 280                 285 atc aag cct atg gtg gcg gcc ttc cgc gag cgc cac aaa tat gtg gtt    912
Ile Lys Pro Met Val Ala Ala Phe Arg Glu Arg His Lys Tyr Val Val
    290                 295                 300 gac cgc ttt aat gcc att cct ggc tta agt tgc cta atg gca ggt ggc    960
Asp Arg Phe Asn Ala Ile Pro Gly Leu Ser Cys Leu Met Ala Gly Gly
305                 310                 315                 320 gca ttt tat gca ttt ccg gat gca cgc caa gcc att acc aat ctg cat   1008
Ala Phe Tyr Ala Phe Pro Asp Ala Arg Gln Ala Ile Thr Asn Leu His
                325                 330                 335 caa gcg ggc aaa atc aag gag atg aca gat atg gcc ctg gca gaa tac   1056
Gln Ala Gly Lys Ile Lys Glu Met Thr Asp Met Ala Leu Ala Glu Tyr
            340                 345                 350 ctg ctt gaa gaa cac aat gtc gcc gtg gtg cct ggc tct gcg ttt ggt   1104
Leu Leu Glu Glu His Asn Val Ala Val Val Pro Gly Ser Ala Phe Gly
        355                 360                 365 gct gaa ggt tac ttc cgc atc tcg ttt gct acc agc atg gaa aac ctg   1152
Ala Glu Gly Tyr Phe Arg Ile Ser Phe Ala Thr Ser Met Glu Asn Leu
    370                 375                 380 cgc gaa gcg ctg gac cgc att gaa aaa gca ctg agc tga               1191
Arg Glu Ala Leu Asp Arg Ile Glu Lys Ala Leu Ser
385                 390                 395
```

<210> SEQ ID NO 38
<211> LENGTH: 396
<212> TYPE: PRT
<213> ORGANISM: Methylophilus methylotrophus

<400> SEQUENCE: 38

```
Val Leu Ser Ala Arg Val Leu Ser Ile Lys Glu Ser Pro Thr Leu Ala
1               5                   10                  15

Ile Thr Ala Lys Ala Ala Lys Tyr Lys Ser Glu Gly Arg Pro Ile Ile
            20                  25                  30

Gly Leu Ala Ala Gly Glu Pro Asp Phe Asp Thr Pro Gln His Ile Lys
        35                  40                  45

Asp Ala Ala Lys Ala Ala Ile Asp Ala Gly Tyr Thr Lys Tyr Thr Pro
    50                  55                  60

Val Ser Gly Ile Pro Ala Leu Lys Lys Ala Ile Val Asn Lys Phe Lys
65                  70                  75                  80
```

```
Asn Glu Asn Gly Phe Asp Tyr Ala Val Asn Glu Val Ile Val Gly Val
                85                  90                  95
Gly Gly Lys Gln Thr Ile Phe Asn Leu Cys Leu Ala Val Leu Asn Pro
            100                 105                 110
Gly Asp Glu Val Ile Val Pro Ala Pro Tyr Trp Val Ser Tyr Ala Asp
        115                 120                 125
Ile Ala Met Val Ala Glu Ala Lys Pro Val Ile Ile Glu Cys Gly Ile
    130                 135                 140
Glu Gln Gly Phe Lys Leu Leu Pro Ala Gln Leu Glu Ser Ala Ile Thr
145                 150                 155                 160
Ala Lys Thr Lys Leu Val Met Phe Asn Ser Pro Ser Asn Pro Thr Gly
                165                 170                 175
Ala Val Tyr Thr Leu Asp Glu Leu Lys Ala Leu Gly Glu Val Leu Leu
            180                 185                 190
Lys His Pro His Val Leu Val Ala Thr Asp Asp Met Tyr Glu His Val
        195                 200                 205
Asn Leu Thr Gly Glu Lys Phe His Asn Ile Leu Asn Ala Ala Pro Gly
    210                 215                 220
Leu Lys Asp Arg Cys Ile Val Leu Asn Gly Val Ser Lys Ala Tyr Ser
225                 230                 235                 240
Met Thr Gly Trp Arg Ile Gly Tyr Ala Ala Gly Pro Ala Tyr Ile Ile
                245                 250                 255
Lys Ala Met Glu Ile Leu Gln Ser Gln Ser Thr Ser Asn Pro Ala Ser
            260                 265                 270
Ile Ser Gln Tyr Ala Ala Glu Ala Ala Leu Ser Gly Ser Gln Asp Cys
        275                 280                 285
Ile Lys Pro Met Val Ala Ala Phe Arg Glu Arg His Lys Tyr Val Val
    290                 295                 300
Asp Arg Phe Asn Ala Ile Pro Gly Leu Ser Cys Leu Met Ala Gly Gly
305                 310                 315                 320
Ala Phe Tyr Ala Phe Pro Asp Ala Arg Gln Ala Ile Thr Asn Leu His
                325                 330                 335
Gln Ala Gly Lys Ile Lys Glu Met Thr Asp Met Ala Leu Ala Glu Tyr
            340                 345                 350
Leu Leu Glu Glu His Asn Val Ala Val Pro Gly Ser Ala Phe Gly
        355                 360                 365
Ala Glu Gly Tyr Phe Arg Ile Ser Phe Ala Thr Ser Met Glu Asn Leu
    370                 375                 380
Arg Glu Ala Leu Asp Arg Ile Glu Lys Ala Leu Ser
385                 390                 395

<210> SEQ ID NO 39
<211> LENGTH: 828
<212> TYPE: DNA
<213> ORGANISM: Methylophilus methylotrophus
<220> FEATURE:
<221> NAME/KEY: CDS
<222> LOCATION: (1)..(828)
<223> OTHER INFORMATION:

<400> SEQUENCE: 39 atg gat cca cgt caa agc att att gaa gcg gct ttt gaa gac cgc gcc    48
Met Asp Pro Arg Gln Ser Ile Ile Glu Ala Ala Phe Glu Asp Arg Ala
1               5                   10                  15 aac atc aac ccg gcc aat gca cca gca gat atc aaa gcc acc gtg gct    96
Asn Ile Asn Pro Ala Asn Ala Pro Ala Asp Ile Lys Ala Thr Val Ala
```

|  |  |
|---|---|
| tca gta ctg gat gat ctg gat gct ggc aaa ttg cgc gtc gca tcc cgg<br>Ser Val Leu Asp Asp Leu Asp Ala Gly Lys Leu Arg Val Ala Ser Arg<br>     35                   40                  45 | 144 |
| att ggc gac acc cag caa tgg gaa acc cat caa tgg atc aag aaa gcc<br>Ile Gly Asp Thr Gln Gln Trp Glu Thr His Gln Trp Ile Lys Lys Ala<br>50                   55                   60 | 192 |
| gtt ctg ctg tct ttc cga ctc aaa gac aac tac ctg atg gat gac ggc<br>Val Leu Leu Ser Phe Arg Leu Lys Asp Asn Tyr Leu Met Asp Asp Gly<br>65                   70                   75               80 | 240 |
| gta act cgt tat ttt gac aaa gtc gat cca aaa ttt gcc aac tac act<br>Val Thr Arg Tyr Phe Asp Lys Val Asp Pro Lys Phe Ala Asn Tyr Thr<br>                85                   90                  95 | 288 |
| gaa gaa gac ttt aaa gcc ggt ggt ttc cgc gtc gtg cct aac gcc att<br>Glu Glu Asp Phe Lys Ala Gly Gly Phe Arg Val Val Pro Asn Ala Ile<br>                100                105              110 | 336 |
| gtc cgc aaa ggc tct ttc att gcc aaa aac gca gtg ttg atg cct tcc<br>Val Arg Lys Gly Ser Phe Ile Ala Lys Asn Ala Val Leu Met Pro Ser<br>              115                120              125 | 384 |
| tat gtc aac atc ggt gct tat gta ggt gaa ggc acc atg gtg gac acc<br>Tyr Val Asn Ile Gly Ala Tyr Val Gly Glu Gly Thr Met Val Asp Thr<br>130                   135                140 | 432 |
| tgg gcg act gtg ggt tcc tgt gcg cag att ggt aaa aat gta cac tta<br>Trp Ala Thr Val Gly Ser Cys Ala Gln Ile Gly Lys Asn Val His Leu<br>145                   150                155              160 | 480 |
| tct ggt ggc gta ggc att ggt ggc gta ttg gag cca gta cag gct ggc<br>Ser Gly Gly Val Gly Ile Gly Gly Val Leu Glu Pro Val Gln Ala Gly<br>                165                170              175 | 528 |
| cca acg att att ggt gac aac tgc ttt atc ggt gca cgt tcc gaa gtg<br>Pro Thr Ile Ile Gly Asp Asn Cys Phe Ile Gly Ala Arg Ser Glu Val<br>                 180                185              190 | 576 |
| gtt gaa ggt gta gtg gta gaa gat aac tgc gtg att tct atg ggt gtc<br>Val Glu Gly Val Val Val Glu Asp Asn Cys Val Ile Ser Met Gly Val<br>              195                200              205 | 624 |
| tat att ggc cag tcg acc aag att tat gac cgt gaa acc ggt gaa gta<br>Tyr Ile Gly Gln Ser Thr Lys Ile Tyr Asp Arg Glu Thr Gly Glu Val<br>210                   215                220 | 672 |
| cac ttt ggt cgc gtg cct gcc ggc tca gtc gtg gta tca ggc aac ctg<br>His Phe Gly Arg Val Pro Ala Gly Ser Val Val Val Ser Gly Asn Leu<br>225                   230                235              240 | 720 |
| cct tcc agc gat ggc aaa tac agc ttg tac tgc gct gtg atc gtg aaa<br>Pro Ser Ser Asp Gly Lys Tyr Ser Leu Tyr Cys Ala Val Ile Val Lys<br>                245                250              255 | 768 |
| aaa gtg gat gcc aag aca ctg ggc aaa gtc ggt atc aac gaa tta ttg<br>Lys Val Asp Ala Lys Thr Leu Gly Lys Val Gly Ile Asn Glu Leu Leu<br>                260                265              270 | 816 |
| cgt ggt gtg taa<br>Arg Gly Val<br>        275 | 828 |

<210> SEQ ID NO 40
<211> LENGTH: 275
<212> TYPE: PRT
<213> ORGANISM: Methylophilus methylotrophus

<400> SEQUENCE: 40

Met Asp Pro Arg Gln Ser Ile Ile Glu Ala Ala Phe Glu Asp Arg Ala
1                 5                   10                 15

Asn Ile Asn Pro Ala Asn Ala Pro Ala Asp Ile Lys Ala Thr Val Ala
               20                 25                 30

```
Ser Val Leu Asp Asp Leu Asp Ala Gly Lys Leu Arg Val Ala Ser Arg
        35                  40                  45

Ile Gly Asp Thr Gln Gln Trp Glu Thr His Gln Trp Ile Lys Lys Ala
 50                  55                  60

Val Leu Leu Ser Phe Arg Leu Lys Asp Asn Tyr Leu Met Asp Asp Gly
 65                  70                  75                  80

Val Thr Arg Tyr Phe Asp Lys Val Asp Pro Lys Phe Ala Asn Tyr Thr
                 85                  90                  95

Glu Glu Asp Phe Lys Ala Gly Gly Phe Arg Val Val Pro Asn Ala Ile
            100                 105                 110

Val Arg Lys Gly Ser Phe Ile Ala Lys Asn Ala Val Leu Met Pro Ser
        115                 120                 125

Tyr Val Asn Ile Gly Ala Tyr Val Gly Glu Gly Thr Met Val Asp Thr
130                 135                 140

Trp Ala Thr Val Gly Ser Cys Ala Gln Ile Gly Lys Asn Val His Leu
145                 150                 155                 160

Ser Gly Gly Val Gly Ile Gly Gly Val Leu Glu Pro Val Gln Ala Gly
                165                 170                 175

Pro Thr Ile Ile Gly Asp Asn Cys Phe Ile Gly Ala Arg Ser Glu Val
            180                 185                 190

Val Glu Gly Val Val Glu Asp Asn Cys Val Ile Ser Met Gly Val
        195                 200                 205

Tyr Ile Gly Gln Ser Thr Lys Ile Tyr Asp Arg Glu Thr Gly Glu Val
210                 215                 220

His Phe Gly Arg Val Pro Ala Gly Ser Val Val Ser Gly Asn Leu
225                 230                 235                 240

Pro Ser Ser Asp Gly Lys Tyr Ser Leu Tyr Cys Ala Val Ile Val Lys
                245                 250                 255

Lys Val Asp Ala Lys Thr Leu Gly Lys Val Gly Ile Asn Glu Leu Leu
            260                 265                 270

Arg Gly Val
        275

<210> SEQ ID NO 41
<211> LENGTH: 1194
<212> TYPE: DNA
<213> ORGANISM: Methylophilus methylotrophus
<220> FEATURE:
<221> NAME/KEY: CDS
<222> LOCATION: (1)..(1194)
<223> OTHER INFORMATION:

<400> SEQUENCE: 41 atg aat cca aat tta aac cac ctc caa ccc tac ccg ttc cag cgt tta    48
Met Asn Pro Asn Leu Asn His Leu Gln Pro Tyr Pro Phe Gln Arg Leu
 1               5                  10                  15 cgt gat ctg ttc cag ggc ctg aca ccc aat ccg gca tac agc cat gtc    96
Arg Asp Leu Phe Gln Gly Leu Thr Pro Asn Pro Ala Tyr Ser His Val
             20                  25                  30 aac ctg tcg att ggt gag cct aaa cac gct aca cca ggc atc atc agc   144
Asn Leu Ser Ile Gly Glu Pro Lys His Ala Thr Pro Gly Ile Ile Ser
         35                  40                  45 gaa gca ctt gca aac aat ttg agt gga ttg gcc agc tat cct acc aca   192
Glu Ala Leu Ala Asn Asn Leu Ser Gly Leu Ala Ser Tyr Pro Thr Thr
     50                  55                  60 atc ggt gtg ccc gcc tta cgg gag gcc atc aat ctc tgg cta caa cgc   240
Ile Gly Val Pro Ala Leu Arg Glu Ala Ile Asn Leu Trp Leu Gln Arg
```

```
                                                                  -continued
65                  70                  75                  80
cgt tac aag att cca gcg ctc aat ata gac aag gcg att ctg cct gtg      288
Arg Tyr Lys Ile Pro Ala Leu Asn Ile Asp Lys Ala Ile Leu Pro Val
                    85                  90                  95 aat ggc agc cgt gag gcc ctg ttc gcg ttt gca caa gct gtg att gat      336
Asn Gly Ser Arg Glu Ala Leu Phe Ala Phe Ala Gln Ala Val Ile Asp
                100                 105                 110 agc agc gcg act caa cag cct gtg gtg att tcc ccc aac ccg ttt tac      384
Ser Ser Ala Thr Gln Gln Pro Val Val Ile Ser Pro Asn Pro Phe Tyr
                115                 120                 125 cag att tac gaa ggt gcg gct ttt ctg gca ggc gca cag ccc tac ttt      432
Gln Ile Tyr Glu Gly Ala Ala Phe Leu Ala Gly Ala Gln Pro Tyr Phe
            130                 135                 140 atc aat acc aca cct gac aac gac tat gtc atg gac ctg aca caa gtt      480
Ile Asn Thr Thr Pro Asp Asn Asp Tyr Val Met Asp Leu Thr Gln Val
145                 150                 155                 160 ccg gtg gaa gtc ctc aaa cga acc caa ctg gta ttt gtc tgc agc cct      528
Pro Val Glu Val Leu Lys Arg Thr Gln Leu Val Phe Val Cys Ser Pro
                165                 170                 175 ggt aac cca tcc ggt aaa gtc atg gat atc cag gct tgg aaa acc ctg      576
Gly Asn Pro Ser Gly Lys Val Met Asp Ile Gln Ala Trp Lys Thr Leu
                180                 185                 190 ttt gag tta tca gat aaa tac gga ttc gtc att gca tca gat gaa tgt      624
Phe Glu Leu Ser Asp Lys Tyr Gly Phe Val Ile Ala Ser Asp Glu Cys
                195                 200                 205 tat tca gaa att tat ttc gat gaa gca caa cct ccg gtc ggt gct ctg      672
Tyr Ser Glu Ile Tyr Phe Asp Glu Ala Gln Pro Pro Val Gly Ala Leu
210                 215                 220 caa gcc gcg cat caa ctc ggt cgc gac gac ttt aaa cgg att gtt atg      720
Gln Ala Ala His Gln Leu Gly Arg Asp Asp Phe Lys Arg Ile Val Met
225                 230                 235                 240 ttc agt tct tta tcc aaa cgc tcc aat gta ccg ggc atg cgc tca ggc      768
Phe Ser Ser Leu Ser Lys Arg Ser Asn Val Pro Gly Met Arg Ser Gly
                245                 250                 255 ttt gtc gcc gga gat gaa gat att att gag aaa ttt aca ctc tat cgt      816
Phe Val Ala Gly Asp Glu Asp Ile Ile Glu Lys Phe Thr Leu Tyr Arg
                260                 265                 270 acc tat cac ggc tgc gcg atg aac ccg gct gtt caa gca gcg agt atc      864
Thr Tyr His Gly Cys Ala Met Asn Pro Ala Val Gln Ala Ala Ser Ile
            275                 280                 285 gtt gcc tgg aat gac gaa aca cat gtt caa cag aac cga gcc ctt tat      912
Val Ala Trp Asn Asp Glu Thr His Val Gln Gln Asn Arg Ala Leu Tyr
            290                 295                 300 cgt gaa aag ttc gca gct gtc acg ccg cgc ttg caa agc gtc tgg ccg      960
Arg Glu Lys Phe Ala Ala Val Thr Pro Arg Leu Gln Ser Val Trp Pro
305                 310                 315                 320 caa acg cac ctt cct gat gca gct ttt tac ctg tgg atc aac acg cag     1008
Gln Thr His Leu Pro Asp Ala Ala Phe Tyr Leu Trp Ile Asn Thr Gln
                325                 330                 335 caa gac gac aca caa gtg gcg aaa aaa ctt tat gaa aat ctc aac att     1056
Gln Asp Asp Thr Gln Val Ala Lys Lys Leu Tyr Glu Asn Leu Asn Ile
                340                 345                 350 aca gta ctg cca ggc tct ttc ctc gct cgc gaa gcc cac gga atg aac     1104
Thr Val Leu Pro Gly Ser Phe Leu Ala Arg Glu Ala His Gly Met Asn
            355                 360                 365 cct gga aaa gga ttt atc cgt atg gcg cta gtt gct tca tat gaa gag     1152
Pro Gly Lys Gly Phe Ile Arg Met Ala Leu Val Ala Ser Tyr Glu Glu
370                 375                 380 aca atc tct gca gca gac agg atg agt gag ttt ttg aaa taa             1194
```

Thr Ile Ser Ala Ala Asp Arg Met Ser Glu Phe Leu Lys
385                 390                 395

<210> SEQ ID NO 42
<211> LENGTH: 397
<212> TYPE: PRT
<213> ORGANISM: Methylophilus methylotrophus

<400> SEQUENCE: 42

Met Asn Pro Asn Leu Asn His Leu Gln Pro Tyr Pro Phe Gln Arg Leu
1               5                   10                  15

Arg Asp Leu Phe Gln Gly Leu Thr Pro Asn Pro Ala Tyr Ser His Val
            20                  25                  30

Asn Leu Ser Ile Gly Glu Pro Lys His Ala Thr Pro Gly Ile Ile Ser
        35                  40                  45

Glu Ala Leu Ala Asn Asn Leu Ser Gly Leu Ala Ser Tyr Pro Thr Thr
    50                  55                  60

Ile Gly Val Pro Ala Leu Arg Glu Ala Ile Asn Leu Trp Leu Gln Arg
65                  70                  75                  80

Arg Tyr Lys Ile Pro Ala Leu Asn Ile Asp Lys Ala Ile Leu Pro Val
            85                  90                  95

Asn Gly Ser Arg Glu Ala Leu Phe Ala Phe Ala Gln Ala Val Ile Asp
        100                 105                 110

Ser Ser Ala Thr Gln Gln Pro Val Val Ile Ser Pro Asn Pro Phe Tyr
    115                 120                 125

Gln Ile Tyr Glu Gly Ala Ala Phe Leu Ala Gly Ala Gln Pro Tyr Phe
130                 135                 140

Ile Asn Thr Thr Pro Asp Asn Asp Tyr Val Met Asp Leu Thr Gln Val
145                 150                 155                 160

Pro Val Glu Val Leu Lys Arg Thr Gln Leu Val Phe Val Cys Ser Pro
            165                 170                 175

Gly Asn Pro Ser Gly Lys Val Met Asp Ile Gln Ala Trp Lys Thr Leu
        180                 185                 190

Phe Glu Leu Ser Asp Lys Tyr Gly Phe Val Ile Ala Ser Asp Glu Cys
    195                 200                 205

Tyr Ser Glu Ile Tyr Phe Asp Glu Ala Gln Pro Pro Val Gly Ala Leu
210                 215                 220

Gln Ala Ala His Gln Leu Gly Arg Asp Asp Phe Lys Arg Ile Val Met
225                 230                 235                 240

Phe Ser Ser Leu Ser Lys Arg Ser Asn Val Pro Gly Met Arg Ser Gly
            245                 250                 255

Phe Val Ala Gly Asp Glu Asp Ile Ile Glu Lys Phe Thr Leu Tyr Arg
        260                 265                 270

Thr Tyr His Gly Cys Ala Met Asn Pro Ala Val Gln Ala Ala Ser Ile
    275                 280                 285

Val Ala Trp Asn Asp Glu Thr His Val Gln Gln Asn Arg Ala Leu Tyr
290                 295                 300

Arg Glu Lys Phe Ala Ala Val Thr Pro Arg Leu Gln Ser Val Trp Pro
305                 310                 315                 320

Gln Thr His Leu Pro Asp Ala Ala Phe Tyr Leu Trp Ile Asn Thr Gln
            325                 330                 335

Gln Asp Asp Thr Gln Val Ala Lys Lys Leu Tyr Glu Asn Leu Asn Ile
        340                 345                 350

Thr Val Leu Pro Gly Ser Phe Leu Ala Arg Glu Ala His Gly Met Asn
    355                 360                 365

```
Pro Gly Lys Gly Phe Ile Arg Met Ala Leu Val Ala Ser Tyr Glu Glu
        370                 375                 380

Thr Ile Ser Ala Ala Asp Arg Met Ser Glu Phe Leu Lys
385                 390                 395

<210> SEQ ID NO 43
<211> LENGTH: 1185
<212> TYPE: DNA
<213> ORGANISM: Methylophilus methylotrophus
<220> FEATURE:
<221> NAME/KEY: CDS
<222> LOCATION: (1)..(1185)
<223> OTHER INFORMATION:

<400> SEQUENCE: 43 atg aaa ccg agt atg ccc aac tgt ttg cca aag aat aag ctt atg tca      48
Met Lys Pro Ser Met Pro Asn Cys Leu Pro Lys Asn Lys Leu Met Ser
1               5                  10                  15 aaa aca ctg gat ctt gcc att gac ctg ctc aaa cgt cgc tca ctg acc      96
Lys Thr Leu Asp Leu Ala Ile Asp Leu Leu Lys Arg Arg Ser Leu Thr
            20                  25                  30 ccg gaa gat gct ggc tgc cag gaa gcc atg att gca cgt ctt gaa ccc     144
Pro Glu Asp Ala Gly Cys Gln Glu Ala Met Ile Ala Arg Leu Glu Pro
        35                  40                  45 ctg ggt ttc aag att gaa cgc atg cgc ttt ggc cag gta gac aac ttt     192
Leu Gly Phe Lys Ile Glu Arg Met Arg Phe Gly Gln Val Asp Asn Phe
    50                  55                  60 tat gcc cgt cgc ggc acc aca ggt ccg ctg att gtg ttc gcc ggg cac     240
Tyr Ala Arg Arg Gly Thr Thr Gly Pro Leu Ile Val Phe Ala Gly His
65                  70                  75                  80 act gac gtg gtg ccc act ggt ccc ctc gac caa tgg cac aca ccg cca     288
Thr Asp Val Val Pro Thr Gly Pro Leu Asp Gln Trp His Thr Pro Pro
                85                  90                  95 ttt gag cca acg att aag gat ggc atg ctg tat gca cgc ggt gca gcc     336
Phe Glu Pro Thr Ile Lys Asp Gly Met Leu Tyr Ala Arg Gly Ala Ala
            100                 105                 110 gac atg aaa acg tca ttg gct gcc ttt gtt acc agc atc gaa gaa ttt     384
Asp Met Lys Thr Ser Leu Ala Ala Phe Val Thr Ser Ile Glu Glu Phe
        115                 120                 125 att gct gaa aac cca aat cac cca ggt tcg att ggc ctg ctg atc aca     432
Ile Ala Glu Asn Pro Asn His Pro Gly Ser Ile Gly Leu Leu Ile Thr
    130                 135                 140 tca gac gaa gag ggc atc gcg att gaa ggg act gtc aaa gtg gtg gaa     480
Ser Asp Glu Glu Gly Ile Ala Ile Glu Gly Thr Val Lys Val Val Glu
145                 150                 155                 160 gcc ctg cag gcc cgc ggc gag act ttt gat tac tgc atc gtc ggt gag     528
Ala Leu Gln Ala Arg Gly Glu Thr Phe Asp Tyr Cys Ile Val Gly Glu
                165                 170                 175 ccc acg agc aat aaa gtc gtt ggc gac atg atc aaa aat ggc cgg cgt     576
Pro Thr Ser Asn Lys Val Val Gly Asp Met Ile Lys Asn Gly Arg Arg
            180                 185                 190 ggt tca ttg tct ggc aag ctc acg gtc aaa ggc atc cag ggc cac att     624
Gly Ser Leu Ser Gly Lys Leu Thr Val Lys Gly Ile Gln Gly His Ile
        195                 200                 205 gcg tat ccg cac ctg gtc aaa aac ccg att cac ctg gcc gca cct gcc     672
Ala Tyr Pro His Leu Val Lys Asn Pro Ile His Leu Ala Ala Pro Ala
    210                 215                 220 att aag gac atg gtg gaa acc gtg tgg gac cac ggt aac gag tat ttc     720
Ile Lys Asp Met Val Glu Thr Val Trp Asp His Gly Asn Glu Tyr Phe
225                 230                 235                 240
```

```
ccc ccc acc tca tgg caa att tcc aac atg aat ggc ggc acc ggg gca      768
Pro Pro Thr Ser Trp Gln Ile Ser Asn Met Asn Gly Gly Thr Gly Ala
            245                 250                 255 acc aat gtg gtc ccc ggt gaa gtc gaa atc ctg ttc aac ttc cgt tat      816
Thr Asn Val Val Pro Gly Glu Val Glu Ile Leu Phe Asn Phe Arg Tyr
            260                 265                 270 tgc ccg gag gtg gag ggt caa ggt agc tcg gag caa agc ctg cgt tcg      864
Cys Pro Glu Val Glu Gly Gln Gly Ser Ser Glu Gln Ser Leu Arg Ser
            275                 280                 285 cgc gtc cat gcc atc ctg gat agc cat ggc ttt gat tac acg ctg gaa      912
Arg Val His Ala Ile Leu Asp Ser His Gly Phe Asp Tyr Thr Leu Glu
            290                 295                 300 tgg gaa cac aac cag tct tac atc acg cct cgc ggt gag ctg gtc gca      960
Trp Glu His Asn Gln Ser Tyr Ile Thr Pro Arg Gly Glu Leu Val Ala
305                 310                 315                 320 gcc atc agc cag gcc ata gag cat agc tac ggc gtc agt cca gag ctc     1008
Ala Ile Ser Gln Ala Ile Glu His Ser Tyr Gly Val Ser Pro Glu Leu
            325                 330                 335 tcc acg acc ggt ggc acc tca gat ggc cgc ttc att gct gac atc tgc     1056
Ser Thr Thr Gly Gly Thr Ser Asp Gly Arg Phe Ile Ala Asp Ile Cys
            340                 345                 350 aag gaa gtg att gag ttc ggg ccg ctg aat gca acg ata cac aaa ctg     1104
Lys Glu Val Ile Glu Phe Gly Pro Leu Asn Ala Thr Ile His Lys Leu
            355                 360                 365 aat gaa tgc gtg gcc gtg gcc gac att gag ccg ctc aag gaa act tac     1152
Asn Glu Cys Val Ala Val Ala Asp Ile Glu Pro Leu Lys Glu Thr Tyr
            370                 375                 380 aaa cgc acc atg gag cta ttg ttg ctg aaa taa                         1185
Lys Arg Thr Met Glu Leu Leu Leu Leu Lys
385                 390
```

<210> SEQ ID NO 44
<211> LENGTH: 394
<212> TYPE: PRT
<213> ORGANISM: Methylophilus methylotrophus

<400> SEQUENCE: 44

```
Met Lys Pro Ser Met Pro Asn Cys Leu Pro Lys Asn Lys Leu Met Ser
1               5                   10                  15

Lys Thr Leu Asp Leu Ala Ile Asp Leu Leu Lys Arg Arg Ser Leu Thr
            20                  25                  30

Pro Glu Asp Ala Gly Cys Gln Glu Ala Met Ile Ala Arg Leu Glu Pro
        35                  40                  45

Leu Gly Phe Lys Ile Glu Arg Met Arg Phe Gly Gln Val Asp Asn Phe
    50                  55                  60

Tyr Ala Arg Arg Gly Thr Thr Gly Pro Leu Ile Val Phe Ala Gly His
65                  70                  75                  80

Thr Asp Val Val Pro Thr Gly Pro Leu Asp Gln Trp His Thr Pro Pro
                85                  90                  95

Phe Glu Pro Thr Ile Lys Asp Gly Met Leu Tyr Ala Arg Gly Ala Ala
            100                 105                 110

Asp Met Lys Thr Ser Leu Ala Ala Phe Val Thr Ser Ile Glu Glu Phe
        115                 120                 125

Ile Ala Glu Asn Pro Asn His Pro Gly Ser Ile Gly Leu Leu Ile Thr
    130                 135                 140

Ser Asp Glu Glu Gly Ile Ala Ile Glu Gly Thr Val Lys Val Val Glu
145                 150                 155                 160

Ala Leu Gln Ala Arg Gly Glu Thr Phe Asp Tyr Cys Ile Val Gly Glu
```

```
                165                 170                 175
Pro Thr Ser Asn Lys Val Val Gly Asp Met Ile Lys Asn Gly Arg Arg
            180                 185                 190

Gly Ser Leu Ser Gly Lys Leu Thr Val Lys Gly Ile Gln Gly His Ile
        195                 200                 205

Ala Tyr Pro His Leu Val Lys Asn Pro Ile His Leu Ala Ala Pro Ala
    210                 215                 220

Ile Lys Asp Met Val Glu Thr Val Trp Asp His Gly Asn Glu Tyr Phe
225                 230                 235                 240

Pro Pro Thr Ser Trp Gln Ile Ser Asn Met Asn Gly Gly Thr Gly Ala
            245                 250                 255

Thr Asn Val Val Pro Gly Glu Val Glu Ile Leu Phe Asn Phe Arg Tyr
        260                 265                 270

Cys Pro Glu Val Glu Gly Gln Gly Ser Ser Glu Gln Ser Leu Arg Ser
    275                 280                 285

Arg Val His Ala Ile Leu Asp Ser His Gly Phe Asp Tyr Thr Leu Glu
        290                 295                 300

Trp Glu His Asn Gln Ser Tyr Ile Thr Pro Arg Gly Glu Leu Val Ala
305                 310                 315                 320

Ala Ile Ser Gln Ala Ile Glu His Ser Tyr Gly Val Ser Pro Glu Leu
            325                 330                 335

Ser Thr Thr Gly Gly Thr Ser Asp Gly Arg Phe Ile Ala Asp Ile Cys
        340                 345                 350

Lys Glu Val Ile Glu Phe Gly Pro Leu Asn Ala Thr Ile His Lys Leu
    355                 360                 365

Asn Glu Cys Val Ala Val Ala Asp Ile Glu Pro Leu Lys Glu Thr Tyr
370                 375                 380

Lys Arg Thr Met Glu Leu Leu Leu Lys
385                 390

<210> SEQ ID NO 45
<211> LENGTH: 831
<212> TYPE: DNA
<213> ORGANISM: Methylophilus methylotrophus
<220> FEATURE:
<221> NAME/KEY: CDS
<222> LOCATION: (1)..(831)
<223> OTHER INFORMATION:

<400> SEQUENCE: 45 atg aaa tta cga ttt acc aaa atg cag ggc gca ggc aat gac ttt gta       48
Met Lys Leu Arg Phe Thr Lys Met Gln Gly Ala Gly Asn Asp Phe Val
1               5                   10                  15 gtg att gat gcg aca aaa agc cct gtg cat ctt tcc cac gcg caa atc       96
Val Ile Asp Ala Thr Lys Ser Pro Val His Leu Ser His Ala Gln Ile
            20                  25                  30 cag cac att gcc aac cgc tac ttt ggt gtt ggt tgt gac cag tta ctg      144
Gln His Ile Ala Asn Arg Tyr Phe Gly Val Gly Cys Asp Gln Leu Leu
        35                  40                  45 atg gtg gaa tcc act gac acg ccc ggc gtt gat ttc cgt tac cgt att      192
Met Val Glu Ser Thr Asp Thr Pro Gly Val Asp Phe Arg Tyr Arg Ile
    50                  55                  60 ttt aac gcc gac ggt ggc gaa gtt gaa caa tgc ggc aat ggc gca cgc      240
Phe Asn Ala Asp Gly Gly Glu Val Glu Gln Cys Gly Asn Gly Ala Arg
65                  70                  75                  80 tgt ttt gta cgc ttt gtg gtc gac aaa ggc ctg act agc aaa cgt gac      288
Cys Phe Val Arg Phe Val Val Asp Lys Gly Leu Thr Ser Lys Arg Asp
                85                  90                  95
```

```
atc cgc gta gaa act gcc agc ggc gtt att acc ctg atg ttg caa gat      336
Ile Arg Val Glu Thr Ala Ser Gly Val Ile Thr Leu Met Leu Gln Asp
        100                 105                 110 gat gga cag gtc acc gtc aac atg ggt gcg cct cgc ttt gcg ccg gcg      384
Asp Gly Gln Val Thr Val Asn Met Gly Ala Pro Arg Phe Ala Pro Ala
    115                 120                 125 cag atc cct ttt gag gct gag caa caa gcg acc act tat gaa tta ccg      432
Gln Ile Pro Phe Glu Ala Glu Gln Gln Ala Thr Thr Tyr Glu Leu Pro
130                 135                 140 cta gct agc gaa acc gtc acc gtg agc gca gtt tcc atg ggc aac ccg      480
Leu Ala Ser Glu Thr Val Thr Val Ser Ala Val Ser Met Gly Asn Pro
145                 150                 155                 160 cat gct gtg atg ctg gtg gat aac gta cac acg gcg gaa gta gcc agc      528
His Ala Val Met Leu Val Asp Asn Val His Thr Ala Glu Val Ala Ser
                165                 170                 175 ctg ggg ccg caa atc gaa tcc cat aca cga ttc ccg caa cgc gtg aat      576
Leu Gly Pro Gln Ile Glu Ser His Thr Arg Phe Pro Gln Arg Val Asn
            180                 185                 190 gcg ggc ttt atg cag gta ctt aat gag cat gaa atc aac ctg cgt gtg      624
Ala Gly Phe Met Gln Val Leu Asn Glu His Glu Ile Asn Leu Arg Val
        195                 200                 205 tat gag cgt ggc agc gga gaa acc ctg gct tgt ggc aca ggc gcc tgc      672
Tyr Glu Arg Gly Ser Gly Glu Thr Leu Ala Cys Gly Thr Gly Ala Cys
    210                 215                 220 gcg gcc gcc gtc agt ggc atc cag ttg ggg act ttg caa agc ccg gtc      720
Ala Ala Ala Val Ser Gly Ile Gln Leu Gly Thr Leu Gln Ser Pro Val
225                 230                 235                 240 aaa gta cat acc cgt ggc ggc atc ctg acc ata caa tgg gca ggc gga      768
Lys Val His Thr Arg Gly Gly Ile Leu Thr Ile Gln Trp Ala Gly Gly
                245                 250                 255 gac acg cct gtc ctc atg acc ggc ccg gca gag att gta ttt gac ggc      816
Asp Thr Pro Val Leu Met Thr Gly Pro Ala Glu Ile Val Phe Asp Gly
            260                 265                 270 gaa att gaa att taa                                                  831
Glu Ile Glu Ile
        275

<210> SEQ ID NO 46
<211> LENGTH: 276
<212> TYPE: PRT
<213> ORGANISM: Methylophilus methylotrophus

<400> SEQUENCE: 46

Met Lys Leu Arg Phe Thr Lys Met Gln Gly Ala Gly Asn Asp Phe Val
1               5                   10                  15

Val Ile Asp Ala Thr Lys Ser Pro Val His Leu Ser His Ala Gln Ile
            20                  25                  30

Gln His Ile Ala Asn Arg Tyr Phe Gly Val Gly Cys Asp Gln Leu Leu
        35                  40                  45

Met Val Glu Ser Thr Asp Thr Pro Gly Val Asp Phe Arg Tyr Arg Ile
    50                  55                  60

Phe Asn Ala Asp Gly Gly Glu Val Glu Gln Cys Gly Asn Gly Ala Arg
65                  70                  75                  80

Cys Phe Val Arg Phe Val Asp Lys Gly Leu Thr Ser Lys Arg Asp
                85                  90                  95

Ile Arg Val Glu Thr Ala Ser Gly Val Ile Thr Leu Met Leu Gln Asp
            100                 105                 110

Asp Gly Gln Val Thr Val Asn Met Gly Ala Pro Arg Phe Ala Pro Ala
```

```
                        115                 120                 125
        Gln Ile Pro Phe Glu Ala Glu Gln Gln Ala Thr Thr Tyr Glu Leu Pro
            130                 135                 140

Leu Ala Ser Glu Thr Val Thr Val Ser Ala Val Ser Met Gly Asn Pro
        145                 150                 155                 160

His Ala Val Met Leu Val Asp Asn Val His Thr Ala Glu Val Ala Ser
                        165                 170                 175

Leu Gly Pro Gln Ile Glu Ser His Thr Arg Phe Pro Gln Arg Val Asn
                    180                 185                 190

Ala Gly Phe Met Gln Val Leu Asn Glu His Glu Ile Asn Leu Arg Val
                195                 200                 205

Tyr Glu Arg Gly Ser Gly Glu Thr Leu Ala Cys Gly Thr Gly Ala Cys
            210                 215                 220

Ala Ala Ala Val Ser Gly Ile Gln Leu Gly Thr Leu Gln Ser Pro Val
        225                 230                 235                 240

Lys Val His Thr Arg Gly Gly Ile Leu Thr Ile Gln Trp Ala Gly Gly
                        245                 250                 255

Asp Thr Pro Val Leu Met Thr Gly Pro Ala Glu Ile Val Phe Asp Gly
                    260                 265                 270

Glu Ile Glu Ile
                275

<210> SEQ ID NO 47
<211> LENGTH: 1128
<212> TYPE: DNA
<213> ORGANISM: Methylophilus methylotrophus
<220> FEATURE:
<221> NAME/KEY: CDS
<222> LOCATION: (1)..(1128)
<223> OTHER INFORMATION:

<400> SEQUENCE: 47 atg tct gaa tcg aat tct gtt ggt atc gtt aaa gcg cag gtt gcg cac      48
Met Ser Glu Ser Asn Ser Val Gly Ile Val Lys Ala Gln Val Ala His
1               5                   10                  15 ttc acc cag ccg ctg acc ctt aaa agc ggc gct gtg ttg cca caa tac      96
Phe Thr Gln Pro Leu Thr Leu Lys Ser Gly Ala Val Leu Pro Gln Tyr
                20                  25                  30 cat ctt gct tat gaa acc tat ggt gaa ctc aac gcg gcc aaa acc aat     144
His Leu Ala Tyr Glu Thr Tyr Gly Glu Leu Asn Ala Ala Lys Thr Asn
            35                  40                  45 gcg gta ttg att tgt cac gcc ttg tcc ggc aat cat cat gtc gct ggt     192
Ala Val Leu Ile Cys His Ala Leu Ser Gly Asn His His Val Ala Gly
        50                  55                  60 cgc tat tcg ccg gaa gat aaa tat cct ggc tgg tgg gat aac ctt gtt     240
Arg Tyr Ser Pro Glu Asp Lys Tyr Pro Gly Trp Trp Asp Asn Leu Val
65                  70                  75                  80 ggc ccc ggt aag cca ctg gat acc aac aag ttt ttt gtg att ggc ctc     288
Gly Pro Gly Lys Pro Leu Asp Thr Asn Lys Phe Phe Val Ile Gly Leu
                85                  90                  95 aac aat ctg ggc ggc tgt cac ggt agt agc ggc cct tcc agc gta aat     336
Asn Asn Leu Gly Gly Cys His Gly Ser Ser Gly Pro Ser Ser Val Asn
                100                 105                 110 cca ctc act gac cgg cct tac agt gca acg ttc cca gtc gtg acg gta     384
Pro Leu Thr Asp Arg Pro Tyr Ser Ala Thr Phe Pro Val Val Thr Val
            115                 120                 125 gaa gac tgg gtg gaa tct cag gcg cgc ctg ttg gat tat ctt gga att     432
Glu Asp Trp Val Glu Ser Gln Ala Arg Leu Leu Asp Tyr Leu Gly Ile
        130                 135                 140
```

```
gac caa ctg gca gcc gtg att ggt ggc agc ctg gga ggc atg caa gcg    480
Asp Gln Leu Ala Ala Val Ile Gly Gly Ser Leu Gly Gly Met Gln Ala
145                 150                 155                 160 ctg cac tgg aat att gtc tac ccc gag cgt gta cgg cat gcc ttt gtc    528
Leu His Trp Asn Ile Val Tyr Pro Glu Arg Val Arg His Ala Phe Val
                165                 170                 175 att gcc tct gcg ccc aac ctg acc gca cag aac atg gcc ttt aac gaa    576
Ile Ala Ser Ala Pro Asn Leu Thr Ala Gln Asn Met Ala Phe Asn Glu
            180                 185                 190 gtg gca cgc cag gcg att att acc gac ccc gag ttt ttt gac ggc gat    624
Val Ala Arg Gln Ala Ile Ile Thr Asp Pro Glu Phe Phe Asp Gly Asp
        195                 200                 205 tat tat aat cat ggc acc gtc ccc cgc cgc ggc ttg cgt att gcc cgt    672
Tyr Tyr Asn His Gly Thr Val Pro Arg Arg Gly Leu Arg Ile Ala Arg
    210                 215                 220 atg ctg ggg cat atc acc tac ttg tca gat gac gcc atg ggt gaa aaa    720
Met Leu Gly His Ile Thr Tyr Leu Ser Asp Asp Ala Met Gly Glu Lys
225                 230                 235                 240 ttt ggc cgc aaa ttg cgc cat ggc gat gtg aag tac agc ttt gat gtc    768
Phe Gly Arg Lys Leu Arg His Gly Asp Val Lys Tyr Ser Phe Asp Val
                245                 250                 255 gaa ttt gaa atg gaa tct tac ttg cgc tat cag ggc gac aag ttt gcc    816
Glu Phe Glu Met Glu Ser Tyr Leu Arg Tyr Gln Gly Asp Lys Phe Ala
            260                 265                 270 ggg gaa ttt gat gcc aac acc tat ttg cgc atg aca cgc gca ctg gac    864
Gly Glu Phe Asp Ala Asn Thr Tyr Leu Arg Met Thr Arg Ala Leu Asp
        275                 280                 285 tat ttt gac ccg gcc ctc gat tat gac ggc aat tta agc aag gcg ctc    912
Tyr Phe Asp Pro Ala Leu Asp Tyr Asp Gly Asn Leu Ser Lys Ala Leu
    290                 295                 300 agc cgt gcc aag gcc aag ttt gtc gtc atc tcg ttt acc act gac tgg    960
Ser Arg Ala Lys Ala Lys Phe Val Val Ile Ser Phe Thr Thr Asp Trp
305                 310                 315                 320 cgc ttt tcg cct gcc cgc tca cgc gaa att gtc cag gcc ttg ctg gat   1008
Arg Phe Ser Pro Ala Arg Ser Arg Glu Ile Val Gln Ala Leu Leu Asp
                325                 330                 335 aac gcc ttg ccc gtc aaa tat gcc gag gta act tct gcc cat ggc cat   1056
Asn Ala Leu Pro Val Lys Tyr Ala Glu Val Thr Ser Ala His Gly His
            340                 345                 350 gac gct ttc ttg atg ccg gat gcg cat tac cac gcc atc atg cgc gcc   1104
Asp Ala Phe Leu Met Pro Asp Ala His Tyr His Ala Ile Met Arg Ala
        355                 360                 365 tac ctg gag caa atc aaa gta tga                                    1128
Tyr Leu Glu Gln Ile Lys Val
    370                 375

<210> SEQ ID NO 48
<211> LENGTH: 375
<212> TYPE: PRT
<213> ORGANISM: Methylophilus methylotrophus

<400> SEQUENCE: 48

Met Ser Glu Ser Asn Ser Val Gly Ile Val Lys Ala Gln Val Ala His
1               5                   10                  15

Phe Thr Gln Pro Leu Thr Leu Lys Ser Gly Ala Val Leu Pro Gln Tyr
            20                  25                  30

His Leu Ala Tyr Glu Thr Tyr Gly Glu Leu Asn Ala Ala Lys Thr Asn
        35                  40                  45

Ala Val Leu Ile Cys His Ala Leu Ser Gly Asn His His Val Ala Gly
```

```
                 50                  55                  60
Arg Tyr Ser Pro Glu Asp Lys Tyr Pro Gly Trp Trp Asp Asn Leu Val
 65                  70                  75                  80

Gly Pro Gly Lys Pro Leu Asp Thr Asn Lys Phe Phe Val Ile Gly Leu
                 85                  90                  95

Asn Asn Leu Gly Gly Cys His Gly Ser Ser Gly Pro Ser Ser Val Asn
                100                 105                 110

Pro Leu Thr Asp Arg Pro Tyr Ser Ala Thr Phe Pro Val Val Thr Val
                115                 120                 125

Glu Asp Trp Val Glu Ser Gln Ala Arg Leu Leu Asp Tyr Leu Gly Ile
130                 135                 140

Asp Gln Leu Ala Ala Val Ile Gly Gly Ser Leu Gly Gly Met Gln Ala
145                 150                 155                 160

Leu His Trp Asn Ile Val Tyr Pro Glu Arg Val Arg His Ala Phe Val
                165                 170                 175

Ile Ala Ser Ala Pro Asn Leu Thr Ala Gln Asn Met Ala Phe Asn Glu
                180                 185                 190

Val Ala Arg Gln Ala Ile Ile Thr Asp Pro Glu Phe Phe Asp Gly Asp
                195                 200                 205

Tyr Tyr Asn His Gly Thr Val Pro Arg Arg Gly Leu Arg Ile Ala Arg
210                 215                 220

Met Leu Gly His Ile Thr Tyr Leu Ser Asp Asp Ala Met Gly Glu Lys
225                 230                 235                 240

Phe Gly Arg Lys Leu Arg His Gly Asp Val Lys Tyr Ser Phe Asp Val
                245                 250                 255

Glu Phe Glu Met Glu Ser Tyr Leu Arg Tyr Gln Gly Asp Lys Phe Ala
                260                 265                 270

Gly Glu Phe Asp Ala Asn Thr Tyr Leu Arg Met Thr Arg Ala Leu Asp
                275                 280                 285

Tyr Phe Asp Pro Ala Leu Asp Tyr Asp Gly Asn Leu Ser Lys Ala Leu
                290                 295                 300

Ser Arg Ala Lys Ala Lys Phe Val Val Ile Ser Phe Thr Thr Asp Trp
305                 310                 315                 320

Arg Phe Ser Pro Ala Arg Ser Arg Glu Ile Val Gln Ala Leu Leu Asp
                325                 330                 335

Asn Ala Leu Pro Val Lys Tyr Ala Glu Val Thr Ser Ala His Gly His
                340                 345                 350

Asp Ala Phe Leu Met Pro Asp Ala His Tyr His Ala Ile Met Arg Ala
                355                 360                 365

Tyr Leu Glu Gln Ile Lys Val
                370                 375

<210> SEQ ID NO 49
<211> LENGTH: 1272
<212> TYPE: DNA
<213> ORGANISM: Methylophilus methylotrophus
<220> FEATURE:
<221> NAME/KEY: CDS
<222> LOCATION: (1)..(1272)
<223> OTHER INFORMATION:

<400> SEQUENCE: 49 atg aag caa gag acc ata tat atc cat ggc ggc tat caa cca gac ccc      48
Met Lys Gln Glu Thr Ile Tyr Ile His Gly Gly Tyr Gln Pro Asp Pro
 1               5                  10                  15 act acc aag gcg gtt gcg gtg ccc att tac caa acg acc tct tat gcg      96
```

```
                    Thr Thr Lys Ala Val Ala Val Pro Ile Tyr Gln Thr Thr Ser Tyr Ala
                                 20                  25                  30 ttt gat aat act cag cat ggc gca gac ctg ttt gac ctc aag gta cag             144
Phe Asp Asn Thr Gln His Gly Ala Asp Leu Phe Asp Leu Lys Val Gln
             35                  40                  45 ggc aat ata tac acc cgc att atg aat ccc acc act gcg gta cta gaa             192
Gly Asn Ile Tyr Thr Arg Ile Met Asn Pro Thr Thr Ala Val Leu Glu
 50                  55                  60 gag agg ctt gca caa ctg gaa ggc ggc att ggc gca ttg gca ttg gct             240
Glu Arg Leu Ala Gln Leu Glu Gly Gly Ile Gly Ala Leu Ala Leu Ala
 65                  70                  75                  80 tct ggc atg gcc gcc att acc tac gcg att caa acc att gcc gag gca             288
Ser Gly Met Ala Ala Ile Thr Tyr Ala Ile Gln Thr Ile Ala Glu Ala
                 85                  90                  95 ggc gat aat att gtt tct gtc tcc aca ctc tat ggc ggc acc tat aac             336
Gly Asp Asn Ile Val Ser Val Ser Thr Leu Tyr Gly Gly Thr Tyr Asn
                100                 105                 110 ttt ttt gcg cac acc ttg ccc aag caa ggt ata gaa gtc aga ttt ttt             384
Phe Phe Ala His Thr Leu Pro Lys Gln Gly Ile Glu Val Arg Phe Phe
            115                 120                 125 gat tac cgc gac ccg gct tca ctg gaa aaa ctc atc gac agc cgc acc             432
Asp Tyr Arg Asp Pro Ala Ser Leu Glu Lys Leu Ile Asp Ser Arg Thr
            130                 135                 140 aaa cta gtg ttt gct gaa acc ata ggc aac ccg ctc ggc aat gtg gtc             480
Lys Leu Val Phe Ala Glu Thr Ile Gly Asn Pro Leu Gly Asn Val Val
145                 150                 155                 160 gat ctc gcc gcc atc agc gcc gcc gcg cat aaa cat ggc gta ccg gtg             528
Asp Leu Ala Ala Ile Ser Ala Ala Ala His Lys His Gly Val Pro Val
                165                 170                 175 att gtc gat aac acc gtc gcc acg ccc att cta tcg cgt cca ttt gag             576
Ile Val Asp Asn Thr Val Ala Thr Pro Ile Leu Ser Arg Pro Phe Glu
                180                 185                 190 cat ggc gtg gat att gtg gtg cac tcg cta acc aaa tac atc ggc ggt             624
His Gly Val Asp Ile Val Val His Ser Leu Thr Lys Tyr Ile Gly Gly
            195                 200                 205 cac ggc aac tcg att ggc ggt atc atc gtc gat agc ggc aaa ttc cca             672
His Gly Asn Ser Ile Gly Gly Ile Ile Val Asp Ser Gly Lys Phe Pro
            210                 215                 220 tgg ggc gag cac gct aaa cgc ttc acc agc ctc aac acc ccg gac ccc             720
Trp Gly Glu His Ala Lys Arg Phe Thr Ser Leu Asn Thr Pro Asp Pro
225                 230                 235                 240 agc tat cat ggc gtc aac tac gtc gag gca tta ggc ccc gcc gcc tac             768
Ser Tyr His Gly Val Asn Tyr Val Glu Ala Leu Gly Pro Ala Ala Tyr
                245                 250                 255 atc gcc cgc gcc cgc gtc gtg ccc ttg cgc aac acc ggc gcc gcc atc             816
Ile Ala Arg Ala Arg Val Val Pro Leu Arg Asn Thr Gly Ala Ala Ile
                260                 265                 270 agc cca ttt aac agt ttt ttg att ctg caa ggc ctg gaa acg ctt gca             864
Ser Pro Phe Asn Ser Phe Leu Ile Leu Gln Gly Leu Glu Thr Leu Ala
            275                 280                 285 ctt aga att gaa aga cac agc acc aac gct ctg gca atc gca aat tat             912
Leu Arg Ile Glu Arg His Ser Thr Asn Ala Leu Ala Ile Ala Asn Tyr
            290                 295                 300 ctg aaa aac cat ccc aaa gtg aaa tgg gtc aga tac gcc ggg ctt gaa             960
Leu Lys Asn His Pro Lys Val Lys Trp Val Arg Tyr Ala Gly Leu Glu
305                 310                 315                 320 gac cat ccc gac cat gca ctg gtg aaa aaa tac ctc aac ggc cac gcc            1008
Asp His Pro Asp His Ala Leu Val Lys Lys Tyr Leu Asn Gly His Ala
                325                 330                 335
```

-continued

```
tca ggc att ttg tct ttt ggc gta caa gac ggc cgc gaa ggc ggc acc      1056
Ser Gly Ile Leu Ser Phe Gly Val Gln Asp Gly Arg Glu Gly Gly Thr
        340                 345                 350 cgc ttt att gac gcg ctg caa ctg ttc aca cgc ttg gtc aat att ggc      1104
Arg Phe Ile Asp Ala Leu Gln Leu Phe Thr Arg Leu Val Asn Ile Gly
355                 360                 365 gat gca aaa agc ctc gct tgc cac ccc gct acc acc acc cac cgt caa      1152
Asp Ala Lys Ser Leu Ala Cys His Pro Ala Thr Thr Thr His Arg Gln
    370                 375                 380 ctc aat gca gaa gaa ctg gca cgt gca ggt gtg agc gaa gat atg gtc      1200
Leu Asn Ala Glu Glu Leu Ala Arg Ala Gly Val Ser Glu Asp Met Val
385                 390                 395                 400 agg tta tcg gta ggc att gag cat atc gat gat ttg att gca gat ttg      1248
Arg Leu Ser Val Gly Ile Glu His Ile Asp Asp Leu Ile Ala Asp Leu
                405                 410                 415 gag caa gca ctg gcg aag gtt taa                                      1272
Glu Gln Ala Leu Ala Lys Val
                420
```

<210> SEQ ID NO 50
<211> LENGTH: 423
<212> TYPE: PRT
<213> ORGANISM: Methylophilus methylotrophus

<400> SEQUENCE: 50

```
Met Lys Gln Glu Thr Ile Tyr Ile His Gly Gly Tyr Gln Pro Asp Pro
1               5                   10                  15

Thr Thr Lys Ala Val Ala Val Pro Ile Tyr Gln Thr Thr Ser Tyr Ala
            20                  25                  30

Phe Asp Asn Thr Gln His Gly Ala Asp Leu Phe Asp Leu Lys Val Gln
        35                  40                  45

Gly Asn Ile Tyr Thr Arg Ile Met Asn Pro Thr Thr Ala Val Leu Glu
    50                  55                  60

Glu Arg Leu Ala Gln Leu Glu Gly Gly Ile Gly Ala Leu Ala Leu Ala
65                  70                  75                  80

Ser Gly Met Ala Ala Ile Thr Tyr Ala Ile Gln Thr Ile Ala Glu Ala
                85                  90                  95

Gly Asp Asn Ile Val Ser Val Ser Thr Leu Tyr Gly Gly Thr Tyr Asn
            100                 105                 110

Phe Phe Ala His Thr Leu Pro Lys Gln Gly Ile Glu Val Arg Phe Phe
        115                 120                 125

Asp Tyr Arg Asp Pro Ala Ser Leu Glu Lys Leu Ile Asp Ser Arg Thr
    130                 135                 140

Lys Leu Val Phe Ala Glu Thr Ile Gly Asn Pro Leu Gly Asn Val Val
145                 150                 155                 160

Asp Leu Ala Ala Ile Ser Ala Ala His Lys His Gly Val Pro Val
                165                 170                 175

Ile Val Asp Asn Thr Val Ala Thr Pro Ile Leu Ser Arg Pro Phe Glu
            180                 185                 190

His Gly Val Asp Ile Val His Ser Leu Thr Lys Tyr Ile Gly Gly
        195                 200                 205

His Gly Asn Ser Ile Gly Gly Ile Ile Val Asp Ser Gly Lys Phe Pro
    210                 215                 220

Trp Gly Glu His Ala Lys Arg Phe Thr Ser Leu Asn Thr Pro Asp Pro
225                 230                 235                 240

Ser Tyr His Gly Val Asn Tyr Val Glu Ala Leu Gly Pro Ala Ala Tyr
                245                 250                 255
```

-continued

```
Ile Ala Arg Ala Arg Val Val Pro Leu Arg Asn Thr Gly Ala Ala Ile
            260                 265                 270

Ser Pro Phe Asn Ser Phe Leu Ile Leu Gln Gly Leu Glu Thr Leu Ala
            275                 280                 285

Leu Arg Ile Glu Arg His Ser Thr Asn Ala Leu Ala Ile Ala Asn Tyr
            290                 295                 300

Leu Lys Asn His Pro Lys Val Lys Trp Val Arg Tyr Ala Gly Leu Glu
305                 310                 315                 320

Asp His Pro Asp His Ala Leu Val Lys Lys Tyr Leu Asn Gly His Ala
                325                 330                 335

Ser Gly Ile Leu Ser Phe Gly Val Gln Asp Gly Arg Glu Gly Gly Thr
            340                 345                 350

Arg Phe Ile Asp Ala Leu Gln Leu Phe Thr Arg Leu Val Asn Ile Gly
            355                 360                 365

Asp Ala Lys Ser Leu Ala Cys His Pro Ala Thr Thr Thr His Arg Gln
            370                 375                 380

Leu Asn Ala Glu Glu Leu Ala Arg Ala Gly Val Ser Glu Asp Met Val
385                 390                 395                 400

Arg Leu Ser Val Gly Ile Glu His Ile Asp Asp Leu Ile Ala Asp Leu
                405                 410                 415

Glu Gln Ala Leu Ala Lys Val
            420
```

<210> SEQ ID NO 51
<211> LENGTH: 927
<212> TYPE: DNA
<213> ORGANISM: Methylophilus methylotrophus
<220> FEATURE:
<221> NAME/KEY: CDS
<222> LOCATION: (1)..(927)
<223> OTHER INFORMATION:

<400> SEQUENCE: 51

```
atg tct gtt ttt acc acg ctg agt ttg gat gaa gtg cgc cag tgg ctg      48
Met Ser Val Phe Thr Thr Leu Ser Leu Asp Glu Val Arg Gln Trp Leu
1               5                   10                  15 gcg cct ttt aat gtc ggt gag ttg cac aca tta cgt ggc att gct gcc      96
Ala Pro Phe Asn Val Gly Glu Leu His Thr Leu Arg Gly Ile Ala Ala
                20                  25                  30 ggg atc acc aat acc aat tat ttc gtc gaa acc agt cag gcg cgc ttt     144
Gly Ile Thr Asn Thr Asn Tyr Phe Val Glu Thr Ser Gln Ala Arg Phe
            35                  40                  45 gtg ctg acg gtg ttt gaa aaa aat gat ttt gac gag ttg cct tat ttc     192
Val Leu Thr Val Phe Glu Lys Asn Asp Phe Asp Glu Leu Pro Tyr Phe
        50                  55                  60 gtg cac ttg atg act cat ctg tca cgg cat gat att ccg tgt ccc aaa     240
Val His Leu Met Thr His Leu Ser Arg His Asp Ile Pro Cys Pro Lys
65                  70                  75                  80 cca att gtg gac cag aac aac act gcc ttg cat cgc att cac ggt aaa     288
Pro Ile Val Asp Gln Asn Asn Thr Ala Leu His Arg Ile His Gly Lys
                85                  90                  95 ccc gcc ttg atg gtg agt tgc ctg cga ggc agc gat gtc agc cag ccc     336
Pro Ala Leu Met Val Ser Cys Leu Arg Gly Ser Asp Val Ser Gln Pro
            100                 105                 110 aat tta aag cag att gag gcg gtg gca cgg aca ttg gcg cgc ctg cat     384
Asn Leu Lys Gln Ile Glu Ala Val Ala Arg Thr Leu Ala Arg Leu His
        115                 120                 125 gtg gcc ggc ttg gat ttt cat gag cag tcg cac aat caa cgt ggc caa     432
```

```
Val Ala Gly Leu Asp Phe His Glu Gln Ser His Asn Gln Arg Gly Gln
    130                 135                 140 ggc tgg cgt gtc atg act gcg caa cag gtg atg cca aaa ctg gca cct      480
Gly Trp Arg Val Met Thr Ala Gln Gln Val Met Pro Lys Leu Ala Pro
145                 150                 155                 160 gtc cag cag cat ctc ttg cag gaa gaa tta gag ttc cag cat ggc ctg      528
Val Gln Gln His Leu Leu Gln Glu Glu Leu Glu Phe Gln His Gly Leu
                165                 170                 175 gat ttg tca cgt ttg cca cat ggc gtg att cac ggt gac ctg ttc cgt      576
Asp Leu Ser Arg Leu Pro His Gly Val Ile His Gly Asp Leu Phe Arg
            180                 185                 190 gac aat gtg ctt ttt gat ggc gat gtg ctc ggc ggc ttt att gac ttt      624
Asp Asn Val Leu Phe Asp Gly Asp Val Leu Gly Gly Phe Ile Asp Phe
        195                 200                 205 tat tat gcc tgc cat gat gtc ctc gcc tat gat gtg gcg att gcg gtc      672
Tyr Tyr Ala Cys His Asp Val Leu Ala Tyr Asp Val Ala Ile Ala Val
    210                 215                 220 aac gaa tgg tgt gtg gat agc acc ggc aac ttt gtg gat gag aaa ctg      720
Asn Glu Trp Cys Val Asp Ser Thr Gly Asn Phe Val Asp Glu Lys Leu
225                 230                 235                 240 gca gca ttc atg aat gcc tac cag tcc gag cgg cca ttt acc gag gct      768
Ala Ala Phe Met Asn Ala Tyr Gln Ser Glu Arg Pro Phe Thr Glu Ala
                245                 250                 255 gaa aaa acc cat tgg cct gcc ttg ttg cgc cgg gct gcc ttg cgc ttc      816
Glu Lys Thr His Trp Pro Ala Leu Leu Arg Arg Ala Ala Leu Arg Phe
            260                 265                 270 tgg ctc tcg cgc ctg tat gat ttt tat tat ccg gtg gcg ggt gaa ctg      864
Trp Leu Ser Arg Leu Tyr Asp Phe Tyr Tyr Pro Val Ala Gly Glu Leu
        275                 280                 285 aca cat gca aaa gac ccg gcg cat ttc gaa cgg gtg ctg tta aat cgt      912
Thr His Ala Lys Asp Pro Ala His Phe Glu Arg Val Leu Leu Asn Arg
    290                 295                 300 aaa gct ttg act taa                                                   927
Lys Ala Leu Thr
305
```

<210> SEQ ID NO 52
<211> LENGTH: 308
<212> TYPE: PRT
<213> ORGANISM: Methylophilus methylotrophus

<400> SEQUENCE: 52

```
Met Ser Val Phe Thr Thr Leu Ser Leu Asp Glu Val Arg Gln Trp Leu
1               5                   10                  15

Ala Pro Phe Asn Val Gly Glu Leu His Thr Leu Arg Gly Ile Ala Ala
            20                  25                  30

Gly Ile Thr Asn Thr Asn Tyr Phe Val Glu Thr Ser Gln Ala Arg Phe
        35                  40                  45

Val Leu Thr Val Phe Glu Lys Asn Asp Phe Asp Glu Leu Pro Tyr Phe
    50                  55                  60

Val His Leu Met Thr His Leu Ser Arg His Asp Ile Pro Cys Pro Lys
65                  70                  75                  80

Pro Ile Val Asp Gln Asn Asn Thr Ala Leu His Arg Ile His Gly Lys
                85                  90                  95

Pro Ala Leu Met Val Ser Cys Leu Arg Gly Ser Asp Val Ser Gln Pro
            100                 105                 110

Asn Leu Lys Gln Ile Glu Ala Val Ala Arg Thr Leu Ala Arg Leu His
        115                 120                 125
```

```
Val Ala Gly Leu Asp Phe His Glu Gln Ser His Asn Gln Arg Gly Gln
    130                 135                 140
Gly Trp Arg Val Met Thr Ala Gln Gln Val Met Pro Lys Leu Ala Pro
145                 150                 155                 160
Val Gln Gln His Leu Leu Gln Glu Glu Leu Glu Phe Gln His Gly Leu
                165                 170                 175
Asp Leu Ser Arg Leu Pro His Gly Val Ile His Gly Asp Leu Phe Arg
            180                 185                 190
Asp Asn Val Leu Phe Asp Gly Asp Val Leu Gly Gly Phe Ile Asp Phe
        195                 200                 205
Tyr Tyr Ala Cys His Asp Val Leu Ala Tyr Asp Val Ala Ile Ala Val
    210                 215                 220
Asn Glu Trp Cys Val Asp Ser Thr Gly Asn Phe Val Asp Glu Lys Leu
225                 230                 235                 240
Ala Ala Phe Met Asn Ala Tyr Gln Ser Glu Arg Pro Phe Thr Glu Ala
                245                 250                 255
Glu Lys Thr His Trp Pro Ala Leu Leu Arg Arg Ala Ala Leu Arg Phe
                260                 265                 270
Trp Leu Ser Arg Leu Tyr Asp Phe Tyr Pro Val Ala Gly Glu Leu
        275                 280                 285
Thr His Ala Lys Asp Pro Ala His Phe Glu Arg Val Leu Leu Asn Arg
    290                 295                 300

Lys Ala Leu Thr
305
```

<210> SEQ ID NO 53
<211> LENGTH: 1434
<212> TYPE: DNA
<213> ORGANISM: Methylophilus methylotrophus
<220> FEATURE:
<221> NAME/KEY: CDS
<222> LOCATION: (1)..(1434)
<223> OTHER INFORMATION:

<400> SEQUENCE: 53

| | | |
|---|---|---|
| atg aaa tat atc agt acc cgc ggg cag tcg cct gct tta aca ttt agt<br>Met Lys Tyr Ile Ser Thr Arg Gly Gln Ser Pro Ala Leu Thr Phe Ser<br>1               5                   10                  15 | 48 |
| gaa atc ttg ctg ggc ggc ctc gcg cct gac ggc ggt tta tat ctg cct<br>Glu Ile Leu Leu Gly Gly Leu Ala Pro Asp Gly Gly Leu Tyr Leu Pro<br>            20                  25                  30 | 96 |
| gag caa tat ccg caa ttc agt gat gca gat ttg aat gcc atg cgt ggc<br>Glu Gln Tyr Pro Gln Phe Ser Asp Ala Asp Leu Asn Ala Met Arg Gly<br>        35                  40                  45 | 144 |
| atg aat tat cgc gaa ctg gct ttt gca atc ttg tcc agg ctg gtc gat<br>Met Asn Tyr Arg Glu Leu Ala Phe Ala Ile Leu Ser Arg Leu Val Asp<br>    50                  55                  60 | 192 |
| gac agt gat att ccc cac gca gac ctg aaa gcg att att gat aaa acc<br>Asp Ser Asp Ile Pro His Ala Asp Leu Lys Ala Ile Ile Asp Lys Thr<br>65                  70                  75                  80 | 240 |
| tac cgc gca gac gtg tac caa tat gta cgc gca ggc cag aat gcc gaa<br>Tyr Arg Ala Asp Val Tyr Gln Tyr Val Arg Ala Gly Gln Asn Ala Glu<br>                85                  90                  95 | 288 |
| gac att acg cct acg ctc aag cta gaa gat aac ctc tac ctg ctt agc<br>Asp Ile Thr Pro Thr Leu Lys Leu Glu Asp Asn Leu Tyr Leu Leu Ser<br>            100                 105                 110 | 336 |
| ctg tct aac ggc cca aca tta gcc ttt aaa gac atg gcg atg cag tta<br>Leu Ser Asn Gly Pro Thr Leu Ala Phe Lys Asp Met Ala Met Gln Leu<br>        115                 120                 125 | 384 |

-continued

```
ctg ggc aat ctg ttt gaa tac gta ctg acc aaa act ggc caa acc act      432
Leu Gly Asn Leu Phe Glu Tyr Val Leu Thr Lys Thr Gly Gln Thr Thr
    130                 135                 140 aat atc ctg ggt gct act tct ggt gat acc ggc tct gcg gct gag tat      480
Asn Ile Leu Gly Ala Thr Ser Gly Asp Thr Gly Ser Ala Ala Glu Tyr
145                 150                 155                 160 gcg atg cgc ggt aaa aaa ggt gtg cgt gtg ttc atg ctg tcg cca tac      528
Ala Met Arg Gly Lys Lys Gly Val Arg Val Phe Met Leu Ser Pro Tyr
                165                 170                 175 cag aag atg agc cgt ttc cag acc gcc caa atg ttc agc ctg caa gac      576
Gln Lys Met Ser Arg Phe Gln Thr Ala Gln Met Phe Ser Leu Gln Asp
            180                 185                 190 gac aat att ttc aat att gcg gtg aaa ggt gtc ttc gat gat gcg cag      624
Asp Asn Ile Phe Asn Ile Ala Val Lys Gly Val Phe Asp Asp Ala Gln
        195                 200                 205 gat atg gtc aag gcc gtt tct aat gat cat aac ttt aaa gcc caa tac      672
Asp Met Val Lys Ala Val Ser Asn Asp His Asn Phe Lys Ala Gln Tyr
    210                 215                 220 aaa atc ggc gcg gtg aac tcc att aac tgg ggt cgt att gct gcc cag      720
Lys Ile Gly Ala Val Asn Ser Ile Asn Trp Gly Arg Ile Ala Ala Gln
225                 230                 235                 240 att att tac tat ttc aaa ggt tac ttg gct gtg acg act aac aac agc      768
Ile Ile Tyr Tyr Phe Lys Gly Tyr Leu Ala Val Thr Thr Asn Asn Ser
                245                 250                 255 cag aaa gtc agt ttt act gtg cct agt ggc aac ttt ggt aac atc tgt      816
Gln Lys Val Ser Phe Thr Val Pro Ser Gly Asn Phe Gly Asn Ile Cys
            260                 265                 270 gcc ggg cac att gca cgc atg atg ggt tta ccg att gac cag ctg gtg      864
Ala Gly His Ile Ala Arg Met Met Gly Leu Pro Ile Asp Gln Leu Val
        275                 280                 285 gtg gca acc aat gaa aac gat gtg ctg gat gag ttt ttt aat act ggc      912
Val Ala Thr Asn Glu Asn Asp Val Leu Asp Glu Phe Phe Asn Thr Gly
    290                 295                 300 gtt tat gcg ccg cgt ggt tca gcc aat act tat cat acc tcc agc ccg      960
Val Tyr Ala Pro Arg Gly Ser Ala Asn Thr Tyr His Thr Ser Ser Pro
305                 310                 315                 320 tcc atg gat atc agc aaa gcc tcc aac ttt gag cgc ttt gtc tat gac     1008
Ser Met Asp Ile Ser Lys Ala Ser Asn Phe Glu Arg Phe Val Tyr Asp
                325                 330                 335 ctc gtc ggt cag gac agt gcc cgt gtg cgt gaa ttg tgg acc gcg gtg     1056
Leu Val Gly Gln Asp Ser Ala Arg Val Arg Glu Leu Trp Thr Ala Val
            340                 345                 350 gat cat ggt ggc aag ttt gac ctg aat gca gac ggt tat ttt gaa aaa     1104
Asp His Gly Gly Lys Phe Asp Leu Asn Ala Asp Gly Tyr Phe Glu Lys
        355                 360                 365 gtg gct gac ttt ggt ttt gtt tcc ggc cat agt aac cat gcc aac cgc     1152
Val Ala Asp Phe Gly Phe Val Ser Gly His Ser Asn His Ala Asn Arg
    370                 375                 380 atg caa acc ata cgc act acc aaa gaa aaa tat ggc gtg acc att gat     1200
Met Gln Thr Ile Arg Thr Thr Lys Glu Lys Tyr Gly Val Thr Ile Asp
385                 390                 395                 400 acg cat act gcc gat ggc ttg aaa gtc gcc ctc gaa cac cgt cag ccg     1248
Thr His Thr Ala Asp Gly Leu Lys Val Ala Leu Glu His Arg Gln Pro
                405                 410                 415 aat gtg ccc atg ctg gta ttg gaa acg gca ttg ccg gcc aaa ttt gaa     1296
Asn Val Pro Met Leu Val Leu Glu Thr Ala Leu Pro Ala Lys Phe Glu
            420                 425                 430 gat gcg att gtg gaa gcg ctg ggt gaa gtg cct gag cgt ccg gcc agc     1344
Asp Ala Ile Val Glu Ala Leu Gly Glu Val Pro Glu Arg Pro Ala Ser
```

```
            435                 440                 445
ctg gtt ggc ctg gag gac ctg cca cag aaa tcc acg gtg atg gat gtg    1392
Leu Val Gly Leu Glu Asp Leu Pro Gln Lys Ser Thr Val Met Asp Val
    450                 455                 460 agc gtc gat gcg att aaa gcc ttt att gct gct aac aca tga            1434
Ser Val Asp Ala Ile Lys Ala Phe Ile Ala Ala Asn Thr
465                 470                 475
```

<210> SEQ ID NO 54
<211> LENGTH: 477
<212> TYPE: PRT
<213> ORGANISM: Methylophilus methylotrophus

<400> SEQUENCE: 54

```
Met Lys Tyr Ile Ser Thr Arg Gly Gln Ser Pro Ala Leu Thr Phe Ser
1               5                   10                  15

Glu Ile Leu Leu Gly Gly Leu Ala Pro Asp Gly Gly Leu Tyr Leu Pro
                20                  25                  30

Glu Gln Tyr Pro Gln Phe Ser Asp Ala Asp Leu Asn Ala Met Arg Gly
            35                  40                  45

Met Asn Tyr Arg Glu Leu Ala Phe Ala Ile Leu Ser Arg Leu Val Asp
        50                  55                  60

Asp Ser Asp Ile Pro His Ala Asp Leu Lys Ala Ile Ile Asp Lys Thr
65                  70                  75                  80

Tyr Arg Ala Asp Val Tyr Gln Tyr Val Arg Ala Gly Gln Asn Ala Glu
                85                  90                  95

Asp Ile Thr Pro Thr Leu Lys Leu Glu Asp Asn Leu Tyr Leu Leu Ser
            100                 105                 110

Leu Ser Asn Gly Pro Thr Leu Ala Phe Lys Asp Met Ala Met Gln Leu
        115                 120                 125

Leu Gly Asn Leu Phe Glu Tyr Val Leu Thr Lys Thr Gly Gln Thr Thr
    130                 135                 140

Asn Ile Leu Gly Ala Thr Ser Gly Asp Thr Gly Ser Ala Ala Glu Tyr
145                 150                 155                 160

Ala Met Arg Gly Lys Lys Gly Val Arg Val Phe Met Leu Ser Pro Tyr
                165                 170                 175

Gln Lys Met Ser Arg Phe Gln Thr Ala Gln Met Phe Ser Leu Gln Asp
            180                 185                 190

Asp Asn Ile Phe Asn Ile Ala Val Lys Gly Val Phe Asp Asp Ala Gln
        195                 200                 205

Asp Met Val Lys Ala Val Ser Asn Asp His Asn Phe Lys Ala Gln Tyr
    210                 215                 220

Lys Ile Gly Ala Val Asn Ser Ile Asn Trp Gly Arg Ile Ala Ala Gln
225                 230                 235                 240

Ile Ile Tyr Tyr Phe Lys Gly Tyr Leu Ala Val Thr Thr Asn Asn Ser
                245                 250                 255

Gln Lys Val Ser Phe Thr Val Pro Ser Gly Asn Phe Gly Asn Ile Cys
            260                 265                 270

Ala Gly His Ile Ala Arg Met Met Gly Leu Pro Ile Asp Gln Leu Val
        275                 280                 285

Val Ala Thr Asn Glu Asn Asp Val Leu Asp Glu Phe Asn Thr Gly
    290                 295                 300

Val Tyr Ala Pro Arg Gly Ser Ala Asn Thr Tyr His Thr Ser Ser Pro
305                 310                 315                 320

Ser Met Asp Ile Ser Lys Ala Ser Asn Phe Glu Arg Phe Val Tyr Asp
```

-continued

```
                    325                 330                 335
Leu Val Gly Gln Asp Ser Ala Arg Val Arg Glu Leu Trp Thr Ala Val
                340                 345                 350

Asp His Gly Gly Lys Phe Asp Leu Asn Ala Asp Gly Tyr Phe Glu Lys
                355                 360                 365

Val Ala Asp Phe Gly Phe Val Ser Gly His Ser Asn His Ala Asn Arg
    370                 375                 380

Met Gln Thr Ile Arg Thr Thr Lys Glu Lys Tyr Gly Val Thr Ile Asp
385                 390                 395                 400

Thr His Thr Ala Asp Gly Leu Lys Val Ala Leu Glu His Arg Gln Pro
                405                 410                 415

Asn Val Pro Met Leu Val Leu Glu Thr Ala Leu Pro Ala Lys Phe Glu
                420                 425                 430

Asp Ala Ile Val Glu Ala Leu Gly Glu Val Pro Glu Arg Pro Ala Ser
                435                 440                 445

Leu Val Gly Leu Glu Asp Leu Pro Gln Lys Ser Thr Val Met Asp Val
    450                 455                 460

Ser Val Asp Ala Ile Lys Ala Phe Ile Ala Ala Asn Thr
465                 470                 475
```